(12) United States Patent
Kamalesh Babu et al.

(10) Patent No.: US 8,680,279 B2
(45) Date of Patent: Mar. 25, 2014

(54) COMPOUNDS FOR THE TREATMENT OF NEUROLOGICAL DISORDERS

(75) Inventors: Ruppa Poornachary Kamalesh Babu, Alpharetta, GA (US); Scott James Myers, Avondale Estates, GA (US)

(73) Assignee: Neurop, Inc., Atlanta, GA (US)

( * ) Notice: Subject to any disclaimer, the term of this patent is extended or adjusted under 35 U.S.C. 154(b) by 0 days.

(21) Appl. No.: 13/495,561

(22) Filed: Jun. 13, 2012

(65) Prior Publication Data

US 2012/0302543 A1 Nov. 29, 2012

Related U.S. Application Data

(63) Continuation of application No. PCT/US2010/060571, filed on Dec. 15, 2010.

(60) Provisional application No. 61/286,708, filed on Dec. 15, 2009.

(51) Int. Cl.
| | | |
|---|---|---|
| *C07D 215/00* | (2006.01) | |
| *C07D 211/06* | (2006.01) | |
| *A01N 43/00* | (2006.01) | |
| *A61K 31/44* | (2006.01) | |
| *A61K 31/47* | (2006.01) | |
| *A61K 31/4375* | (2006.01) | |

(52) U.S. Cl.
CPC .................................. *A61K 31/4375* (2013.01)
USPC ...... 546/158; 546/226; 514/210.18; 514/330; 514/312

(58) Field of Classification Search
CPC .................................................. A61K 31/4375
USPC .............. 546/158, 226; 514/210.18, 330, 312
See application file for complete search history.

(56) References Cited

U.S. PATENT DOCUMENTS

| | | | |
|---|---|---|---|
| 6,548,516 B1 | 4/2003 | Prucher et al. | |
| 7,435,744 B2 | 10/2008 | Domany et al. | |
| 2006/0199824 A1 | 9/2006 | Sun et al. | |

FOREIGN PATENT DOCUMENTS

| | | | |
|---|---|---|---|
| WO | WO 03/010159 | | 2/2003 |
| WO | WO 2004/006846 | * | 1/2004 |
| WO | WO 2005/013998 | * | 2/2005 |
| WO | WO 2005/032484 | * | 4/2005 |
| WO | WO 2006/010967 | | 2/2006 |
| WO | WO 2008/16973 | * | 7/2008 |
| WO | WO 2010/141809 | | 12/2010 |

* cited by examiner

*Primary Examiner* — John Mabry
(74) *Attorney, Agent, or Firm* — King & Spalding

(57) ABSTRACT

Provided are compounds, pharmaceutical compositions and methods of treatment or prophylaxis of certain neurologic disorders, including disorders related to NMDA receptor activation, neuropsychiatric disorders, neurodegenerative disorders and other neurologic diseases, disorders and related conditions. The compounds are of the Formulas I and Ia-Ij as described herein.

9 Claims, 1 Drawing Sheet

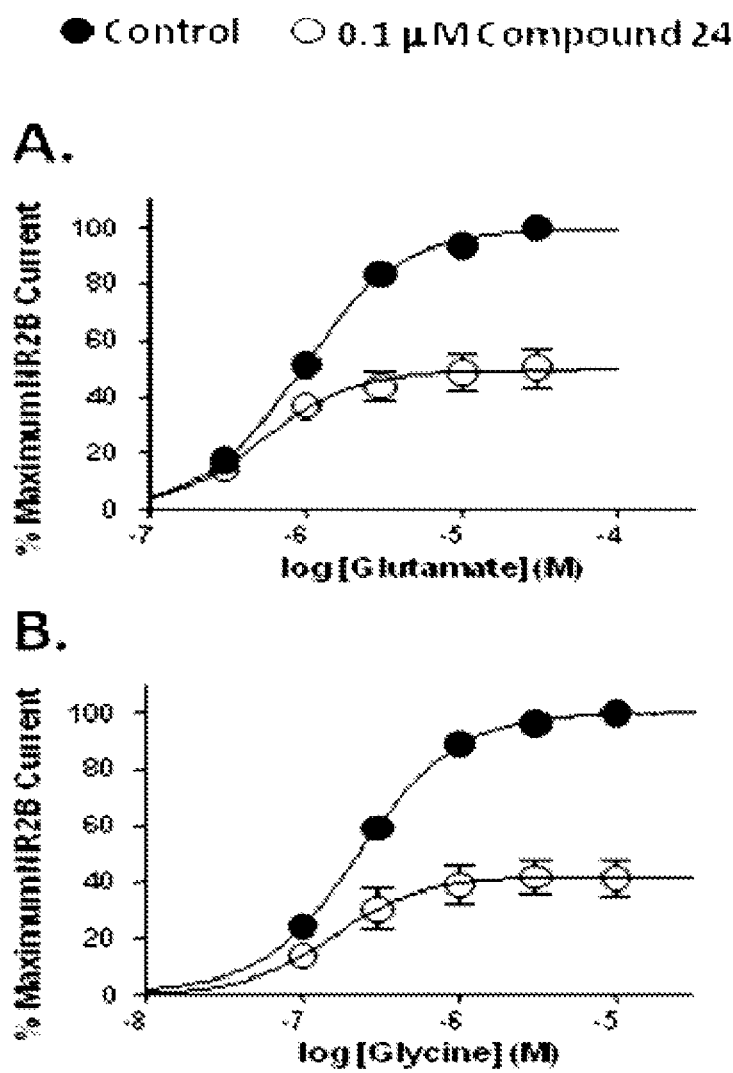

COMPOUNDS FOR THE TREATMENT OF NEUROLOGICAL DISORDERS

CROSS-REFERENCE TO RELATED APPLICATIONS

This application is a continuation of International Application No. PCT/US2010/060571, filed Dec. 15, 2010, which claims priority to U.S. Provisional Application No. 61/286,708, filed Dec. 15, 2009.

FIELD OF THE INVENTION

The present invention provides certain compounds useful in the treatment or prophylaxis of neurologic disorders, including neuropsychiatric disorders such as depression and anxiety, neurodegenerative disorders and other diseases and disorders of the neurological system. In certain instances, these neurologic disorders result from NMDA-receptor activation.

BACKGROUND OF THE INVENTION

Neurologic disorders are abnormal conditions of the nervous system. They can be categorized according to the structure or primary location affected, the nature of the dysfunction or the primary cause (e.g., genetic disorder, injury, infection). Some neurologic disorders, like Parkinson's disease and stroke, are well-known while others are very rare. One recent study by the World Health Organization (WHO) found that neurologic disorders account for almost 11% of total global disease burden worldwide. Collectively, the burden of neurologic disorders is hard to overstate, and includes direct health care costs, disability, quality of life and lost productivity. Alzheimer's disease alone drains more than $148 billion from the U.S. economy each year. The burden of neurologic disorder is expected to increase on a global basis, as demographic changes in the world's most populous countries will result in a significant increase in the number of persons with neurodegenerative diseases over the next few decades.

NMDA Receptors

There are four classes of excitatory amino acids (EAA) receptors in brain that mediate neuronal activity: NMDA (N-methyl-D-aspartate), AMPA (2-amino-3-(methyl-3-hydroxyisoxazol-4-yl)propanoic acid), kainate and metabotropic receptors. Glutamate receptors mediate fast excitatory synaptic transmission in the central nervous system and are widely localized on neuronal and non-neuronal cells, regulating a broad spectrum of processes in the central and peripheral nervous system. The NMDA subtype of glutamate-gated ion channels mediates excitatory synaptic transmission between neurons in the central nervous system (Traynelis et al. *Pharmacol Rev* (2010) 62:405-96).

NMDA receptors are composed of GluN1, GluN2 (A, B, C, and D), and GluN3 (A and B) subunits, which determine the functional properties of native NMDA receptors. Co-expression of the GluN1 subunit with one or more GluN2 subunits is required to form functional channels. In addition to glutamate binding on GluN2 subunits, the NMDA receptor requires the binding of a co-agonist, glycine at GluN1 subunits, to allow the receptor to function. A glycine binding site is also found on GluN3 subunits. At resting membrane potentials, NMDA receptors are largely inactive due to a voltage-dependent block of the channel pore by magnesium ions. Depolarization releases this channel block and permits passage of calcium and monovalent ions such as sodium ions.

NMDA receptors participate in a wide range of both physiological and pathological processes in the central nervous system and are found in neurons throughout the brain including the cortico-limbic regions which have been postulated to play a role in emotional functions, anxiety and depression (Tzschentke T M (2002) *Amino Acids* 23:147-152). Many studies have demonstrated antidepressant-like effects of various antagonists of the NMDA receptors. The antidepressant-like activity of competitive, uncompetitive, and non-competitive antagonists of NMDA receptors has been reported (Trullas, et al. (1990) *Eur J Pharmacol* 185:1-10; Layer et al., (1995) *Pharmacol Biochem Behavi* 52:621-627; Decollogne, et al. (1997) *Pharmacol Biochem Behav* 58:261-268; Przegaliñski, et al. (1997) *Neuropharmacology* 36:31-37; Przegaliñski, et al. (1998) *Pol J Pharmacol* 50: 349-354; Skolnick P *Eur J Pharmacol* 375:31-40; Berman et al., (2000) *Biol Psychiatry* 47:351-4; Kroczka, et al. (2000) *Pol J Pharmacol* 52:403-406; Skolnick, et al. (2001) *Pharmacol Res* 43:411-423; Kroczka, et al. (2001) *Brain Res Bull* 55:297-300; Poleszak, et al. (2004) *Pharmacol Biochem Behav* 78:7-12; Zarate et al., (2006) *Arch Gen Psychiatry* 63:856-64; Poleszak, et al. (2007) *Pharmacol Biochem Behav* 88:158-164; Poleszak, et al. (2007) *Pharmacol Rep* 57:654-658; Maeng et al., (2008) *Biol Psychiatry* 63:349-52; Preskorn et al., (2008) *J Clin Psychopharm* 28:631-637, Li et al., (2010) *Science* 329: 959-64, Diazgranados et al (2010) *Arch Gen Psych* 67: 793-802. Poleszak, et al. showed that the NMDA receptor binding of certain antagonists, specifically CGP 37849 and L-701,324, are directly related to their antidepressant-like effects (Poleszak, et al. (2007) *Pharm. Reports* 59:595-600).

NMDA receptor antagonists may also be beneficial in the treatment of chronic pain. For example, it has been reported that NMDA receptor antagonists produce an analgesic effect under certain conditions (Wong, et al. (1995) *Acta Anaesthesiologica Sinica* 33, 227-232). Nerve ligation, carrageenan-induced hyperalgesia, and wind-up pain in rats were all relieved by non-competitive, competitive, and GluN2B selective NMDA receptor antagonists (Boyce et al., (1999) *Neuropharmacol* 38: 611-623). Chronic pain, including neuropathic pain such as that due to injury of peripheral or central nerves, has often proved very difficult to treat. Treatment of chronic pain with ketamine and amantadine has proven beneficial, and it is believed that the analgesic effects of ketamine and amantadine are mediated by block of NMDA receptors. Several case reports have indicated that systemic administration of amantadine or ketamine substantially reduces the intensity of trauma-induced neuropathic pain. Small-scale double blind, randomized clinical trials corroborated that amantadine could significantly reduce neuropathic pain in cancer patients (Pud et al. (1998), Pain 75:349-354) and ketamine could reduce pain in patients with peripheral nerve injury (Felsby et al. (1996), Pain 64:283-291), peripheral vascular disease (Perrson et al. (1998), Acta Anaesthesiol Scand 42:750-758), or kidney donors (Stubhaug et al. (1997), Acta Anaesthesiol Scand 41:1124-1132). "Wind-up pain" produced by repeated pinpricking was also dramatically reduced. These findings suggest that central sensitization caused by nociceptive inputs can be prevented by administration of NMDA receptor antagonists.

NMDA receptor antagonists can also be beneficial in the treatment of Parkinson's Disease (Blandini and Greenamyre (1998), Fundam Clin Pharmacol 12:4-12), brain cancers (Takano, T., et al. (2001), Nature Medicine 7:1010-1015; Rothstein, J. D. and Bren, H. (2001) Nature Medicine 7:994-995; Rzeski, W., et al. (2001), Proc. Nat'l Acad. Sci. 98:6372), and neuropsychiatric disorders including depressive disorders and bipolar disorders, which affect more than 60 million Americans each year. Depression affects approximately one in six individuals in the United States at some point in their lives (Hyman, (2008) *Nature* 455:890-893). The World Health Organization (2001) ranks depression as the single most common cause of disability for individuals aged 15-44. Therapies for depression include a diversity of antidepressant medications, psychotherapy, and for those failing these measures, electroconvulsive therapy and transcranial magnetic stimulation. Unfortunately, an estimated 30-40% of affected individuals are resistant to these current, diverse therapies (Rush et al., (1998) *J Clin Psychiatry* 59(suppl 20):73-84.). Functional antagonists of the NMDA receptor complex exhibit antidepressant-like activity in models of depression. Trullas and Skolnick demonstrated the antidepressant activity of AP-7, MK-801 and ACPC in the mouse forced swim test (FST) and tail suspension test (TST) (Trullas R, Skolnick P (1990) *Eur J Pharmacol* 185:1-10). A number of reports have confirmed and extended this finding to also include GluN2B NMDA receptor antagonists (Layer et al., (1995) *Pharmacol Biochem Behavi* 52:621-627. Maeng et al., (2008) *Biol Psychiatry* 63:349-52, Li et al., (2010) *Science* 329: 959-64).

U.S. Pat. No. 7,019,016 to Pfizer provides methods for treating certain disorders including depression which comprise administration of certain GluN2B subunit selective NMDA antagonists. The disorders that can be treated by the invention include hearing loss, vision loss, neurodegeneration caused by epileptic seizures, neurotoxin poisoning, Restless Leg Syndrome, multi-system atrophy, non-vascular headache, and depression.

U.S. Pat. No. 5,710,168 claims the use of certain compounds having GluN2B subunit selectivity for treating a disease or condition which is susceptible to treatment by blocking of NMDA receptor sites, including traumatic brain injury, spinal cord trauma, pain, psychotic conditions, drug addiction, migraine, hypoglycemia, anxiolytic conditions, urinary incontinence, and ischemic events arising from CNS surgery, open heart surgery or any procedure during which the function of the cardiovascular system is compromised.

U.S. Pat. No. 6,479,553 to AstraZeneca provides certain compounds, in particular memantine, budipine, amantidine, 5-aminocarbonyl-10,11-dihydro-5H-dibenzo[a,d]cyclohepten-5,10-imine, dextromethorphan and NPS 1506, and the compounds disclosed in EP 279 937 and EP 633 879, specifically (S)-1-phenyl-2-(2-pyridyl)ethanamine as potentially useful as antidepressant agents. In particular, the compounds were expected to be useful in the treatment of depression associated with neurodegenerative disorders such as Alzheimer's disease.

U.S. Pat. No. 6,432,985 to Hoffman La-Roche provides certain neuroprotective substituted piperidine compounds with activity as NMDA GluN2B subtype selective antagonists PCT Publication WO 06/017409 to Merck & Co. provides certain 1,3-disubstituted heteroaryl compounds are N-methyl-D-aspartate receptor antagonists useful for treating neurological condition e.g. pain, Parkinson's disease, Alzheimer's disease, anxiety, epilepsy and stroke.

PCT Publication WO 02/072542, to Emory University describes a class of pH-dependent NMDA receptor antagonists that exhibit pH sensitivity tested in vitro using an oocyte assay and in an experimental model of epilepsy.

PCT Publication WO 09/006,437, to Emory University and NeurOp, Inc., describes a class of pH sensitive NMDA antagonists for treatment of disorders including stroke, traumatic brain injury, neuropathic pain, epilepsy, and related neurologic events or neurodegeneration.

While NMDA-receptor antagonists might be useful to treat a number of disorders, to date, dose-limiting side effects have prevented clinical use of NMDA receptor antagonists for these conditions. Thus, despite the potential for glutamate antagonists to treat many serious diseases, the severity of the side effects have caused many to abandon hope that a well-tolerated NMDA receptor antagonist could be developed (Hoyte L. et al (2004) *Curr. Mol. Med.* 4(2): 131-136; Muir, K. W. and Lees, K. R. (1995) *Stroke* 26:503-513; Herrling, P. L., ed. (1997) "Excitatory amino acid clinical results with antagonists" Academic Press; Parsons et al. (1998) *Drug News Perspective* II: 523 569).

pH Sensitive NMDA Receptors

The extracellular pH is highly dynamic in mammalian brain, and influences the function of a multitude of biochemical processes and proteins, including glutamate receptor function. The pH-sensitivity of the NMDA receptor has received increasing attention for at least two reasons. First, the $IC_{50}$ value for proton inhibition of pH 7.4 places the receptor under tonic inhibition at physiological pH. Second, pH changes are extensively documented in the central nervous system during synaptic transmission, glutamate receptor activation, glutamate receptor uptake, and prominently during pathological states such as ischemia and seizures (Siesjo, B K (1985), *Progr Brain Res* 63:121-154; Chesler, M (1990), *Prog Neurobiol* 34:401-427; Chesler and Kaila (1992), *Trends Neurosci* 15:396-402; Amato et al. (1994), *J Neurophysiol* 72:1686-1696). During stroke, transient ischemia leads to a dramatic drop of pH to 6.4-6.9 (Mutch & Hansen (1984) *J Cereb Blood Flow Metab* 4: 17-27, Smith et al. (1986) *J Cereb Blood Flow Metab* 6: 574-583; Nedergaard et al. (1991) *Am J Physiol* 260(Pt3): R581-588; Katsura et al (1992a) *Euro J Neursci* 4: 166-176; and Katsura & Siesjo (1998) "Acid base metabolism in ischemia" in pH and Brain function (Eds Kaila & Ransom) Wiley-Liss, New York). In addition to ischemia, there are various other examples of situations in which pH changes under normal and abnormal conditions, including neuropathic pain (Jendelova & Sykova (1991) *Glia* 4: 56-63; Chvatal et al. (1988) *Physiol Bohemoslov* 37: 203-212; Sykova et al. (1992) *Can J Physiol Pharmacol* 70: Suppl S301-309; Sykova & Svoboda (1990) *Brain Res* 512: 181-189) and Parkinson's disease, which may result in a lower local pH (see, for example, Chesler (1990) *Prog Neurobiol* 34: 401-427, Chesler & Kaila (1992) *Tr Neurosci* 15: 396-402, and Kaila & Chesler (1998) "Activity evoked changes in extracellular pH" in pH and Brain function (eds Kaila and Ransom). Wiley-Liss, New York).

Acidification also occurs during seizures (Siesjo et al (1985) *J Cereb Blood Flow Metab* 5: 47-57; Balestrino & Somjen (1988) *J Physiol* 396: 247-266; and Xiong & Stringer (2000) *J Neurophysiol* 83: 3519-3524). In addition, other types of brain injury can result in acidification (Kaku et al. (1993), *Science* 260:1516-1518; Munir and McGonigle (1995), *J Neurosci* 15:7847-7860; Vornov et al. (1996), *J Neurochem* 67:2379-2389; Gray et al. (1997), *J Neurosurg Anesthesiol* 9:180-187; O'Donnell and Bickler (1994), *Stroke* 25:171-177; reviewed by Tombaugh and Sapolsky (1993), *J Neurochem* 61:793-803) and seizure maintenance (Balestrino and Somjen (1988), *J Physiol* (Lond) 396:247-266; Velisek et al. (1994), *Exp Brain Res* 101:44-52).

PCT Publication WO 06/023957 to Emory University describes processes for selection of a compound which may be useful in the treatment of an ischemic injury or a disorder that lowers the pH in a manner that activates the NMDA receptor antagonist.

There remains a need for improved compounds and methods for the treatment of neurologic disorders that have reduced toxicity. In particular, there is a need for improved treatments for neuropsychiatric disorders, neurodegenerative disorders and other neurological disorders of diverse origin that have enhanced efficacy and reduced side effects.

SUMMARY OF THE INVENTION

Compounds of Formula I are provided for the treatment, prophylaxis or reduction in symptoms of neurologic disorders including but not limited to neuropsychiatric and neurodegenerative diseases and disorders. In certain instances, the disorders are specifically known to result from NMDA receptor activation. In particular, compounds for use in the treatment or prophylaxis of depression or anxiety in a host at risk of or suffering from the disorder are provided. Certain compounds described herein have enhanced activity in brain tissue having lower-than-normal pH due to pathological conditions.

In one particular embodiment, methods of treatment or prophylaxis of neuropsychiatric disorders, in particular depression and anxiety are provided comprising administering a compound of Formula I or a pharmaceutically acceptable salt, ester, prodrug or derivative thereof, optionally in combination with a pharmaceutically acceptable carrier, to a host in need thereof:

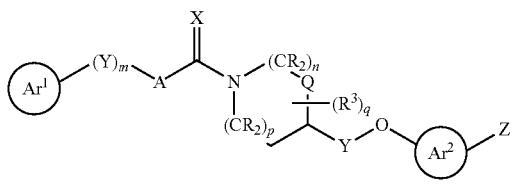

Formula I wherein:
$Ar^1$ and $Ar^2$ are independently substituted or unsubstituted aryl, heteroaryl or heterocycle;
m, n, p and q are each independently 0, 1 or 2;
A is a bond, $CH_2$, CH=CH, C≡C, NR, O or S;
Each $R^3$ is independently selected from $C_1$-$C_6$ alkyl, $C_3$-$C_6$ cycloalkyl, $C_1$-$C_6$ haloalkyl, —OH, O-alkyl, O-aryl, —SH, —S-alkyl, fluoro, chloro, bromo, iodo, nitro, or cyano;
Q is selected from $CH_2$, CHR, $CR_2$, NH, NR, O and S;
Each Y is independently $CR_2$ or $CR_2CR_2$;
each R is independently selected from H, OH or alkyl, in particular $C_{1-4}$ alkyl;
X is O, S or $CH_2$; and
Z is OH, $NR^6R^7$, $NR^8SO_2(C_1$-$C_6$ alkyl), $NR^8C(O)NR^6R^7$, $NR^8C(S)NR^6R^7$, $NR^8CHO$, $NR^8C(O)(C_1$-$C_6$ alkyl), $NR^8C(O)O(C_1$-$C_6$ alkyl), $NR^8$-dihydrothiazole, or $NR^8$-dihydroimidazole wherein each $R^6$, $R^7$ and $R^8$ is independently H, $C_1$-$C_6$ alkyl or $C_6$-$C_{12}$ aralkyl or Z comes together with $Ar^2$ together to form a substituted or unsubstituted heterocyclic ring system with $Ar^2$.

In general embodiments, $Ar^2(Z)$ is a proton donor system. It has been found that in binding to and inhibiting NMDA receptors, a proton donor provides additional activity in stabilizing the molecule in the receptor. In typical embodiments, $Ar^1$ is a 3 to 7 membered aryl, heteroaryl or heterocycle.

In one embodiment, $Ar^1$ is substituted with small groups or less bulky groups, for example chloro, fluoro, methyl, or trifluoromethyl, to enhance binding to NMDA receptors.

In specific embodiments, n and p are each 1. It has been found that a six membered ring system in this position provides strong pH dependence with high activity at pH below 7.0 and reduced activity at higher pH. In other embodiments, n and p are each 0. It has been found that a four membered ring system at this position provides highly active compounds at all pH levels.

In certain embodiments, the compounds are used for the treatment of neuropsychiatric disorders, and in particular, mood disorders, for example depressive disorders and bipolar disorders. Depressive disorders include, for example, major depressive disorder, depression, atypical depression, melancholic depression, psychotic major depression, catatonic depression, postpartum depression, treatment-resistant depression, treatment-resistant bipolar depression, seasonal affective disorder (SAD), dysthymia, and depressive disorders not otherwise specified (DD-NOS) such as those disorders that are impairing but do not otherwise meet the criteria for a specific depressive disorder, such as recurrent brief depression, minor depressive disorders or minor depression. Bipolar disorder, or manic depression, or a mood disorder described by alternating periods of mania and depression, includes, for example bipolar I, which is distinguished by the presence of one or more manic episodes or mixed episodes with or without major depressive episodes; bipolar II, which consists of recurrent intermittent hypomanic and depressive episodes; cyclothymia, which consists of recurrent hypomanic and dysthymic episodes, but no full manic episodes or major depressive episodes; and bipolar disorder not otherwise specified (BD-NOS), which are disorders wherein a patient suffers from some symptoms in the bipolar spectrum (e.g. manic and depressive symptoms) but does not otherwise meet the criteria for a specific bipolar disorder diagnosis.

In certain embodiments, the compounds are used for the treatment of a depressive disorder in a host diagnosed with the disorder. In certain other embodiments, the compounds are used for treatment of a bipolar disorder in a host diagnosed with the disorder. The compounds can also be used to prevent or diminish future depressive or manic episodes. The compounds can be provided on a seasonal basis, especially in a host who has been diagnosed or is at risk of SAD or of depression. In certain other embodiments, the compounds are useful in the treatment or prophylaxis of a disorder associated with a physiological insult. The disorder can include depression or bipolar disorder associated with an injury or with aging.

In other embodiments, the compounds are used for the treatment of neurodegenerative disorders, and in particular, Parkinson's disease, Alzheimer's disease, Huntington's disease and Amyotrophic lateral sclerosis (ALS).

In certain other embodiments, compounds are provided for the treatment or prophylaxis of a disorder associated with NMDA receptor activation. In certain embodiments, the compounds are for treatment of a disorder in which extracellular pH is reduced below 7. In certain specific embodiments, extracellular pH in a specific brain region is reduced below 6.9, or 6.8, or 6.7, or 6.6, or 6.5 or 6.4.

In certain embodiments, compounds are provided for the treatment or prophylaxis of stroke, transient ischemia, global ischemia and hypoxia.

In certain other embodiments, compounds are provided for the treatment of pain. In one embodiment, the compounds are used to treat neuropathic pain or inflammatory pain.

In other embodiments, compounds are provided for the treatment or prophylaxis of epilepsy, traumatic brain injury or spinal cord trauma.

In certain embodiments, the compounds are administered to a host in need thereof. In certain other embodiments, the compounds are administered in combination or alternation with other compounds, in particular embodiments another compound useful in the treatment or prophylaxis of neuropsychiatric disorders.

BRIEF DESCRIPTION OF FIGURES

FIG. 1 shows the results of human GluN2B-NMDA receptors expressed in *Xenopus laevis* and perfused with glutamate, glycine and with or without 0.1 µM compound 24. Results shown are the mean±SEM of 7 (panel A) or 6 (panel B) oocytes.

DETAILED DESCRIPTION OF THE INVENTION

Certain compounds are provided as useful in the treatment or prophylaxis of neurologic disorders. In certain instances, the disorders are known to result from NMDA receptor activation. Typically, these compounds act as NMDA receptor antagonists. In certain embodiments, the compounds are allosteric NMDA inhibitors. In particular, compounds of Formula I are provided for treatment or prophylaxis of neuropsychiatric disorders.

Definitions

Whenever a term in the specification is identified as a range (i.e. $C_{1-4}$ alkyl), the range independently refers to each element of the range. As a non-limiting example, $C_{1-4}$ alkyl means, independently, $C_1$, $C_2$, $C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "alkyl" is used herein, unless otherwise specified, refers to a substituted or unsubstituted, saturated, straight, branched, or cyclic (also identified as cycloalkyl), primary, secondary, or tertiary hydrocarbon, including but not limited to those of $C_1$ to $C_6$. Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thio, sulfonyl, ester, carboxylic acid, amide, phosphonyl, phosphinyl, thioether, oxime, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991. In certain embodiments, alkyl may be optionally substituted by one or more fluoro, chloro, bromo, iodo, hydroxy, heterocyclic, heteroaryl, carboxy, alkoxy, nitro, $NH_2$, $N(alkyl)_2$, $NH(alkyl)$, alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—NH$_2$, —C(O)—N(H)O(H or alkyl), —S(O)$_2$—NH$_2$, —S(O)$_n$—N(H or alkyl)$_2$ and/or —S(O)$_2$—N(H or alkyl)$_2$.

The term "halo" or "halogen," refers to chloro, bromo, iodo, or fluoro.

The term "heteroaryl" or "heteroaromatic," refers to an aromatic that includes at least one sulfur, oxygen, nitrogen or phosphorus in the aromatic ring. The term "heterocyclic" refers to a non-aromatic cyclic group wherein there is at least one heteroatom, such as oxygen, sulfur, nitrogen, or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, pteridinyl, aziridines, thiazole, isothiazole, oxadiazole, thiazine, pyridine, pyrazine, piperazine, piperidine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic or heterocyclic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. Nonlimiting examples include dihydropyridine and tetrahydrobenzimidazole. In some embodiment, the heteroaryl may be optionally substituted by one or more fluoro, chloro, bromo, iodo, hydroxy, heterocyclic, heteroaryl, carboxy, alkoxy, nitro, $NH_2$, $N(alkyl)_2$, $NH(alkyl)$, alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—NH$_2$, —C(O)—N(H)O(H or alkyl), —S(O)$_2$—NH$_2$, —S(O)$_n$—N(H or alkyl)$_2$ and/or —S(O)$_2$—N(H or alkyl)$_2$. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-tolylsulfonyl.

The term "aryl," unless otherwise specified, refers to a carbon based aromatic ring, including phenyl, biphenyl, or naphthyl. The aryl group can be optionally substituted with one or more moieties selected from the group consisting of hydroxyl, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991. In certain embodiments, the aryl group is optionally substituted by one or more fluoro, chloro, bromo, iodo, hydroxy, heterocyclic, heteroaryl, carboxy, alkoxy, nitro, $NH_2$, $N(alkyl)_2$, NH(alkyl), alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—$NH_2$, —C(O)—N(H)O(H or alkyl), —S(O)$_2$—$NH_2$, —S(O)$_n$—N(H or alkyl)$_2$ and/or —S(O)$_2$—N(H or alkyl)$_2$.

The term "aralkyl," unless otherwise specified, refers to an aryl group as defined above linked to the molecule through an alkyl group as defined above.

The term "alkaryl," unless otherwise specified, refers to an alkyl group as defined above linked to the molecule through an aryl group as defined above. Other groups, such as acyloxyalkyl, alkoxyalkyl, alkoxycarbonyl, alkoxycarbonylalkyl, alkylaminoalkyl, alkylthioalkyl, amidoalkyl, aminoalkyl, carboxyalkyl, dialkylaminoalkyl, haloalkyl, heteroaralkyl, heterocyclicalkyl, hydroxyalkyl, sulfonamidoalkyl, sulfonylalkyl and thioalkyl are named in a similar manner.

The term "alkoxy," unless otherwise specified, refers to a moiety of the structure —O-alkyl, wherein alkyl is as defined above.

The term "acyl," refers to a group of the formula C(O)R' or "alkyl-oxy", wherein R' is an alkyl, aryl, alkaryl or aralkyl group, or substituted alkyl, aryl, aralkyl or alkaryl.

The term "alkenyl" The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to ($C_2$-$C_8$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "carbonyl" refers to a functional group composed of a carbon atom double-bonded to an oxygen atom: —C=O, Similarly, C(O) or C(=O) refers to a carbonyl group.

The term "amino" refers to —$NH_2$, —NH(alkyl) or —N(alkyl)$_2$.

The term "thio" indicates the presence of a sulfur group. The prefix thio-denotes that there is at least one extra sulfur atom added to the chemical. The prefix 'thio-' can also be placed before the name of a compound to mean that an oxygen atom in the compound has been replaced by a sulfur atom. Although typically the term "thiol" is used to indicate the presence of —SH, in instances in which the sulfur atom would be have improper valance a radical if the hydrogen is improperly designated, the terms 'thio' and 'thiol' are used interchangeably, unless otherwise indicated.

The term "amido" indicates a group (H or alkyl)-C(O)—NH—.

The term "carboxy" designates the terminal group —C(O)OH.

The term "sulfonyl" indicates an organic radical of the general formula (H or alkyl)-S(=O)$_2$—(H or alkyl'), where there are two double bonds between the sulfur and oxygen.

The term "pharmaceutically acceptable salt" refers to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —$NR^+$ $A^-$, wherein R is H or alkyl and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term "ester" refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl for example phenoxymethyl, aryl including phenyl optionally substituted with halogen, $C_1$ to $C_4$ alkyl or $C_1$ to $C_4$ alkoxy. The term "ester" may also refer to a sulfonate ester, for example alkyl or aralkyl including methanesulfonyl; or a mono-, di- or triphosphate ester.

Pharmaceutically acceptable "prodrugs" can refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated decacylated, phosphorylated or dephosphorylated to produce the active compounds.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

It should be understood that the various possible stereoisomers of the groups mentioned above and herein are within the meaning of the individual terms and examples, unless otherwise specified. As an illustrative example, "1-methyl-butyl" exists in both (R) and the (S) form, thus, both (R)-1-methyl-butyl and (S)-1-methyl-butyl is covered by the term "1-methyl-butyl", unless otherwise specified.

Compounds

In one embodiment, compounds of Formula I are provided, or a pharmaceutically acceptable salt, ester, prodrug or derivative thereof, as well as methods of treatment or prophylaxis of neurologic disorders comprising administering the compound to a host in need thereof:

Formula I

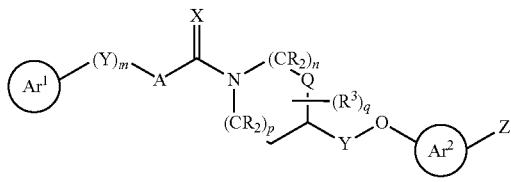

wherein:
Ar¹ and Ar² are independently substituted or unsubstituted aryl, heteroaryl or heterocycle;
m, n, p and q are each independently 0, 1 or 2;
A is a bond, $CH_2$, CH=CH, C≡C, NR, O or S;
Each $R^3$ is independently selected from $C_1$-$C_6$ alkyl, $C_3$-$C_6$ cycloalkyl, $C_1$-$C_6$ haloalkyl, —OH, O-alkyl, O-aryl, —SH, —S-alkyl, fluoro, chloro, bromo, iodo, nitro, or cyano;
Q is selected from $CH_2$, CHR, $CR_2$, NH, NR, O and S;
Each Y is independently $CR_2$ or $CR_2CR_2$;
each R is independently selected from H, OH or alkyl, in particular $C_{1-4}$ alkyl;
X is O or S; and
Z is OH, $NR^6R^7$, $NR^8SO_2$($C_1$-$C_6$ alkyl), $NR^8C(O)NR^6R^7$, $NR^8C(S)NR^6R^7$, $NR^8CHO$, $NR^8C(O)$($C_1$-$C_6$ alkyl), $NR^8C(O)O$($C_1$-$C_6$ alkyl), $NR^8$-dihydrothiazole, or $NR^8$-dihydroimidazole wherein each $R^6$, $R^7$ and $R^8$ is independently H, $C_1$-$C_6$ alkyl or $C_6$-$C_{12}$ aralkyl or Z comes together with $Ar^2$ to form a substituted or unsubstituted heterocyclic ring system with $Ar^2$.

In general embodiments, $Ar^2(Z)$ is a proton donor system. It has been found that in binding to and inhibiting NMDA receptors, a proton donor provides additional activity in stabilizing the molecule in the receptor. Any proton donor can be included in this position, however in certain specific embodiments, $Ar^2$ is a 5 or 6 membered aromatic, heteroaromatic or heterocyclic ring, Z is selected from OH, $NR^6R^7$, $NR^8SO_2$($C_1$-$C_6$ alkyl), $NR^8C(O)NR^6R^7$, $NR^8C(S)NR^6R^7$, $NR^8CHO$, $NR^8C(O)$($C_1$-$C_6$ alkyl), $NR^8C(O)O$($C_1$-$C_6$ alkyl), $NR^8$-dihydrothiazole, or $NR^8$-dihydroimidazole wherein each $R^6$, $R^7$ and $R^8$ is independently H, $C_1$-$C_6$ alkyl or $C_6$-$C_{12}$ aralkyl. In specific embodiments, Z is selected from OH, $NHSO_2CH_3$ and NHCONHR wherein R is as defined above.

In one embodiment, Z is OH, $NR^6R^7$, $NR^8SO_2$($C_1$-$C_6$ alkyl), $NR^8C(O)NR^6R^7$, $NR^8C(S)NR^6R^7$, $NR^8C(O)O$($C_1$-$C_6$ alkyl), $NR^8$-dihydrothiazole, or $NR^8$-dihydroimidazole. In certain embodiments, Z is OH, $NR^8SO_2$($C_1$-$C_6$ alkyl) or $NR^8C(O)NR^6R^7$, for example $NHSO_2$($C_1$-$C_6$ alkyl) or NHC(O)NHR. In one embodiment, Z is $NR^8C(O)NR^6R^7$, for example $NHC(O)NH_2$ or $NHC(O)N(CH_3)_2$.

In some embodiments, R is H. In other embodiments, R is $C_{1-4}$ alkyl, for example methyl, ethyl, propyl or butyl. In certain embodiment, R is methyl. In one embodiment, one or more R is an OH group which creates a stereogenic center. In another embodiment, the OH group is in the R configuration. In another embodiment, the OH group is in the S configuration.

In certain embodiments, Z comes together with $Ar^2$ to form a heterocyclic ring

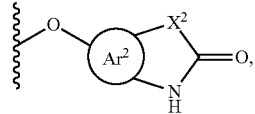

for example

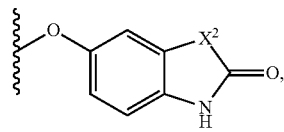

wherein $X^2$ is —O—, —S—, —N(H)—, —N(R)—, —NH—$CH_2$—, —N=CH—, —NR—$CH_2$—, —$CH_2$—N(H)—, —$CH_2$—N(R)—, —$CH_2$—, —$CH_2$—$CH_2$—, —CH=CH—, —CR—$CH_2$—, or —CR=CH—.

In certain embodiments, Z comes together with $Ar^2$ to form a heterocyclic ring selected from:

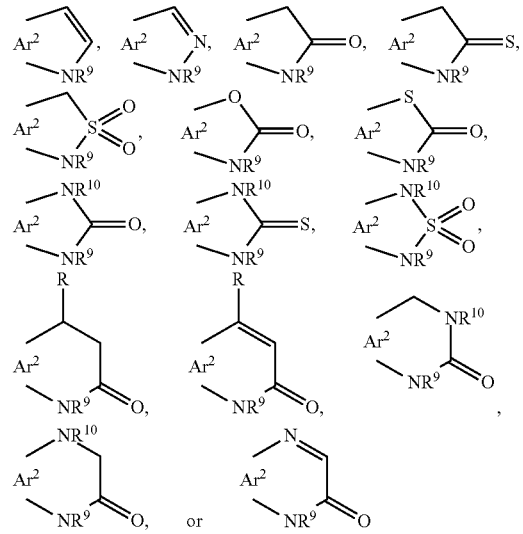

wherein $R^9$ and $R^{10}$ are each independently H, $C_1$-$C_6$ alkyl or aralkyl.

In certain embodiments, Z comes together with $Ar^2$ to form a heterocyclic ring selected from

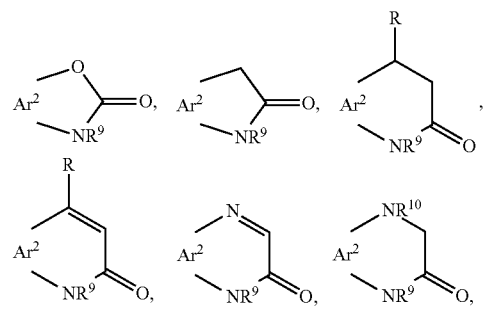

-continued

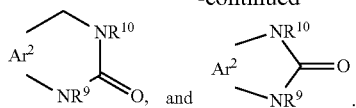

In certain embodiments, Z comes together with $Ar^2$ to form a heterocyclic ring selected from

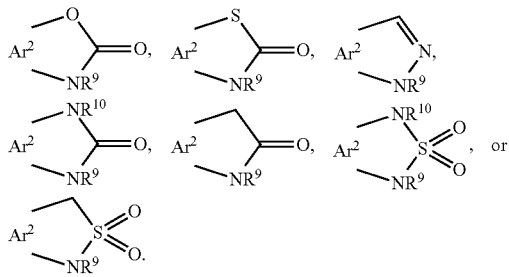

In one embodiment, Z comes together with $Ar^2$ to form

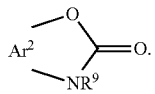

In one embodiment, Z comes together with $Ar^2$ to form a heterocyclic ring selected from

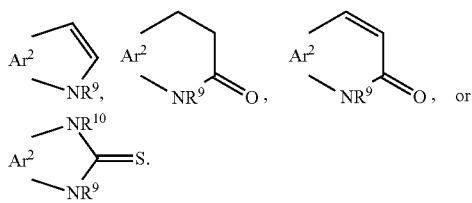

In one embodiment, $R^9$ and $R^{10}$ are each H.

In another embodiment, Z and $Ar^2$ are taken together and selected from the group consisting of:

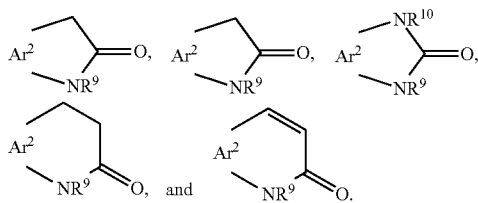

In typical embodiments, $Ar^1$ is a 3 to 7 membered aryl, heteroaryl or heterocycle. In one embodiment, $Ar^1$ is substituted with small groups or less bulky groups, for example chloro, fluoro, methyl, or trifluoromethyl. In typical embodiments, $Ar^1$ is a six membered, substituted or unsubstituted aryl, heteroaryl or heterocycle. In one embodiment $Ar^1$ is aryl, for example phenyl. In one embodiment $Ar^2$ is aryl, for example phenyl. In certain embodiments, both $Ar^1$ and $Ar^2$ are aryl. In a particular embodiment, both $Ar^1$ and $Ar^2$ are phenyl. In other embodiments, $Ar^1$ is heteroaryl or heterocycle. In another embodiment, $Ar^2$ is heteroaryl or heterocycle. In one embodiment, $Ar^2$ is substituted with a Z group at the 4 position.

In one embodiment, A is a bond. In a particular embodiment, A is not a bond. In another embodiment, A is $CH_2$, $CH=CH$, $C\equiv C$, NR, O or S. In one embodiment, A is $CH_2$. In one embodiment, A is $CH=CH$. In another embodiment, A is $C\equiv C$. In another embodiment, A is NR. In another embodiment, A is O. In another embodiment, A is S.

In one embodiment, m is 0. In one embodiment, n is 1. In another embodiment, n is 2.

In a particular embodiment, m is 0 and X is $CH=CH$, NH or $CH_2$. In another particular embodiment, m is 1 and X is O or NH. In another embodiment, m is 0 or 1 and X is O, $CH=CH$, NH or $CH_2$.

In one embodiment, n is 0. In one embodiment, n is 1. In another embodiment, n is 2.

In one embodiment, p is 0. In one embodiment, p is 1. In another embodiment, p is 2.

In certain embodiments, both n and p are 0. It has been found that a four membered ring system at this position provides highly active compounds at all pH levels. In other embodiments, n is 1 and p is 0. In other embodiments, n is 0 and p is 1. In certain embodiments, both n and p are 1. It has been found that a six membered ring system in this position provides strong pH dependence with high activity at pH below 7.0 and reduced activity at higher pH. In other embodiments, n is 1 and p is 2. In another embodiment, n is 2 and p is 1. In one embodiment, both n and p are 2.

In certain embodiments, A is O. In certain other embodiments, A is NR and in particular NH. In specific embodiments, A is NR and m is 0 or 1. In more specific embodiments, A is NR and m is 0. In certain embodiments, A is not a bond when m is 0.

In one embodiment, the compounds are of Formula I-a:

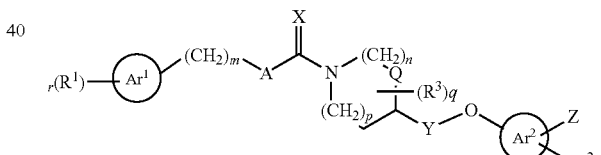

In which $Ar^1$, $Ar^2$, m, n, p, A, X, Q, Y and Z are as defined above, each $R^1$ is independently selected from $C_1$-$C_6$ alkyl, $C_3$-$C_6$ cycloalkyl, $C_1$-$C_6$ haloalkyl, —OH, O-alkyl, O-aryl, —SH, —S-alkyl, fluoro, chloro, bromo, iodo, nitro, or cyano; or two $R^1$ may be taken together with $Ar^1$ to form a bicyclic ring system;

each $R^2$ and $R^3$ is independently selected from $C_1$-$C_6$ alkyl, $C_3$-$C_6$ cycloalkyl, $C_1$-$C_6$ haloalkyl, —OH, O-alkyl, O-aryl, —SH, —S-alkyl, fluoro, chloro, bromo, iodo, nitro, or cyano;

r is independently selected from 0, 1, 2, 3, 4 or 5; and s is independently selected from 0, 1, 2, 3, 4 or 5.

In certain embodiment, each $R^1$ is independently selected from $C_1$-$C_4$ alkyl, $C_1$-$C_4$ alkoxy, C(=O)—($C_1$-$C_4$)-alkyl, $C_1$-$C_6$ haloalkyl, hydroxy, fluoro, chloro, bromo, iodo, nitro, or cyano. In a particular embodiment, $R^1$ is fluoro, chloro, bromo, iodo, or $C_1$-$C_6$ haloalkyl. In a further embodiment, $R^1$ is methyl, trifluoromethyl, methoxy, nitro, fluoro, chloro or hydroxy. In some embodiments, or two $R^1$ may be taken together with $Ar^1$ to form a dioxolane ring or a cyclobutane ring. In some embodiments, $R^1$ is alkyl, cycloalkyl, halide, alkoxy, thioalkoxy, cyano, haloalkyl, trifluoromethyl, trifluoroethyl.

In one further embodiment, there are one, two or three $R^1$ groups substituting $Ar^1$. In one embodiment, $Ar^1$ is substituted with one fluoro group. In one embodiment, $Ar^1$ is substituted with two fluoro groups. In one embodiment, $Ar^1$ is substituted with one fluoro group and one chloro group. In one embodiment, $Ar^1$ is substituted with one chloro group. In one embodiment, $Ar^1$ is substituted with two chloro groups. In one embodiment, $Ar^1$ is substituted with one methyl group. In one embodiment, $Ar^1$ is substituted with one trifluoromethyl group.

In certain embodiment, each $R^2$ is independently selected from $C_1$-$C_4$ alkyl, $C_1$-$C_4$ alkoxy, $C(=O)$—$(C_1$-$C_4)$-alkyl, $C_1$-$C_6$ haloalkyl, hydroxy, fluoro, chloro, bromo, iodo, nitro, or cyano. In a particular embodiment, $R^2$ is fluoro, chloro, bromo, iodo, or $C_1$-$C_6$ haloalkyl. In a further embodiment, $R^2$ is methyl, trifluoromethyl, methoxy, nitro, fluoro, chloro or hydroxyl.

In certain embodiment, each $R^3$ is independently selected from $C_1$-$C_4$ alkyl, $C_1$-$C_4$ alkoxy, $C(=O)$—$(C_1$-$C_4)$-alkyl, $C_1$-$C_6$ haloalkyl, hydroxy, fluoro, chloro, bromo, iodo, nitro, or cyano. In a particular embodiment, $R^3$ is fluoro, chloro, bromo, iodo, or $C_1$-$C_6$ haloalkyl. In a further embodiment, $R^3$ is methyl, trifluoromethyl, methoxy, nitro, fluoro, chloro or hydroxyl.

In one embodiment, r is 0. In one embodiment, r is 1. In one embodiment, r is 2. In one embodiment, r is 3. In one embodiment, r is 4. In one embodiment, r is 5. In one embodiment, r is 0, 1, 2 or 3.

In one embodiment, s is 0. In one embodiment, s is 1. In one embodiment, s is 2. In one embodiment, s is 3. In one embodiment, s is 4. In one embodiment, s is 5. In one embodiment, s is 0, 1, 2 or 3.

In one embodiment, $Ar^1$ is phenyl. In one embodiment, $Ar^1$ is phenyl and is substituted with an $R^1$ group at the 2, 3, or 4 position. In another embodiment, $Ar^1$ is phenyl and is substituted with $R^1$ groups at the 2 and 4 positions. In another embodiment, $Ar^1$ is phenyl and is substituted with $R^1$ groups at the 3 and 4 positions. In one embodiment, $Ar^1$ is imidazolyl. In one embodiment, $Ar^1$ is pyridyl. In another subembodiment, $Ar^1$ is 2-pyridyl, 3-pyridyl, or 4-pyridyl.

In some embodiments, the compounds are of Formula I-b

Formula I-b

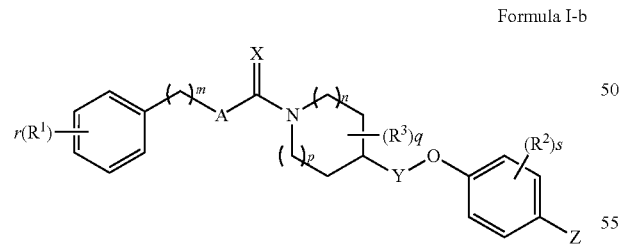

wherein each of $R^1$, $R^2$, $R^3$, m, n, p, q, r, s, A, X, and Y are as defined herein; and Z is OH, $NR^6R^7$, $NR^8SO_2(C_1$-$C_6$ alkyl), $NR^8C(O)NR^6R^7$, $NR^8C(S)NR^6R^7$, $NR^8CHO$, $NR^8C(O)(C_1$-$C_6$ alkyl), $NR^8C(O)O(C_1$-$C_6$ alkyl), $NR^8$-dihydrothiazole, or $NR^8$-dihydroimidazole wherein each $R^6$, $R^7$ and $R^8$ is independently H, $C_1$-$C_6$ alkyl or $C_6$-$C_{12}$ aralkyl or Z comes together with the phenyl moiety to which it is attached to form a substituted or unsubstituted heterocyclic ring system with the phenyl moiety.

In general embodiments, phenyl(Z) is a proton donor system. In specific embodiments, Z is selected from OH, $NHSO_2CH_3$ and NHCONHR wherein R is as defined above.

In one embodiment, Z is OH, $NR^6R^7$, $NR^8SO_2(C_1$-$C_6$ alkyl), $NR^8C(O)NR^6R^7$, $NR^8C(S)NR^6R^7$, $NR^8C(O)O(C_1$-$C_6$ alkyl), $NR^8$-dihydrothiazole, or $NR^8$-dihydroimidazole. In certain embodiments, Z is OH, $NR^8SO_2(C_1$-$C_6$ alkyl) or $NR^8C(O)NR^6R^7$, for example $NHSO_2(C_1$-$C_6$ alkyl) or NHC(O)NHR. In one embodiment, Z is $NR^8C(O)NR^6R^7$, for example $NHC(O)NH_2$ or $NHC(O)N(CH_3)_2$.

In some embodiments, R is H. In other embodiments, R is $C_{1-4}$ alkyl, for example methyl, ethyl, propyl or butyl. In certain embodiment, R is methyl. In one embodiment, one or more R is an OH group which creates a stereogenic center. In another embodiment, the OH group is in the R configuration. In another embodiment, the OH group is in the S configuration.

In certain embodiments, Z comes together with the phenyl moiety to which it is attached to form the heterocyclic ring

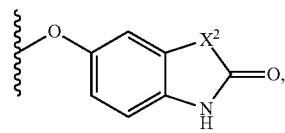

wherein $X^2$ is —O—, —S—, —N(H)—, —N(R)—, —NH—$CH_2$—, —N=CH—, —NR—$CH_2$—, —$CH_2$—N(H)—, —$CH_2$—N(R)—, —$CH_2$—, —$CH_2$—$CH_2$—, —CH=CH—, —CR—$CH_2$—, or —CR=CH—.

In certain embodiments, Z comes together with the phenyl moiety to which it is attached to form a heterocyclic ring selected from:

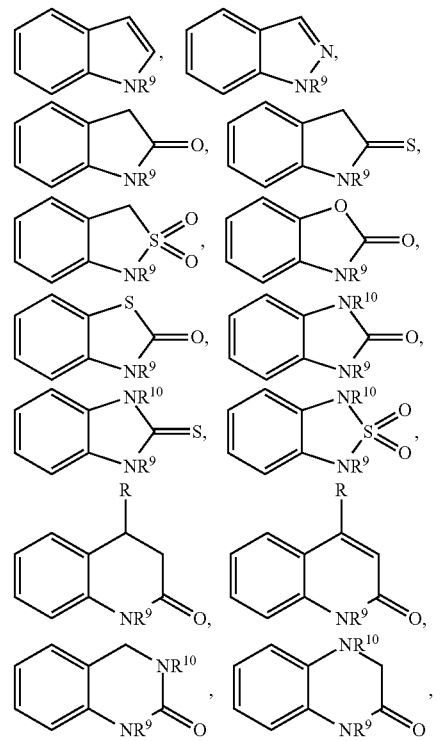

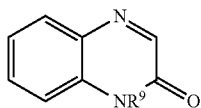

wherein $R^9$ and $R^{10}$ are each independently H, $C_1$-$C_6$ alkyl or aralkyl.

In certain embodiments, Z comes together with the phenyl moiety to form a heterocyclic ring selected from

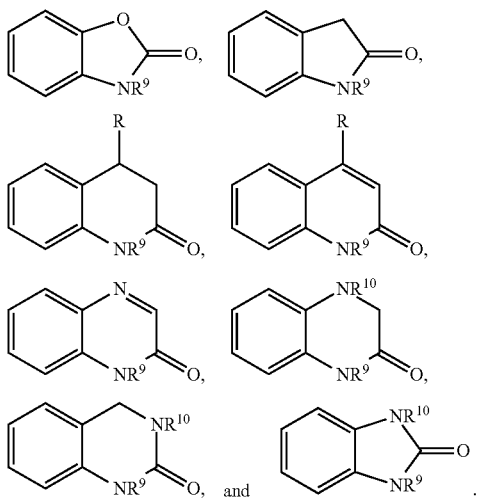

In certain embodiments, Z comes together with the phenyl moiety to form a heterocyclic ring selected from

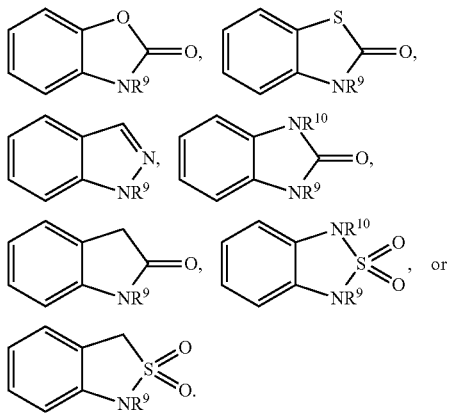

In one embodiment, Z comes together with the phenyl moiety to form

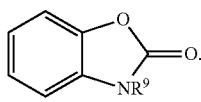

In one embodiment, Z comes together with the phenyl moiety to form a heterocyclic ring selected from

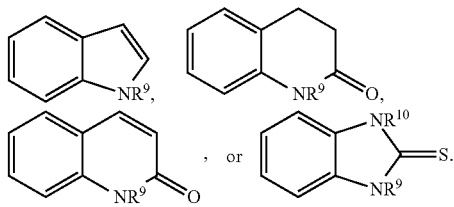

In one embodiment, $R^9$ and $R^{10}$ are each H.

In another embodiment, Z and the phenyl moiety are taken together and selected from the group consisting of:

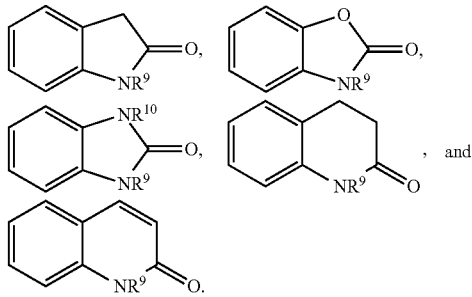

In one embodiment, the phenyl moiety on the left side of Formula I-b is substituted with small groups or less bulky groups, for example chloro, fluoro, methyl, or trifluoromethyl.

In some embodiments, the compounds are of Formula I-c:

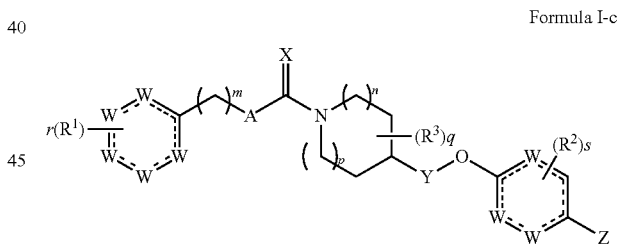

Formula I-c wherein each of $R^1$, $R^2$, $R^3$, m, n, p, q, r, s, A, X and Y are as defined herein;

wherein each W is independently CH, $CH_2$, O, N, S, NH, NR, CR or $CR_2$; and wherein Z is OH, $NR^6R^7$, $NR^8SO_2(C_1$-$C_6$ alkyl), $NR^8C(O)NR^6R^7$, $NR^8C(S)NR^6R^7$, $NR^8CHO$, $NR^8C(O)(C_1$-$C_6$ alkyl), $NR^8C(O)O(C_1$-$C_6$ alkyl), $NR^8$-dihydrothiazole, or $NR^8$-dihydroimidazole wherein each $R^6$, $R^7$ and $R^8$ is independently H, $C_1$-$C_6$ alkyl or $C_6$-$C_{12}$ aralkyl or Z comes together with

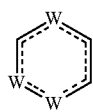

to form a substituted or unsubstituted heterocyclic ring system with

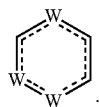

In general embodiments,

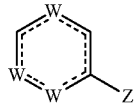

is a proton donor system. In specific embodiments, Z is selected from OH, NHSO$_2$CH$_3$ and NHCONHR wherein R is as defined above.

In one embodiment, Z is OH, NR$^6$R$^7$, NR$^8$SO$_2$(C$_1$-C$_6$ alkyl), NR$^8$C(O)NR$^6$R$^7$, NR$^8$C(S)NR$^6$R$^7$, NR$^8$C(O)O(C$_1$-C$_6$ alkyl), NR$^8$-dihydrothiazole, or NR$^8$-dihydroimidazole. In certain embodiments, Z is OH, NR$^8$SO$_2$(C$_1$-C$_6$ alkyl) or NR$^8$C(O)NR$^6$R$^7$, for example NHSO$_2$(C$_1$-C$_6$ alkyl) or NHC(O)NHR. In one embodiment, Z is NR$^8$C(O)NR$^6$R$^7$, for example NHC(O)NH$_2$ or NHC(O)N(CH$_3$)$_2$.

In some embodiments, R is H. In other embodiments, R is C$_{1-4}$ alkyl, for example methyl, ethyl, propyl or butyl. In certain embodiment, R is methyl. In one embodiment, one or more R is an OH group which creates a stereogenic center. In another embodiment, the OH group is in the R configuration. In another embodiment, the OH group is in the S configuration.

In certain embodiments, Z comes together with

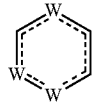

to form the heterocyclic ring

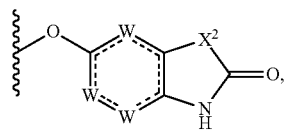

wherein X$^2$ is —O—, —S—, —N(H)—, —N(R)—, —NH—CH$_2$—, —N=CH—, —NR—CH$_2$—, —CH$_2$—N(H)—, —CH$_2$—N(R)—, —CH$_2$—, —CH$_2$—CH$_2$—, —CH=CH—, —CR—CH$_2$—, or —CR=CH—.

In certain embodiments, Z comes together with

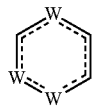

to form a heterocyclic ring selected from:

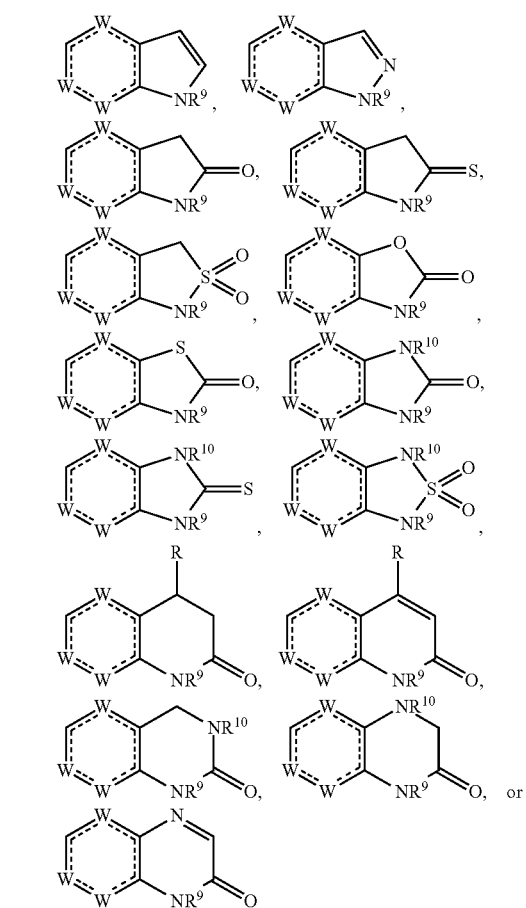

wherein R$^9$ and R$^{10}$ are each independently H, C$_1$-C$_6$ alkyl or aralkyl.

In certain embodiments, Z comes together with

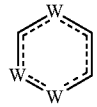

to form a heterocyclic ring selected from

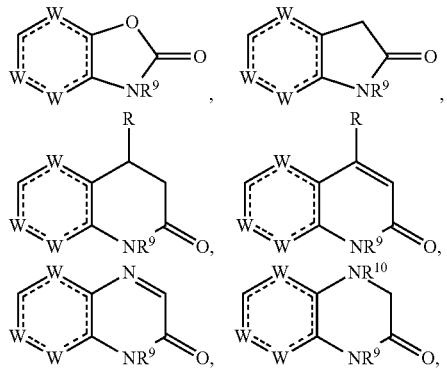

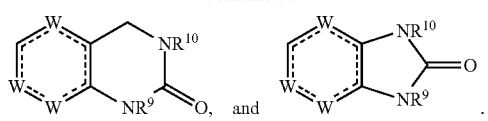

In certain embodiments, Z comes together with

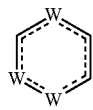

to form a heterocyclic ring selected from

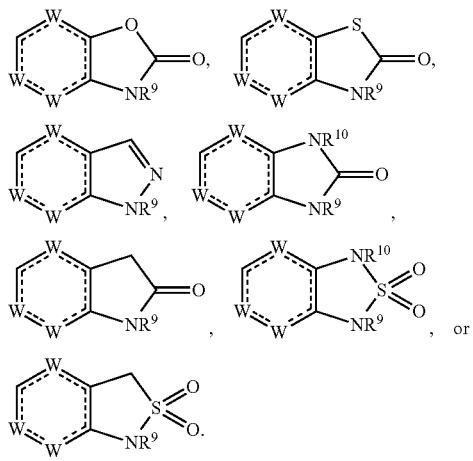

In one embodiment, Z comes together with

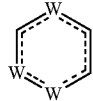

to form

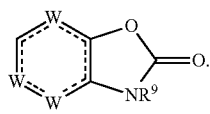

In one embodiment, Z comes together with

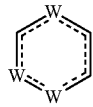

to form a heterocyclic ring selected from

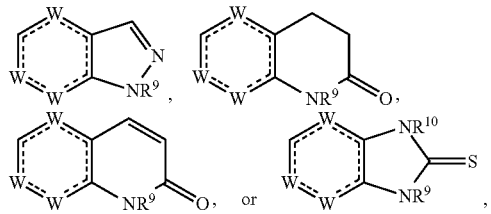

In one embodiment, $R^9$ and $R^{10}$ are each H.

In another embodiment, Z and

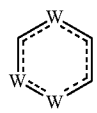

are taken together and selected from the group consisting of:

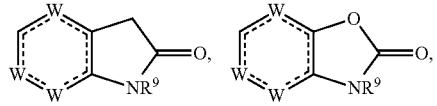

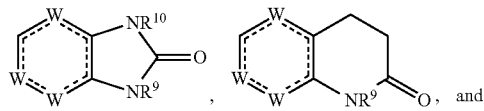

In one embodiment,

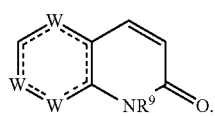

of Formula I-c is substituted with small groups or less bulky groups, for example chloro, fluoro, methyl, or trifluoromethyl.

In any of the Formulae provided herein, bonds indicated in the structure as ==== can each be either single or double bonds with the proviso that adjacent ==== bonds cannot both be double bonds. For any W group that forms part of a bond indicated as ====, only W groups of the appropriate valence are included. It will be readily understood by those of skill in the art which structures are encompassed by the structures provided herein.

In one embodiment, W is a divalent group. In another embodiment, W is a trivalent group.

In further embodiments, the compounds are of Formula I-d:

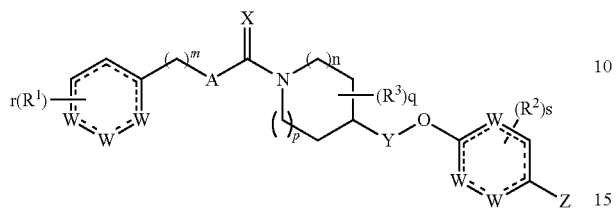

Formula I-d wherein each of $R^1$, $R^2$, $R^3$, m, n, p, q, r, s, A, X, and Y are as defined herein;
wherein each W is independently CH, $CH_2$, O, N, S, NH, NR, CR or $CR_2$; and
wherein Z is OH, $NR^6R^7$, $NR^8SO_2(C_1$-$C_6$ alkyl), $NR^8C(O)NR^6R^7$, $NR^8C(S)NR^6R^7$, $NR^8CHO$, $NR^8C(O)(C_1$-$C_6$ alkyl), $NR^8C(O)O(C_1$-$C_6$ alkyl), $NR^8$-dihydrothiazole, or $NR^8$-dihydroimidazole wherein each $R^6$, $R^2$ and $R^8$ is independently H, $C_1$-$C_6$ alkyl or $C_6$-$C_{12}$ aralkyl or Z comes together with

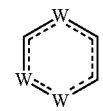

to form a substituted or unsubstituted heterocyclic ring system with

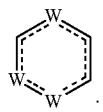

In general embodiments,

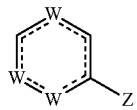

is a proton donor system. In specific embodiments, Z is selected from OH, $NHSO_2CH_3$ and NHCONHR wherein R is as defined above.

In one embodiment, Z is OH, $NR^6R^7$, $NR^8SO_2(C_1$-$C_6$ alkyl), $NR^8C(O)NR^6R^7$, $NR^8C(S)NR^6R^7$, $NR^8C(O)O(C_1$-$C_6$ alkyl), $NR^8$-dihydrothiazole, or $NR^8$-dihydroimidazole. In certain embodiments, Z is OH, $NR^8SO_2(C_1$-$C_6$ alkyl) or $NR^8C(O)NR^6R^7$, for example $NHSO_2(C_1$-$C_6$ alkyl) or NHC(O)NHR. In one embodiment, Z is $NR^8C(O)NR^6R^7$, for example $NHC(O)NH_2$ or $NHC(O)N(CH_3)_2$.

In some embodiments, R is H. In other embodiments, R is $C_{1-4}$ alkyl, for example methyl, ethyl, propyl or butyl. In certain embodiment, R is methyl. In one embodiment, one or more R is an OH group which creates a stereogenic center. In another embodiment, the OH group is in the R configuration. In another embodiment, the OH group is in the S configuration.

In certain embodiments, Z comes together with

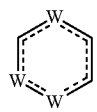

to form the heterocyclic ring

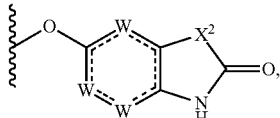

wherein $X^2$ is —O—, —S—, —N(H)—, —N(R)—, —NH—$CH_2$—, —N=CH—, —NR—$CH_2$—, —$CH_2$—N(H)—, —$CH_2$—N(R)—, —$CH_2$—, —$CH_2$—$CH_2$—, —CH=CH—, —CR—$CH_2$—, or —CR=CH—.

In certain embodiments, Z comes together with

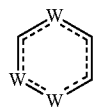

to form a heterocyclic ring selected from:

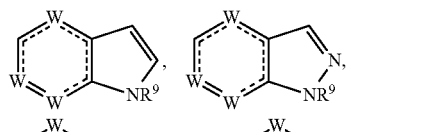

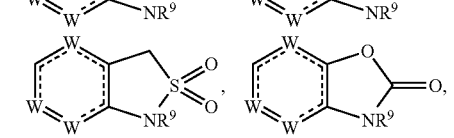

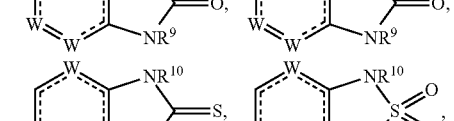

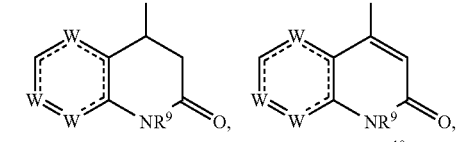

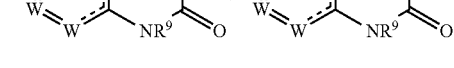, or

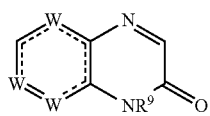

wherein $R^9$ and $R^{10}$ are each independently H, $C_1$-$C_6$ alkyl or aralkyl.

In certain embodiments, Z comes together with

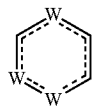

to form a heterocyclic ring selected from

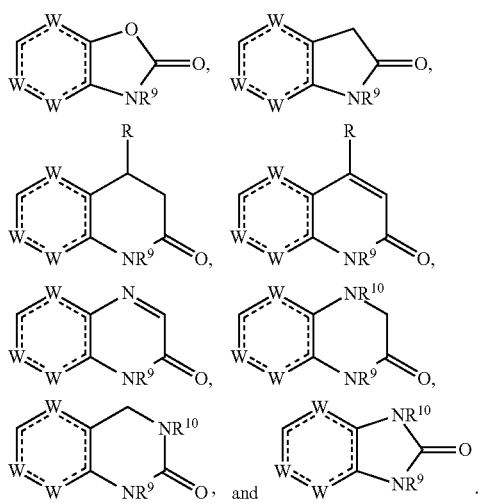

In certain embodiments, Z comes together with

to form a heterocyclic ring selected from

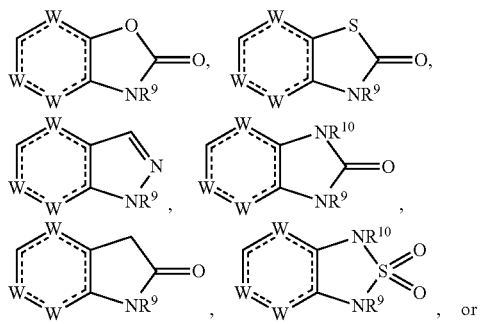

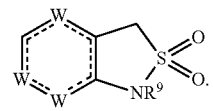

In one embodiment, Z comes together with

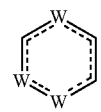

to form

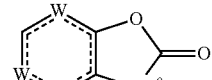

In one embodiment, Z comes together with

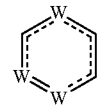

to form a heterocyclic ring selected from

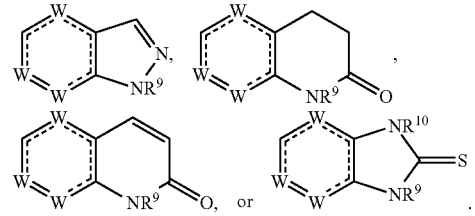

In one embodiment, $R^9$ and $R^{10}$ are each H.

In another embodiment, Z and

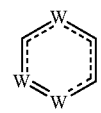

are taken together and selected from the group consisting of:

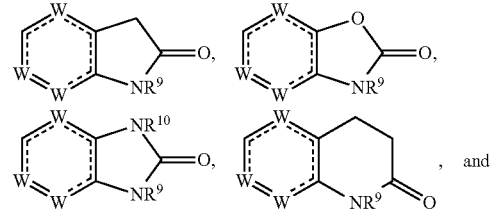

-continued

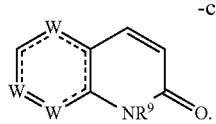

In one embodiment,

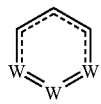

of Formula I-d is substituted with small groups or less bulky groups, for example chloro, fluoro, methyl, or trifluoromethyl.

In certain embodiments, the structure:

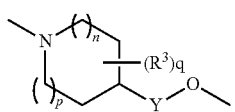

is selected from the group consisting of:

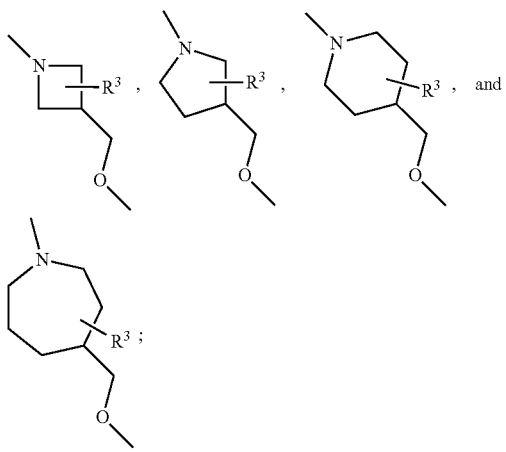

wherein $R^3$ is H, $C_1$-$C_6$ alkyl, or fluoro.

In one embodiment, W is a divalent group. In another embodiment, W is a trivalent group.

In certain embodiments, the compounds are of Formula I-e:

Formula I-e

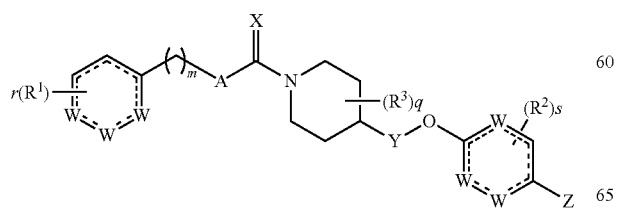

wherein each of $R^1$, $R^2$, $R^3$, m, q, r, s, A, X and Y are as defined herein;

wherein each W is independently CH, $CH_2$, O, N, S, NH, NR, CR or $CR_2$; and wherein Z is OH, $NR^6R^7$, $NR^8SO_2(C_1$-$C_6$ alkyl), $NR^8C(O)NR^6R^7$, $NR^8C(S)NR^6R^7$, $NR^8CHO$, $NR^8C(O)(C_1$-$C_6$ alkyl), $NR^8C(O)O(C_1$-$C_6$ alkyl), $NR^8$-dihydrothiazole, or $NR^8$-dihydroimidazole wherein each $R^6$, $R^2$ and $R^8$ is independently H, $C_1$-$C_6$ alkyl or $C_6$-$C_{12}$ aralkyl or Z comes together with

to form a substituted or unsubstituted heterocyclic ring system with

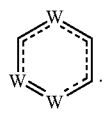

In general embodiments,

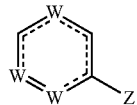

is a proton donor system. In specific embodiments, Z is selected from OH, $NHSO_2CH_3$ and NHCONHR wherein R is as defined above.

In one embodiment, Z is OH, $NR^6R^7$, $NR^8SO_2(C_1$-$C_6$ alkyl), $NR^8C(O)NR^6R^7$, $NR^8C(S)NR^6R^7$, $NR^8C(O)O(C_1$-$C_6$ alkyl), $NR^8$-dihydrothiazole, or $NR^8$-dihydroimidazole. In certain embodiments, Z is OH, $NR^8SO_2(C_1$-$C_6$ alkyl) or $NR^8C(O)NR^6R^7$, for example $NHSO_2(C_1$-$C_6$ alkyl) or NHC(O)NHR. In one embodiment, Z is $NR^8C(O)NR^6R^7$, for example $NHC(O)NH_2$ or $NHC(O)N(CH_3)_2$.

In some embodiments, R is H. In other embodiments, R is $C_{1-4}$ alkyl, for example methyl, ethyl, propyl or butyl. In certain embodiment, R is methyl. In one embodiment, one or more R is an OH group which creates a stereogenic center. In another embodiment, the OH group is in the R configuration. In another embodiment, the OH group is in the S configuration.

In certain embodiments, Z comes together with

to form the heterocyclic ring

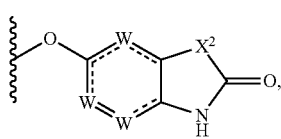

wherein $X^2$ is —O—, —S—, —N(H)—, —N(R)—, —NH—CH$_2$—, —N=CH—, —NR—CH$_2$—, —CH$_2$—N(H)—, —CH$_2$—N(R)—, —CH$_2$—, —CH$_2$—CH$_2$—, —CH=CH—, —CR—CH$_2$—, or —CR=CH—.

In certain embodiments, Z comes together with

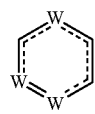

to form a heterocyclic ring selected from:

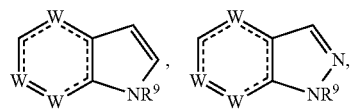

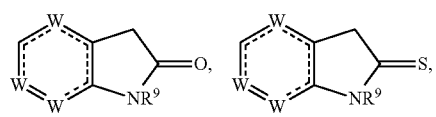

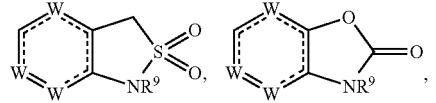

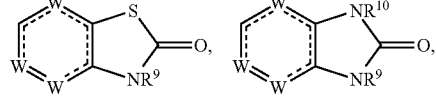

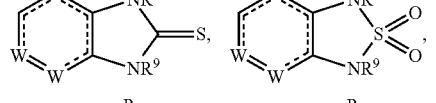

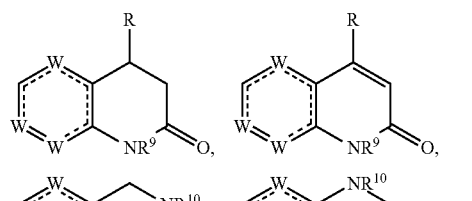

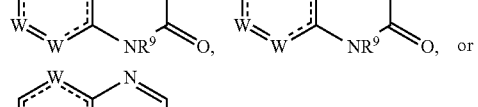

wherein $R^9$ and $R^{10}$ are each independently H, $C_1$-$C_6$ alkyl or aralkyl.

In certain embodiments, Z comes together with

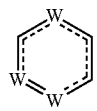

to form a heterocyclic ring selected from

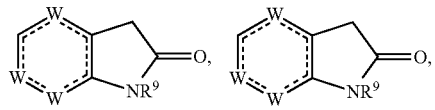

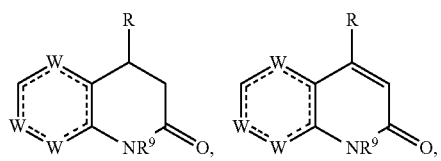

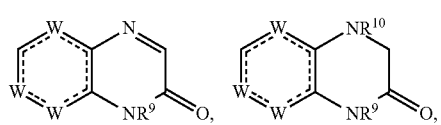

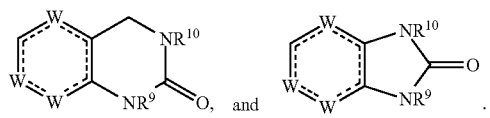

and

In certain embodiments, Z comes together with

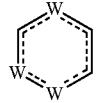

to form a heterocyclic ring selected from

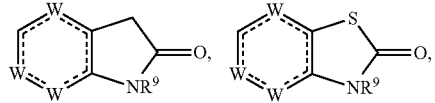

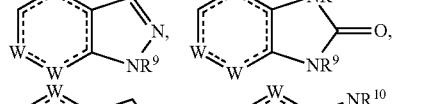

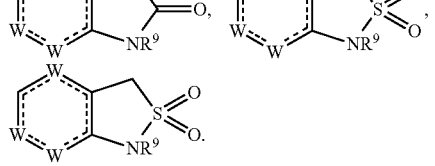

In one embodiment, Z comes together with

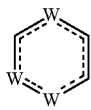

to form

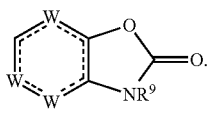

In one embodiment, Z comes together with

to form a heterocyclic ring selected from

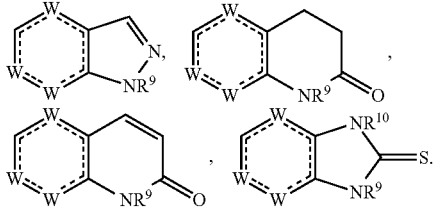

In one embodiment, $R^9$ and $R^{10}$ are each H.

In another embodiment, Z and

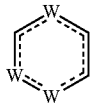

are taken together and selected from the group consisting of:

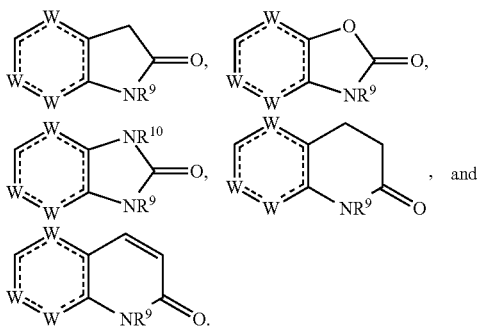

In one embodiment,

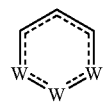

of Formula I-e is substituted with small groups or less bulky groups, for example chloro, fluoro, methyl, or trifluoromethyl.

In further embodiments, the compounds are of Formula I-f:

Formula I-f

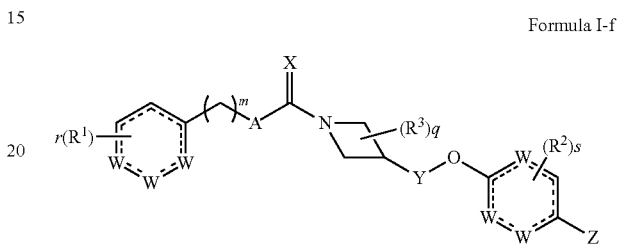

wherein each of $R^1$, $R^2$, $R^3$, m, q, r, s, A, X and Y are as defined herein;

wherein each W is independently CH, $CH_2$, O, N, S, NH, NR, CR or $CR_2$; and wherein Z is OH, $NR^6R^7$, $NR^8SO_2(C_1\text{-}C_6 \text{ alkyl})$, $NR^8C(O)NR^6R^7$, $NR^8C(S)NR^6R^7$, $NR^8CHO$, $NR^8C(O)(C_1\text{-}C_6 \text{ alkyl})$, $NR^8C(O)O(C_1\text{-}C_6 \text{ alkyl})$, $NR^8$-dihydrothiazole, or $NR^8$-dihydroimidazole wherein each $R^6$, $R^2$ and $R^8$ is independently H, $C_1\text{-}C_6$ alkyl or $C_6\text{-}C_{12}$ aralkyl or Z comes together with to form a substituted or unsubstituted heterocyclic ring system with In general embodiments, is a proton donor system. In specific embodiments, Z is selected from OH, $NHSO_2CH_3$ and NHCONHR wherein R is as defined above.

In one embodiment, Z is OH, $NR^6R^7$, $NR^8SO_2(C_1\text{-}C_6 \text{ alkyl})$, $NR^8C(O)NR^6R^7$, $NR^8C(S)NR^6R^7$, $NR^8C(O)O(C_1\text{-}C_6 \text{ alkyl})$, $NR^8$-dihydrothiazole, or $NR^8$-dihydroimidazole. In certain embodiments, Z is OH, $NR^8SO_2(C_1\text{-}C_6 \text{ alkyl})$ or $NR^8C(O)NR^6R^7$, for example $NHSO_2(C_1\text{-}C_6 \text{ alkyl})$ or NHC (O)NHR. In one embodiment, Z is $NR^8C(O)NR^6R^7$, for example $NHC(O)NH_2$ or $NHC(O)N(CH_3)_2$.

In some embodiments, R is H. In other embodiments, R is $C_{1-4}$ alkyl, for example methyl, ethyl, propyl or butyl. In certain embodiment, R is methyl. In one embodiment, one or more R is an OH group which creates a stereogenic center. In another embodiment, the OH group is in the R configuration. In another embodiment, the OH group is in the S configuration.

In certain embodiments, Z comes together with

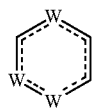

to form the heterocyclic ring

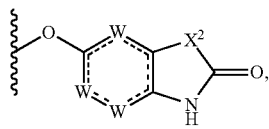

wherein $X^2$ is —O—, —S—, —N(H)—, —N(R)—, —NH—$CH_2$—, —N=CH—, —NR—$CH_2$—, —$CH_2$—N(H)—, —$CH_2$—N(R)—, —$CH_2$—, —$CH_2$—$CH_2$—, —CH=CH—, —CR—$CH_2$—, or —CR=CH—.

In certain embodiments, Z comes together with

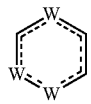

to form a heterocyclic ring selected from:

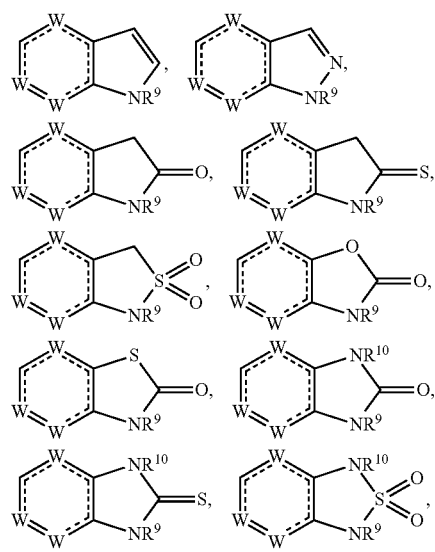

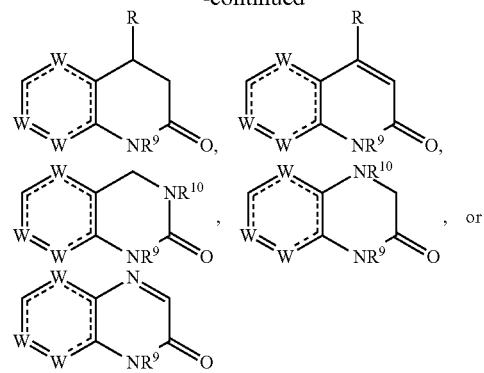

wherein $R^9$ and $R^{10}$ are each independently H, $C_1$-$C_6$ alkyl or aralkyl.

In certain embodiments, Z comes together with

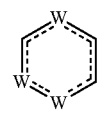

to form a heterocyclic ring selected from

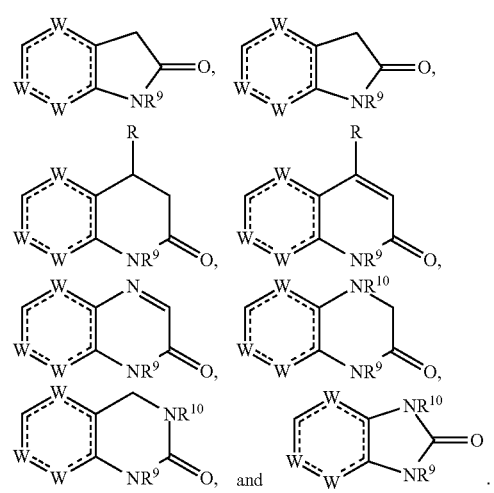

In certain embodiments, Z comes together with

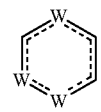

to form a heterocyclic ring selected from

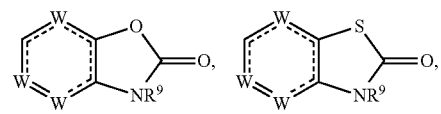

-continued

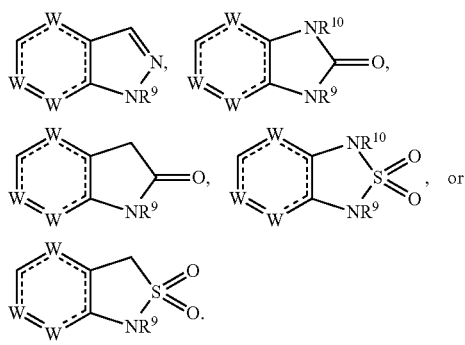

In one embodiment, Z comes together with

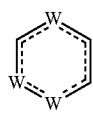

to form

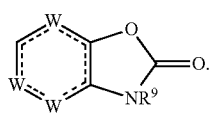

In one embodiment, Z comes together with

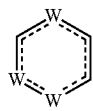

to form a heterocyclic ring selected from

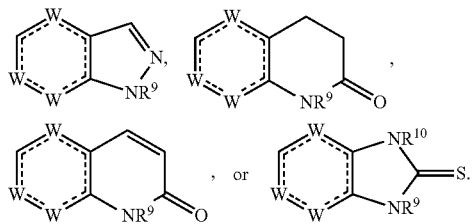

In one embodiment, $R^9$ and $R^{10}$ are each H.

In another embodiment, Z and

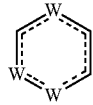

are taken together and selected from the group consisting of:

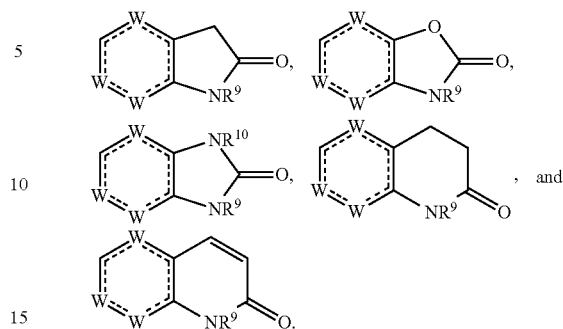

In one embodiment,

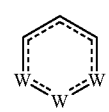

of Formula I-f is substituted with small groups or less bulky groups, for example chloro, fluoro, methyl, or trifluoromethyl.

In particular embodiments, all W groups in any formula provided herein are selected from the group consisting CH, $CH_2$, N, NH, NR, CR and $CR_2$. In certain embodiments, in at least one ring of any of Formulas I-c, I-d, I-e, and I-f, at least one W is N, NH or NR. In certain embodiments of any of Formulas I-c, I-d, I-e, and I-f, at least one W in each ring is N, NH or NR.

In some embodiments, the compounds are of Formula I-g:

Formula I-g

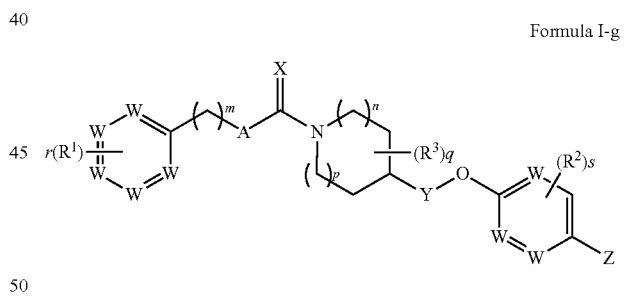

wherein each of $R^1$, $R^2$, $R^3$, m, n, p, q, r, s, A, X and Y are as defined herein;

wherein each W is independently CH, CR or N; and wherein Z is OH, $NR^6R^7$, $NR^8SO_2(C_1$-$C_6$ alkyl), $NR^8C(O)NR^6R^7$, $NR^8C(S)NR^6R^7$, $NR^8CHO$, $NR^8C(O)(C_1$-$C_6$ alkyl), $NR^8C(O)O(C_1$-$C_6$ alkyl), $NR^8$-dihydrothiazole, or $NR^8$-dihydroimidazole wherein each $R^6$, $R^2$ and $R^8$ is independently H, $C_1$-$C_6$ alkyl or $C_6$-$C_{12}$ aralkyl or Z comes together with

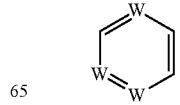

to form a substituted or unsubstituted heterocyclic ring system with

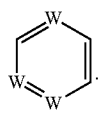

In general embodiments,

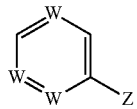

is a proton donor system. In specific embodiments, Z is selected from OH, NHSO$_2$CH$_3$ and NHCONHR wherein R is as defined above.

In one embodiment, Z is OH, NR$^6$R$^7$, NR$^8$SO$_2$(C$_1$-C$_6$ alkyl), NR$^8$C(O)NR$^6$R$^7$, NR$^8$C(S)NR$^6$R$^7$, NR$^8$C(O)O(C$_1$-C$_6$ alkyl), NR$^8$-dihydrothiazole, or NR$^8$-dihydroimidazole. In certain embodiments, Z is OH, NR$^8$SO$_2$(C$_1$-C$_6$ alkyl) or NR$^8$C(O)NR$^6$R$^7$, for example NHSO$_2$(C$_1$-C$_6$ alkyl) or NHC(O)NHR. In one embodiment, Z is NR$^8$C(O)NR$^6$R$^7$, for example NHC(O)NH$_2$ or NHC(O)N(CH$_3$)$_2$.

In some embodiments, R is H. In other embodiments, R is C$_{1-4}$ alkyl, for example methyl, ethyl, propyl or butyl. In certain embodiment, R is methyl. In one embodiment, one or more R is an OH group which creates a stereogenic center. In another embodiment, the OH group is in the R configuration. In another embodiment, the OH group is in the S configuration.

In certain embodiments, Z comes together with

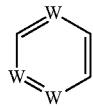

to form the heterocyclic ring

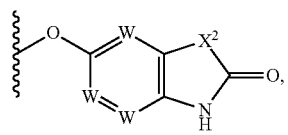

wherein X$^2$ is —O—, —S—, —N(H)—, —N(R)—, —NH—CH$_2$—, —N=CH—, —NR—CH$_2$—, —CH$_2$—N(H)—, —CH$_2$—N(R)—, —CH$_2$—, —CH$_2$—CH$_2$—, —CH=CH—, —CR—CH$_2$—, or —CR=CH—.

In certain embodiments, Z comes together with

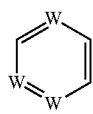

to form a heterocyclic ring selected from:

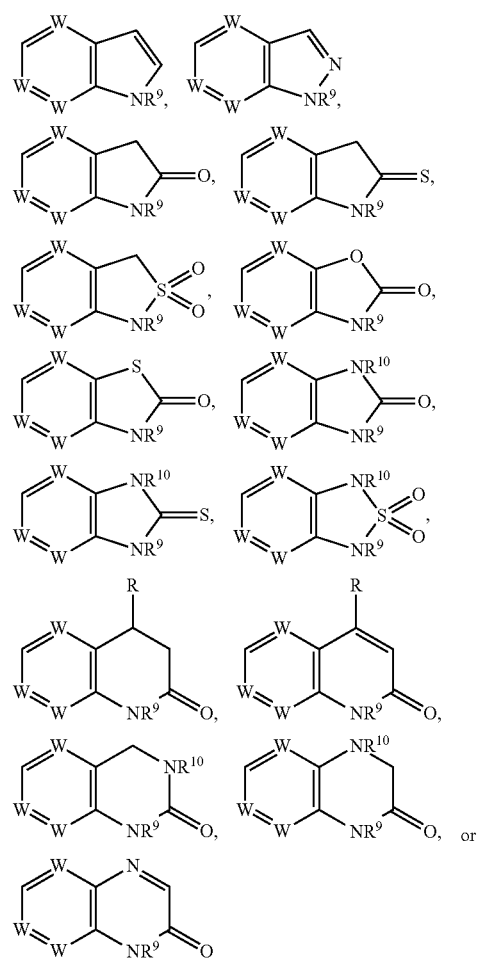

wherein R$^9$ and R$^{10}$ are each independently H, C$_1$-C$_6$ alkyl or aralkyl.

In certain embodiments, Z comes together with

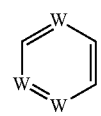

to form a heterocyclic ring selected from

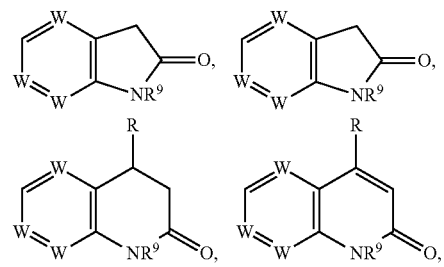

-continued

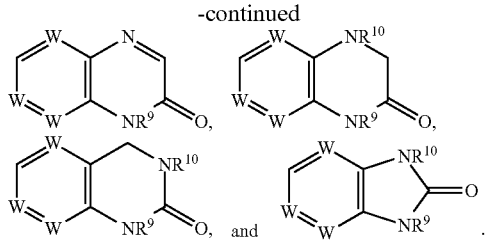

In certain embodiments, Z comes together with

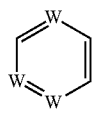

to form a heterocyclic ring selected from

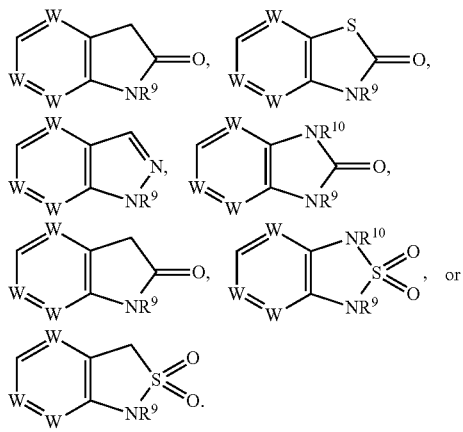

In one embodiment, Z comes together with

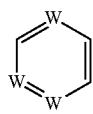

to form

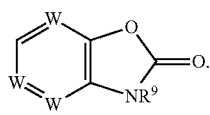

In one embodiment, Z comes together with

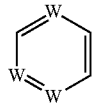

to form a heterocyclic ring selected from

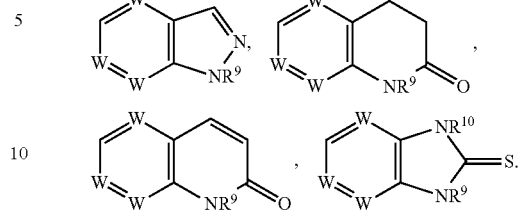

In one embodiment, $R^9$ and $R^{10}$ are each H.

In another embodiment, Z and

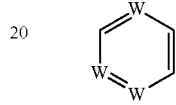

are taken together and selected from the group consisting of:

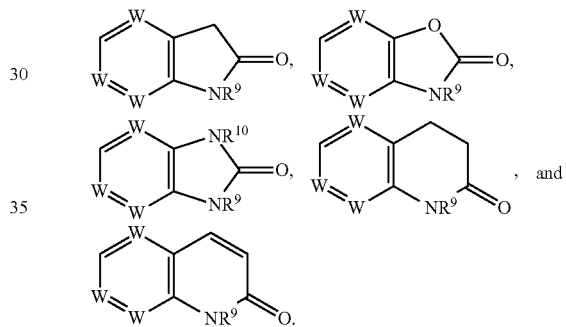

In one embodiment,

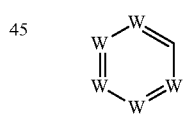

of Formula I-g is substituted with small groups or less bulky groups, for example chloro, fluoro, methyl, or trifluoromethyl.

In other embodiments, the compounds are of Formula I-h:

Formula I-h

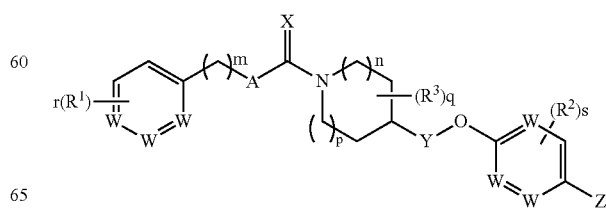

wherein each of $R^1$, $R^2$, $R^3$, m, n, p, q, r, s, A, X and Y are as defined herein;

wherein each W is independently CH, CR or N; and wherein Z is OH, $NR^6R^7$, $NR^8SO_2(C_1$-$C_6$ alkyl), $NR^8C(O)NR^6R^7$, $NR^8C(S)NR^6R^7$, $NR^8CHO$, $NR^8C(O)(C_1$-$C_6$ alkyl), $NR^8C(O)O(C_1$-$C_6$ alkyl), $NR^8$-dihydrothiazole, or $NR^8$-dihydroimidazole wherein each $R^6$, $R^7$ and $R^8$ is independently H, $C_1$-$C_6$ alkyl or $C_6$-$C_{12}$ aralkyl or Z comes together with

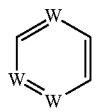

to form a substituted or unsubstituted heterocyclic ring system with

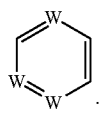

In general embodiments,

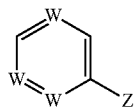

is a proton donor system. In specific embodiments, Z is selected from OH, $NHSO_2CH_3$ and NHCONHR wherein R is as defined above.

In one embodiment, Z is OH, $NR^6R^7$, $NR^8SO_2(C_1$-$C_6$ alkyl), $NR^8C(O)NR^6R^7$, $NR^8C(S)NR^6R^7$, $NR^8C(O)O(C_1$-$C_6$ alkyl), $NR^8$-dihydrothiazole, or $NR^8$-dihydroimidazole. In certain embodiments, Z is OH, $NR^8SO_2(C_1$-$C_6$ alkyl) or $NR^8C(O)NR^6R^7$, for example $NHSO_2(C_1$-$C_6$ alkyl) or NHC(O)NHR. In one embodiment, Z is $NR^8C(O)NR^6R^7$, for example $NHC(O)NH_2$ or $NHC(O)N(CH_3)_2$.

In some embodiments, R is H. In other embodiments, R is $C_{1-4}$ alkyl, for example methyl, ethyl, propyl or butyl. In certain embodiment, R is methyl. In one embodiment, one or more R is an OH group which creates a stereogenic center. In another embodiment, the OH group is in the R configuration. In another embodiment, the OH group is in the S configuration.

In certain embodiments, Z comes together with

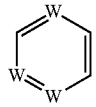

to form the heterocyclic ring

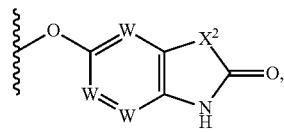

wherein $X^2$ is —O—, —S—, —N(H)—, —N(R)—, —NH—$CH_2$—, —N=CH—, —NR—$CH_2$—, —$CH_2$—N(H)—, —$CH_2$—N(R)—, —$CH_2$—, —$CH_2$—$CH_2$—, —CH=CH—, —CR—$CH_2$—, or —CR=CH—.

In certain embodiments, Z comes together with

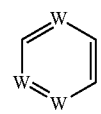

to form a heterocyclic ring selected from:

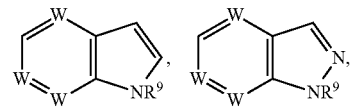

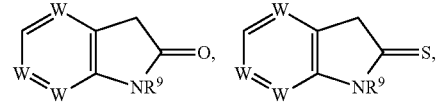

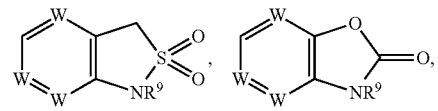

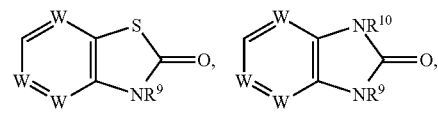

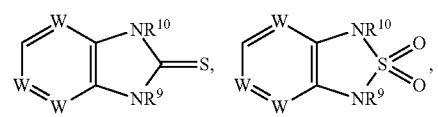

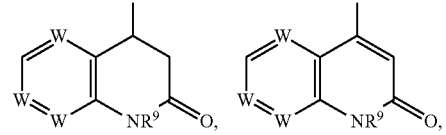

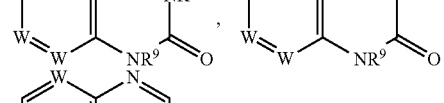

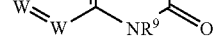, or wherein $R^9$ and $R^{10}$ are each independently H, $C_1$-$C_6$ alkyl or aralkyl.

In certain embodiments, Z comes together with

to form a heterocyclic ring selected from

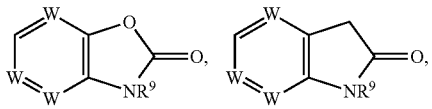

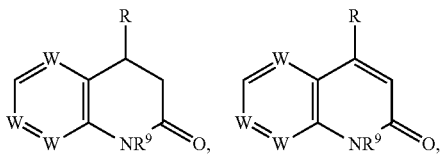

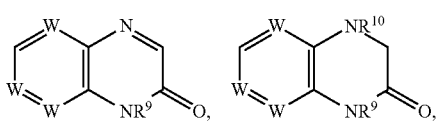

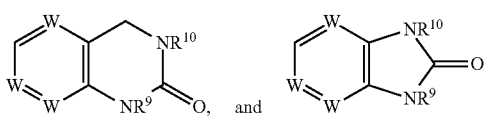

In certain embodiments, Z comes together with

to form a heterocyclic ring selected from

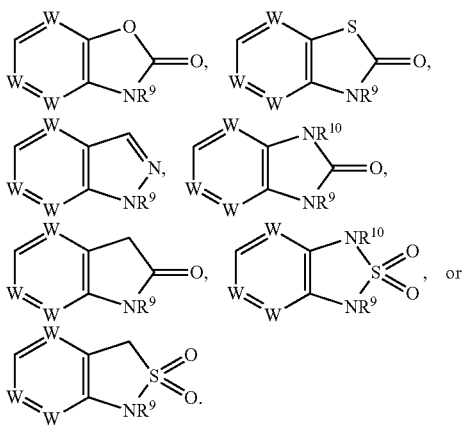

In one embodiment, Z comes together with

to form

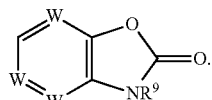

In one embodiment, Z comes together with

to form a heterocyclic ring selected from

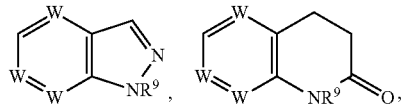

In one embodiment, $R^9$ and $R^{10}$ are each H.

In another embodiment, Z and

are taken together and selected from the group consisting of:

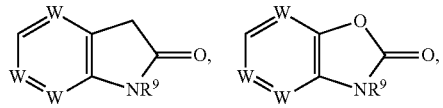

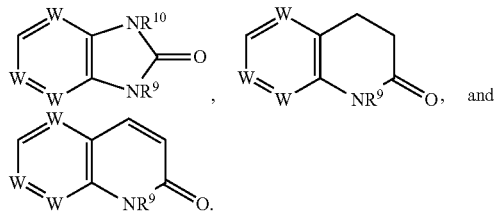

In one embodiment,

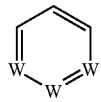

of Formula I-h is substituted with small groups or less bulky groups, for example chloro, fluoro, methyl, or trifluoromethyl.

In certain embodiments, the structure:

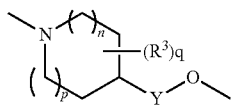

is selected from the group consisting of:

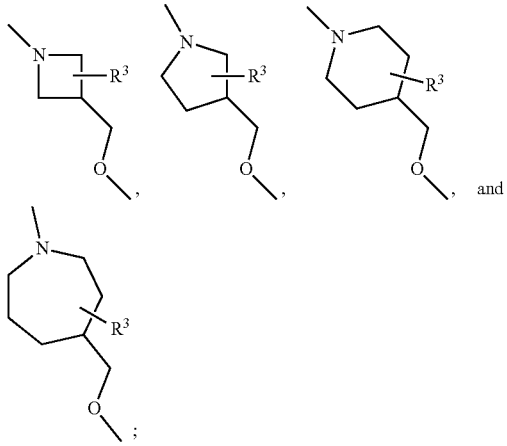

wherein $R^3$ is H, $C_1$-$C_6$ alkyl, or fluoro.

In further embodiments, the compounds are of Formula I-i:

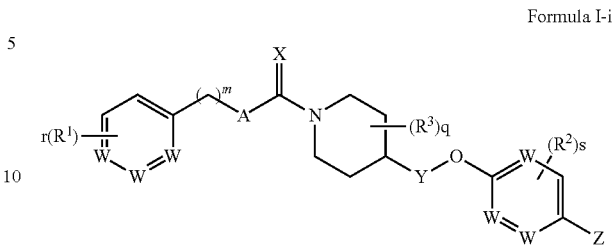

Formula I-i

Wherein each of $R^1$, $R^2$, $R^3$, m, q, r, s, A, X, Y and Z are as defined herein and wherein each W is independently CH, CR or N.

In further embodiments, the compounds are of Formula I-j:

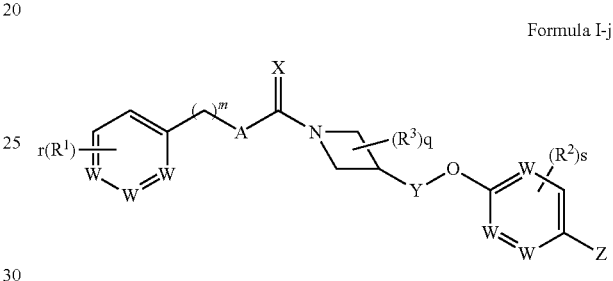

Formula I-j

Wherein each of $R^1$, $R^2$, $R^3$, m, q, r, s, A, X, Y and Z are as defined herein and wherein each W is independently CH, CR or N.

In particular embodiments all W groups in any formula provided herein are selected from the group consisting CH, $CH_2$, N, NH, NR, CR and $CR_2$. In certain embodiments, in at least one ring of any of Formulas I-c, I-d, I-e, I-f, I-g, I-h, I-i, and I-j, at least one W is N. In certain embodiments of any of Formulas I-c, I-d, I-e, I-f, I-g, I-h, I-i, and I-j, at least one W in each ring is N. In particular embodiments, the compound is selected from Table A.

TABLE A

| Compound | Name |
|---|---|
|  | (E)-6-((1-(3-(3,4-dichlorophenyl)acryloyl)piperidin-4-yl)methoxy)-3,4-dihydroquinolin-2(1H)-one |
|  | 4-chlorobenzyl 4-(((2-oxo-1,2,3,4-tetrahydroquinolin-6-yl)oxy)methyl)piperidine-1-carboxylate |

TABLE A-continued

| Compound | Name |
| --- | --- |
| | N-(4-chlorophenyl)-4-(((2-oxo-1,2,3,4-tetrahydroquinolin-6-yl)oxy)methyl)piperidine-1-carboxamide |
| | 6-((1-(2-(4-chlorophenyl)acetyl)piperidin-4-yl)methoxy)-3,4-dihydroquinolin-2(1H)-one |
| | 4-(((2-oxo-1,2,3,4-tetrahydroquinolin-6-yl)oxy)methyl)-N-(4-(trifluoromethyl)phenyl)piperidine-1-carboxamide |
| | N-(4-chlorophenyl)-3-(((2-oxo-1,2,3,4-tetrahydroquinolin-6-yl)oxy)methyl)azetidine-1-carboxamide |
| | N-(3,4-dichlorophenyl)-3-(((2-oxo-1,2,3,4-tetrahydroquinolin-6-yl)oxy)methyl)azetidine-1-carboxamide |
| | 3-(((2-oxo-1,2,3,4-tetrahydroquinolin-6-yl)oxy)methyl)-N-(4-(trifluoromethyl)phenyl)azetidine-1-carboxamide |

TABLE A-continued

| Compound | Name |
|---|---|
| | 6-((1-(1H-imidazole-1-carbonyl)azetidin-3-yl)methoxy)-3,4-dihydroquinolin-2(1H)-one |
| | N-(4-chlorobenzyl)-3-(((2-oxo-1,2,3,4-tetrahydroquinolin-6-yl)oxy)methyl)azetidine-1-carboxamide |
| | (E)-6-((1-(3-(3,4-dichlorophenyl)acryloyl)azetidin-3-yl)methoxy)-3,4-dihydroquinolin-2(1H)-one |
| | 4-chlorobenzyl 3-(((2-oxo-1,2,3,4-tetrahydroquinolin-6-yl)oxy)methyl)azetidine-1-carboxylate |
| | 6-((1-(2-(4-chlorophenyl)acetyl)azetidin-3-yl)methoxy)-3,4-dihydroquinolin-2(1H)-one |
| | 3,4-dichlorobenzyl 3-(((2-oxo-1,2,3,4-tetrahydroquinolin-6-yl)oxy)methyl)azetidine-1-carboxylate |

TABLE A-continued

| Compound | Name |
|---|---|
| | 3,4-dichlorobenzyl 4-(((2-oxo-1,2,3,4-tetrahydroquinolin-6-yl)oxy)methyl)piperidine-1-carboxylate |
| | N-(4-cyclopropylphenyl)-4-(((2-oxo-1,2,3,4-tetrahydroquinolin-6-yl)oxy)methyl)piperidine-1-carboxamide |
| | 6-((1-(2-(4-chloro-3-methylphenyl)acetyl)piperidin-4-yl)methoxy)-3,4-dihydroquinolin-2(1H)-one |
| | N-(3-methyl-4-(trifluoromethyl)phenyl)-4-(((2-oxo-1,2,3,4-tetrahydroquinolin-6-yl)oxy)methyl)piperidine-1-carboxamide |
| | N-(4-chloro-3-methylphenyl)-3-(((2-oxo-1,2,3,4-tetrahydroquinolin-6-yl)oxy)methyl)azetidine-1-carboxamide |
| | N-(3-chlorophenyl)-3-(((2-oxo-1,2,3,4-tetrahydroquinolin-6-yl)oxy)methyl)azetidine-1-carboxamide |

TABLE A-continued

| Compound | Name |
| --- | --- |
| | N-(4-cyclopropylphenyl)-3-(((2-oxo-1,2,3,4-tetrahydroquinolin-6-yl)oxy)methyl)azetidine-1-carboxamide |
| | 6-((1-(1H-pyrrole-1-carbonyl)azetidin-3-yl)methoxy)-3,4-dihydroquinolin-2(1H)-one |
| | N-(4-chloro-3-methylbenzyl)-3-(((2-oxo-1,2,3,4-tetrahydroquinolin-6-yl)oxy)methyl)azetidine-1-carboxamide |
| | 4-chloro-3-methylbenzyl 3-(((2-oxo-1,2,3,4-tetrahydroquinolin-6-yl)oxy)methyl)azetidine-1-carboxylate |
| | 6-((1-(2-(4-chloro-3-fluorophenyl)acetyl)azetidin-3-yl)methoxy)-3,4-dihydroquinolin-2(1H)-one |
| | 4-chloro-3-methylbenzyl 3-(((2-oxo-1,2,3,4-tetrahydroquinolin-6-yl)oxy)methyl)azetidine-1-carboxylate |

TABLE A-continued

| Compound | Name |
|---|---|
| | 4-chlorobenzyl 4-((4-hydroxyphenoxy)methyl)piperidine-1-carboxylate |
| | N-(4-chlorophenyl)-4-((4-hydroxyphenoxy)methyl)piperidine-1-carboxamide |
| | 2-(4-chlorophenyl)-1-(4-((4-hydroxyphenoxy)methyl)piperidin-1-yl)ethanone |
| | 4-((4-hydroxyphenoxy)methyl)-N-(4-(trifluoromethyl)phenyl)piperidine-1-carboxamide |
| | N-(4-chlorophenyl)-3-((4-hydroxyphenoxy)methyl)azetidine-1-carboxamide |
| | N-(3,4-dichlorophenyl)-3-((4-hydroxyphenoxy)methyl)azetidine-1-carboxamide |

TABLE A-continued

| Compound | Name |
|---|---|
| | 3-((4-hydroxyphenoxy)methyl)-N-(4-(trifluoromethyl)phenyl)azetidine-1-carboxamide |
| | (3-((4-hydroxyphenoxy)methyl)azetidin-1-yl)(1H-imidazol-1-yl)methanone |
| | N-(4-chlorobenzyl)-3-((4-hydroxyphenoxy)methyl)azetidine-1-carboxamide |
| | (E)-3-(3,4-dichlorophenyl)-1-(4-((4-hydroxyphenoxy)methyl)piperidin-1-yl)prop-2-en-1-one |
| | (E)-3-(3,4-dichlorophenyl)-1-(3-((4-hydroxyphenoxy)methyl)azetidin-1-yl)prop-2-en-1-one |
| | 4-chlorobenzyl 3-((4-hydroxyphenoxy)methyl)azetidine-1-carboxylate |
| | 2-(4-chlorophenyl)-1-(3-((4-hydroxyphenoxy)methyl)azetidin-1-yl)ethanone |

TABLE A-continued

| Compound | Name |
|---|---|
| | 3,4-dichlorobenzyl 3-((4-hydroxyphenoxy)methyl)azetidine-1-carboxylate |
| | 3,4-dichlorobenzyl 4-((4-hydroxyphenoxy)methyl)piperidine-1-carboxylate |
| | N-(4-chloropropylphenyl)-4-((4-hydroxyphenoxy)methyl)piperidine-1-carboxamide |
| | 2-(4-chloro-3-methylphenyl)-1-(4-((4-hydroxyphenoxy)methyl)piperidin-1-yl)ethanone |
| | 4-((4-hydroxyphenoxy)methyl)-N-(3-methyl-4-(trifluoromethyl)phenyl)piperidine-1-carboxamide |
| | N-(4-chloro-3-methylphenyl)-3-((4-hydroxyphenoxy)methyl)azetidine-1-carboxamide |

TABLE A-continued

| Compound | Name |
|---|---|
| | N-(3-chlorophenyl)-3-((4-hydroxyphenoxy)methyl)azetidine-1-carboxamide |
| | N-(4-cyclopropylphenyl)-3-((4-hydroxyphenoxy)methyl)azetidine-1-carboxamide |
| | (3-((4-hydroxyphenoxy)methyl)azetidin-1-yl)(1H-pyrrol-1-yl)methanone |
| | N-(4-chloro-3-methylbenzyl)-3-((4-hydroxyphenoxy)methyl)azetidine-1-carboxamide |
| | 4-chloro-3-methylbenzyl 3-((4-hydroxyphenoxy)methyl)azetidine-1-carboxylate |
| | 2-(4-chloro-3-fluorophenyl)-1-(3-((4-hydroxyphenoxy)methyl)azetidin-1-yl)ethanone |
| | 4-chloro-3-methylbenzyl 3-((4-hydroxyphenoxy)methyl)azetidine-1-carboxylate |

TABLE A-continued

| Compound | Name |
|---|---|
| | 4-chlorobenzyl 4-((4-(3-methylureido)phenoxy)methyl)piperidine-1-carboxylate |
| | 1-(4-((1-(2-(4-chlorophenyl)acetyl)piperidin-4-yl)methoxy)phenyl)-3-methylurea |
| | N-(4-chlorophenyl)-3-((4-(3-methylureido)phenoxy)methyl)azetidine-1-carboxamide |
| | (E)-1-(4-((1-(3-(3,4-dichlorophenyl)acryloyl)azetidin-3-yl)methoxy)phenyl)-3-methylurea |
| | 4-chlorobenzyl 3-((4-(3-methylureido)phenoxy)methyl)azetidine-1-carboxylate |
| | 1-(4-((1-(2-(4-chlorophenyl)acetyl)azetidin-3-yl)methoxy)phenyl)-3-methylurea |

TABLE A-continued

| Compound | Name |
|---|---|
| | 3,4-dichlorobenzyl 3-((4-(3-methylureido)phenoxy)methyl)azetidine-1-carboxylate |
| | 3,4-dichlorobenzyl 4-((4-(3-methylureido)phenoxy)methyl)piperidine-1-carboxylate |
| | N-(4-cyclopropylphenyl)-4-((4-(3-methylureido)phenoxy)methyl)piperidine-1-carboxamide |
| | 1-(4-((1-(2-(4-chloro-3-methylphenyl)acetyl)piperidin-4-yl)methoxy)phenyl)-3-methylurea |
| | N-(4-cyclopropylphenyl)-3-((4-(3-methylureido)phenoxy)methyl)azetidine-1-carboxamide |
| | 1-(4-((1-(1H-pyrrole-1-carbonyl)azetidin-3-yl)methoxy)phenyl)-3-methylurea |

TABLE A-continued
| Compound | Name |
|---|---|
| | 4-chloro-3-methylbenzyl 3-((4-(3-methylureido)phenoxy)methyl)azetidine-1-carboxylate |
| | 1-(4-((1-(2-(4-chloro-3-fluorophenyl)acetyl)azetidin-3-yl)methoxy)phenyl)-3-methylurea |
| | 4-chloro-3-methylbenzyl 3-((4-(3-methylureido)phenoxy)methyl)azetidine-1-carboxylate |
In one embodiment, the compound is selected from the group consisting of:
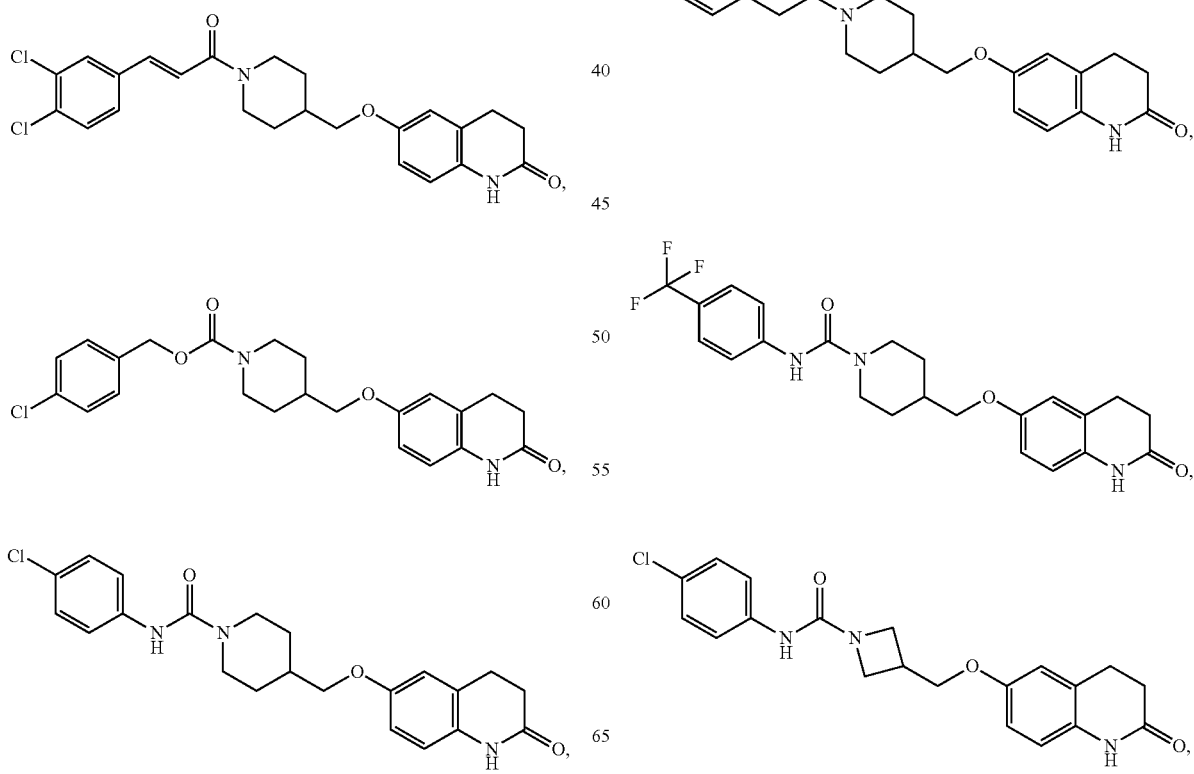

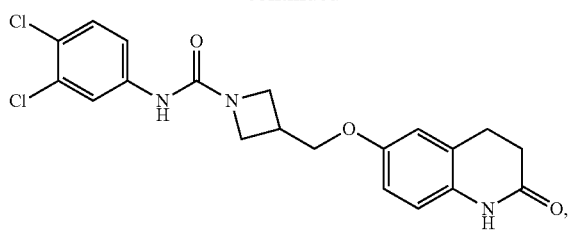

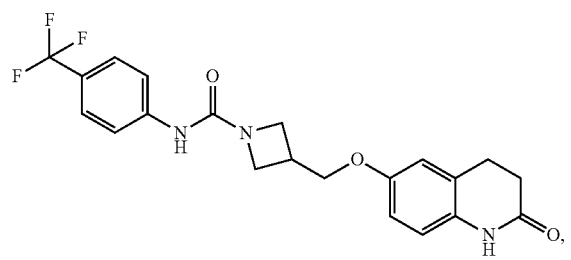

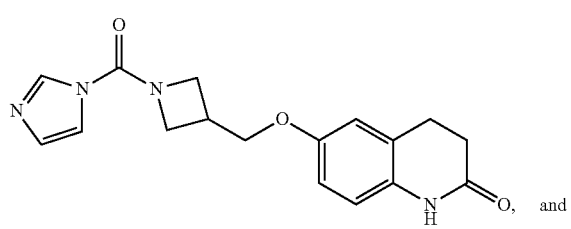

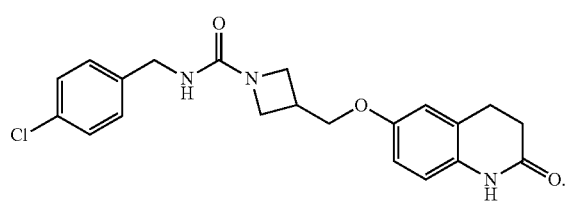, and

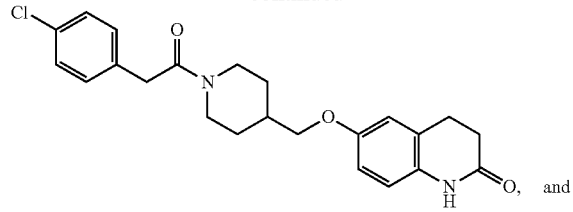

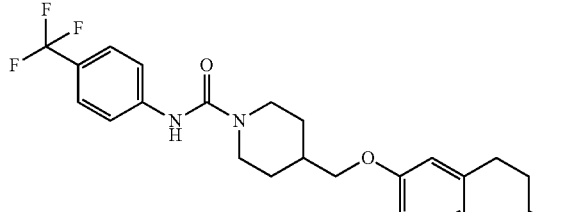

In other embodiments, the compound is selected from the group consisting of:

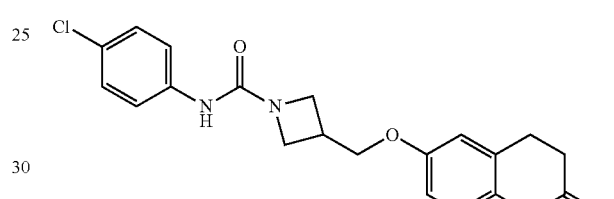

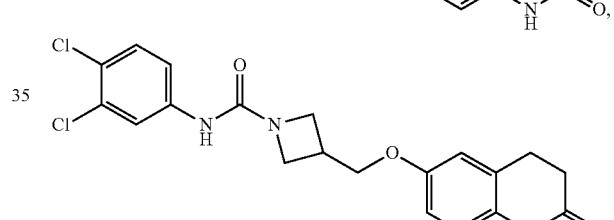

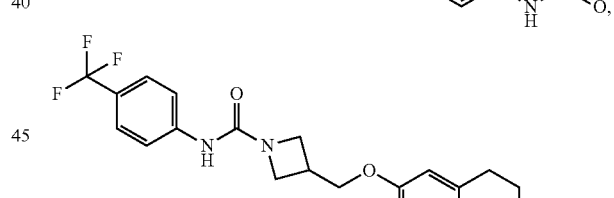, and

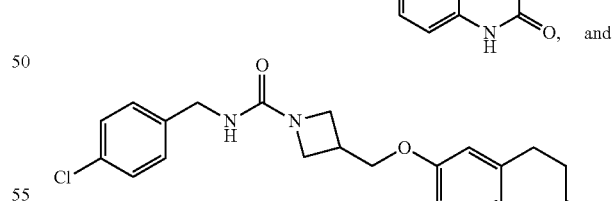

In certain embodiments, the compound is selected from the group consisting of:

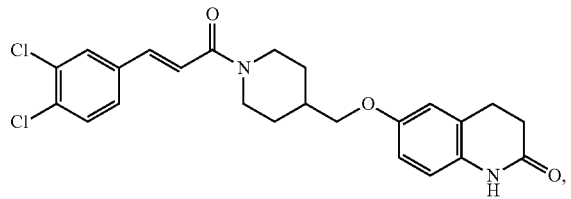

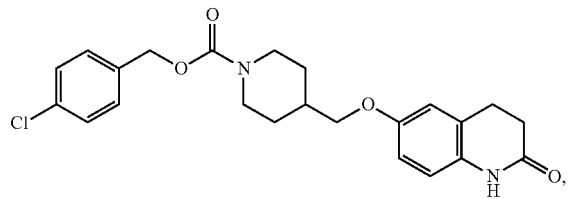

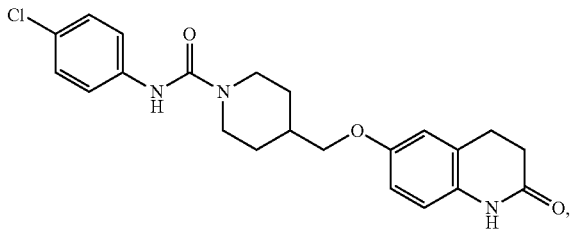

Enantiomers

In certain embodiments, the compounds are provided as enantiomers. In one embodiment, the compound is provided as an enantiomer or mixture of enantiomers. In a particular embodiment, the compound is present as a racemic mixture. The enantiomer can be named by the configuration at the chiral center, such as R or S. In certain embodiments, the compound is present as a racemic mixture of R- and S-enantiomers. In certain embodiments, the compound is present as a mixture of two enantiomers. In one embodiment, the mixture has an enantiomeric excess in R. In one embodiment, the mixture has an enantiomeric excess in S. In certain other embodiments, the compound is in an enantiomeric excess of the R- or S-enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the single enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the R enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the S enantiomer.

In other embodiments, the compound is substantially in the form of a single enantiomer. In some embodiments, the compound is present substantially in the form of the R enantiomer. In some embodiments, the compound is present substantially in the form of the S enantiomer. The phrase "substantially in the form of a single enantiomer" is intended to mean at least 70% or more in the form of a single enantiomer, for example 70% or more, 75% or more, 80% or more, 85% or more, 90% or more, 95% or more, 98% or more, or 99% or more in either the R or S enantiomer.

The enantiomer can be named by the direction in which it rotates the plane of polarized light. If it rotates the light clockwise as seen by the viewer towards whom the light is traveling, the isomer can be labeled (+), or referred to as dextrorotary; and if it rotates the light counterclockwise, the isomer can be labeled (−) or referred to as levorotary. In certain embodiments, the compound is present as a racemic mixture of (+) and (−) isomers. In certain embodiments, the compound is present as a mixture of two isomers. In one embodiment, the mixture has an excess in (+). In one embodiment, the mixture has an excess in (−). In certain other embodiments, the compound is in an excess of the (+) or (−) isomer. The isomeric excess can be 51% or more, such as 51% or more, 55% or more, 60% or more, 65% or more, 70% or more, 75% or more, 80% or more, 85% or more, 90% or more, 95% or more, 98% or more, or 99% or more in the (+) isomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the (−) isomer.

In other embodiments, the compound is substantially in the form of a single optical isomer. In some embodiments, the compound is present substantially in the form of the (+) isomer. In other embodiments, the compound is present substantially in the form of the (−) isomer. The phrase "substantially in the form of a single optical isomer" is intended to mean at least 70% or more in the form of a single isomer, for example 70% or more, 75% or more, 80% or more, 85% or more, 90% or more, 95% or more, 98% or more, or 99% or more of either the (+) or (−) isomer.

Methods of Use

The compounds described herein can generally be used to treat, prevent or produce a reduction in symptoms of neurologic disorders, which includes abnormalities of the nervous system. These disorders can be characterized by primary location, dysfunction/abnormality or cause. Central nervous system disorders impact the brain or spinal cord, while peripheral nervous system disorders affect the nerves. Causes include, for example, genetic abnormalities, developmental abnormalities, injury, ischemia, or trauma, infection, cancer or diseases and disorders of the vasculature that supplies the nervous system, for example stroke. In certain instances, the neurologic disorder may be associated with NMDA receptor activation, and in particular with activation of NMDA receptors including a GluN2B subunit.

Disorders that can be treated, prevented or for which symptoms can be reduced include neuropsychiatric disorders, neurodegenerative disorders, as well as neurologic disorders including neuropathic pain, inflammatory pain, stroke, traumatic brain injury, epilepsy, transient ischemica, global ischemia, hypoxia, spinal cord trauma and other neurologic events.

In certain embodiments, the compounds are used for the treatment or prevention of neuropsychiatric disorders. These disorders include, without limitation, depression, anxiety, bipolar disorder, obsessive-compulsive disorder, alcohol and substance abuse, and attention-deficit hyperactivity disorder.

In certain other embodiments, the compounds are used for the treatment or prevention of neurodegenerative disorders. These disorders are typically characterized by gradual and progressive nervous system dysfunction due to loss of neuronal cells and neuronal tissue and include, without limitation, Alzheimer's disease, Parkinson's disease, Huntington's disease, Amyotrophic lateral sclerosis (ALS/Lou Gehrig's disease), Multiple Sclerosis, spinal muscular atrophy, spinal & bulbar muscular atrophy, familial spastic paraparesis, Machado Joseph disease Friedreich's ataxia and Lewy body disease.

In certain embodiments, a method of treatment a neurologic disorder are provided including administering a compound of Formula I, or a pharmaceutically acceptable salt, ester or prodrug thereof, to a host in need thereof. In certain embodiments, the disorder is associated with NMDA receptor activation. In one embodiment, the disorder is a neuropsychiatric disorder. In another embodiment, the disorder is a neurodegenerative disorder. In certain other embodiments, the disorder is neuropathic pain. In yet further embodiments, the disorder is an injury resulting from an ischemic event or neuropathic injury or infection.

In certain embodiments, methods are provided to prevent neurodegeneration in patients with Parkinson's, Alzheimer's, Huntington's chorea, ALS, and other neurodegenerative conditions.

Uses of the compounds in the treatment or manufacture of a medicament for such disorders are also provided.

In certain embodiments, a method of treatment or prevention of neurologic disorder, such as a neuropsychiatric or neurodegenerative disease or disorder or a disorder resulting from injury, trauma, infection or ischemia, in a host is provided including administering a compound of Formula I or a pharmaceutically acceptable salt, ester or prodrug thereof to the host, either alone or in combination, in which the host is suffering from a reduced pH in a region of the brain. In certain embodiments, a disorder has caused a region with a pH below pH 7.6, or below 7.5, or below 7.4, or below 7.3, or below 7.2, or below 7.1, or below 7, or below 6.9, or below 6.8, or below 6.7, or below 6.6 or below 6.5 or below 6.4. In certain embodiments, the reduced pH is due to pathological conditions such as hypoxia resulting from stroke, traumatic brain injury, global ischemia, such as global ischemia that may occur during cardiac surgery, hypoxia, including hypoxia that may occur following cessation of breathing, pre-eclampsia, spinal cord trauma, epilepsy, status epilepticus, neuropathic pain, inflammatory pain, chronic pain, vascular dementia and glioma tumors.

In one embodiment, methods are provided to attenuate the progression of an ischemic or excitotoxic cascade by administering a compound of Formula I. In addition, methods are provided to decrease infarct volume by administering a compound of Formula I. Still further, methods are provided to decrease behavioral deficits associated with an ischemic event by administering a compound of Formula I. In one embodiment, methods are provided to treat patients with ischemic injury or hypoxia, or prevent or treat the neuronal toxicity associated with ischemic injury or hypoxia, by administering a compound or composition described herein. In one particular embodiment, the ischemic injury is stroke. In another particular embodiment, the ischemic injury is vasospasm after subarachnoid hemorrhage. In other embodiments, the ischemic injury is selected from, but not limited to, one of the following: traumatic brain injury, cognitive deficit after bypass surgery, cognitive deficit after carotid angioplasty; and/or neonatal ischemia following hypothermic circulatory arrest.

Further, compounds selected according to the methods or processes described herein can be used prophylactically to prevent or protect against such neurologic or neuropathologic diseases, disorders or conditions, such as those described herein. In one embodiment, patients with a predisposition for an ischemic event, such as a genetic predisposition, can be treated prophylactically with the methods and compounds described herein. In another embodiment, patients at risk for or exhibiting vasospasms can be treated prophylactically with the methods and compounds described herein. In a further embodiment, patients undergoing cardiac bypass surgery can be treated prophylactically with the methods and compounds described herein. In one embodiment, the compounds of the present invention can be used as neuroprotectants.

In another embodiment, methods are provided to treat patients with neuropathic pain or related disorders by administering a compound or composition described herein. In certain embodiments, the neuropathic pain or related disorder can be selected from the group including, but not limited to: peripheral diabetic neuropathy, postherpetic neuralgia, complex regional pain syndromes, peripheral neuropathies, chemotherapy-induced neuropathic pain, cancer neuropathic pain, neuropathic low back pain, HIV neuropathic pain, trigeminal neuralgia, and/or central post-stroke pain. This dysfunction can be associated with common symptoms such as allodynia, hyperalgesia, intermittent abnormal sensations, and spontaneous, burning, shooting, stabbing, paroxysmal or electrical-sensations, paresthesias, hyperpathia and/or dysesthesias, which can also be treated by the compounds and methods described herein.

Further, the compounds and methods described herein can be used to treat neuropathic pain resulting from peripheral or central nervous system pathologic events, including, but not limited to trauma; ischemia; infections or endocrinologic disorders, including, but not limited to, diabetes mellitus, diabetic neuropathy, amyloidosis, amyloid polyneuropathy (primary and familial), neuropathies with monoclonal proteins, vasculitic neuropathy, HIV infection, herpes zoster—shingles and/or postherpetic neuralgia; neuropathy associated with Guillain-Barre syndrome; neuropathy associated with Fabry's disease; entrapment due to anatomic abnormalities; trigeminal and other CNS neuralgias; malignancies; inflammatory conditions or autoimmune disorders, including, but not limited to, demyelinating inflammatory disorders, rheumatoid arthritis, systemic lupus erythematosus, Sjogren's syndrome; and cryptogenic causes, including, but not limited to idiopathic distal small-fiber neuropathy. Other causes of neuropathic pain that can be treated according to the methods and compositions described herein include, but are not limited to, exposure to toxins or drugs (such as arsenic, thallium, alcohol, vincristine, cisplatinum and dideoxynucleosides), dietary or absorption abnormalities, immunoglobulinemias, hereditary abnormalities and amputations (including mastectomy). Neuropathic pain can also result from compression of nerve fibers, such as radiculopathies and carpal tunnel syndrome.

In a further embodiment, methods are provided to treat patients with neurodegenerative diseases by administering a compound selected according to the methods or processes described herein. These neurodegenerative disorders include, without limitation, Alzheimer's disease, Parkinson's disease, Huntington's disease, Amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia and Lewy body disease. In one embodiment, the neurodegenerative disease can be Parkinson's disease. In another embodiment, the neurodegenerative disease can be Alzheimer's disease. In another embodiment, the neurodegenerative disease can be Huntington's disease and/or ALS.

In another embodiment, methods are provided to treat patients with brain tumors by administering a compound selected according to the methods or processes described herein. In some embodiments, the compounds are useful in the treatment of tumor growth. In certain embodiments, the compounds reduce tumor mass. In one embodiment, the compounds are useful in the treatment or prophylaxis of a neurologic event involving acidification of brain or spinal cord tissue. In another embodiment, the NMDA receptor antagonists of this invention are useful both in the treatment of stroke and head trauma, and for use as prophylactic agents for at risk patients. The acid generated by ischemic tissue during stroke is harnessed since the neuroprotective agents described herein are more potent at acidic pH. In this way side effects are minimized in unaffected tissue since drug at these sites are less potent. These compounds may be used to reduce the amount of neuronal death associated with stroke and head trauma. They may be given chronically to individuals with epilepsy or who are at risk for stroke or head trauma, preoperatively in high risk heart/brain surgery, etc., in order to lengthen the window of opportunity for subsequent therapy.

In addition, methods are provided to treat the following diseases or neurological conditions, including, but not limited to: chronic nerve injury, chronic pain syndromes, such as, but not limited to diabetic neuropathy, ischemia, ischemia following transient or permanent vessel occlusion, seizures, spreading depression, restless leg syndrome, hypocapnia, hypercapnia, diabetic ketoacidosis, fetal asphyxia, spinal cord injury, traumatic brain injury, status epilepticus, epilepsy, hypoxia, perinatal hypoxia, concussion, migraine, hypocapnia, hyperventilation, lactic acidosis, fetal asphyxia during parturition, brain gliomas, and/or retinopathies by administering a compound selected according to the methods or processes described herein.

In certain embodiments, the compounds are used for the treatment or prevention of neuropsychiatric disorders. Generally, these disorders are mental disturbances attributable to diseases of the nervous system. These disorders include depression, anxiety, bipolar disorder, obsessive-compulsive disorder, alcohol and substance abuse, and attention-deficit hyperactivity disorder. In particular embodiments, the disorders are neuropsychiatric mood disorders, non-limiting examples of which include depression, including major depression, treatment-resistant depression and treatment-resistant bipolar depression, bipolar disorders including cyclothymia (a mild form of bipolar disorder), affective disorders such as SAD (seasonal affective disorder) and mania (euphoric, hyperactive, over inflated ego, unrealistic optimism). In certain embodiments, the disorder is treatment-resistant depression or treatment-resistant bipolar depression. Neuropsychiatric disorders also include attention deficit disorders such as ADD or ADHD. In certain embodiments, a method of treatment a neuropsychiatric disorder is provided including administering a compound of the invention, alone or in combination to a host diagnosed with the disorder. Uses of the compounds in the treatment or manufacture of a medicament for such disorders are also provided.

In certain embodiments, the compounds are used for the treatment of depression in a host diagnosed with the disorder. In certain other embodiments, the compounds are used for treatment of a bipolar disorder in a host diagnosed with the disorder. The compounds can also be used to diminish the severity of depressive or manic episodes or prevent future episodes. In certain embodiments, methods of treating seasonal disorders is provided including administering the compound to a host at risk of suffering from a SAD. In particular, the compounds can be provided on a seasonal basis. In some embodiments, the host has been diagnosed as suffering from or is at risk for SAD or depression. In certain embodiments, the host is at risk of suffering from a mania. The mania can be characterized by euphoria, hyperactivity, over-inflated ego, or unrealistic optimism. In certain embodiments, the host is suffering from an attention deficit disorders, for example ADD or ADHD.

Depression, formally called major depression, major depressive disorder or clinical depression, is a medical illness that involves the mind and body. Most health professionals today consider depression a chronic illness that requires long-term treatment, much like diabetes or high blood pressure. Although some people experience only one episode of depression, most have repeated episodes of depression symptoms throughout their life. Depression is also a common feature of mental illness, whatever its nature and origin. In other instances, the host does not have a history of a major psychiatric disorder but has been diagnosed with suffering from at least one depressive episode. In other instances, the host has been diagnosed with bipolar disorder. The host may also have been diagnosed as suffering from panic attacks or anxiety.

In some instances, the host is not suffering from a chronic disorder but is at risk of a depressive episode, anxiety or a panic attack due to environmental circumstances. The compounds may be given prophylactically to prevent onset of such an episode. For instance, in certain instances the compounds can be provided to a host before a plane trip, a public speech, or other potential stressful even that could lead to an episode. In some embodiments, therefore, a method of prevention of a neuropsychiatric episode is provided, including administering a compound of the invention to a host at risk of suffering from such an episode. In some instances, the compounds are useful for treatment or prophylaxis of disorders such as depression or bipolar disorder associated with an injury or with aging.

In one embodiment, the compounds provided herein block the GluN2B-containing NMDA receptors, have varying activity against receptors containing GluN2A or GluN2D, and may be selective for other members of the NMDA receptor family (GluN2C, GluN3A and GluN3B). In one embodiment, the compounds are selective NMDA receptor blockers. In one embodiment, the compounds are NMDA receptor antagonists selective for GluN2B, GluN2A, GluN2C, GluN2D, GluN3A, and/or GluN3B that do not interact with other receptors or ion channels at therapeutic concentrations.

In one embodiment, the compound is a selective GluN1/GluN2A NMDA receptor. In one embodiment, the compound is a selective GluN1/GluN2B NMDA receptor antagonist. In one particular embodiment, the compounds can bind to the GluN2B subunit of the NMDA receptor. In another particular embodiment, the compounds are selective for the GluN2B subunit of the NMDA receptor. In one embodiment, the compound is not an NMDA receptor glutamate site antagonist. In another embodiment, the compound is not an NMDA receptor glycine site antagonist.

GluN2B-containing NMDA receptors may also be referred to as NR2B-containing NMDA receptors. Similarly, GluN2A is used interchangeably with NR2A, GluN2D with NR2D, GluN2C with NR2c, GluN3A with NR3A, and GluN3B with NR3B.

In certain embodiments, the compounds are administered to a host suffering from or at risk of suffering from age-related depression. The compounds can be administered prophylactically to a host over the age of 60, or over the age of 70, or over the age of 80 to prevent or reduce the severity of depressive episodes.

In certain embodiments, compounds of the present invention can be used to activate or stimulate the mTOR signaling pathway. In one embodiment, the compounds can be used to modulate mTOR activity in the brain, for example in the prefrontal cortex. Compounds which modulate or stimulate mTOR signaling may be useful in the treatment or prophylaxis of depression and other neuropsychiatric disorders.

In a particular embodiment, compounds of the present invention may be used to treat traumatic brain injury caused by a blast or a blast injury.

In one embodiment, the compounds may be used to in the treatment of schizophrenia. In another embodiment, the compounds may not be used to treat schizophrenia.

Side Effects

In an additional aspect of the methods and processes described herein, the compound does not exhibit substantial toxic and/or psychotomimetic side effects. Side effects associated with prior NMDAR blockers include, but are not limited to, agitation, hallucination, confusion, stupor, paranoia, delirium, psychotomimetic-like symptoms, rotarod impairment, amphetamine-like stereotyped behaviors, stereotypy, psychosis memory impairment, motor impairment, anxiolytic-like effects, increased blood pressure, decreased blood pressure, increased pulse, decreased pulse, hematological abnormalities, electrocardiogram (ECG) abnormalities, cardiac toxicity, heart palpitations, motor stimulation, psychomotor performance, mood changes, short-term memory deficits, long-term memory deficits, arousal, sedation, extrapyramidal side-effects, ventricular tachycardia. Lengthening of cardiac repolarisation, agitation, ataxia, cognitive deficits and/or schizophrenia-like symptoms.

The compounds selected or identified according to the processes and methods described herein generally avoid substantial side effects associated with other classes of NMDA receptor antagonists. In a particular embodiment, the compound has a therapeutic index equal to or greater than at least 2. In another embodiment, the compound is at least 10 times more selective for binding to an NMDA receptor than any other glutamate receptor. In a further additional or alternative embodiment, the compound has a therapeutic index equal to or greater than at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 40:1, at least 50:1, at least 75:1, at least 100:1 or at least 1000:1. The therapeutic index can be defined as the ratio of the dose required to produce toxic or lethal effects to dose required to produce therapeutic responses. It can be the ratio between the median toxic dose (the dosage at which 50% of the group exhibits the adverse effect of the drug) and the median effective dose (the dosage at which 50% of the population respond to the drug in a specific manner). The higher the therapeutic index, the more safe the drug is considered to be. It simply indicates that it would take a higher dose to invoke a toxic response that it does to cause a beneficial effect.

In one embodiment, such compounds do not substantially exhibit the side effects associated with NMDA receptor antagonists of the glutamate site, such as selfotel, D-CPPene (SDZ EAA 494) and AR-R15896AR (ARL 15896AR), including, agitation, hallucination, confusion and stupor (Davis et al. (2000) *Stroke* 31(2):347-354; Diener et al. (2002), *J Neurol* 249(5):561-568); paranoia and delirium (Grotta et al. (1995), *J Intern Med* 237:89-94); psychotomimetic-like symptoms (Loscher et al. (1998), *Neurosci Lett* 240(1):33-36); poor therapeutic ratio (Dawson et al. (2001), *Brain Res* 892(2):344-350); amphetamine-like stereotyped behaviors (Potschka et al. (1999), *Eur J Pharmacol* 374(2): 175-187). In another embodiment, such compounds do not exhibit the side effects associated with NMDA antagonists of the glycine site, such as HA-966, L-701,324, d-cycloserine, CGP-40116, and ACEA 1021, including significant memory impairment and motor impairment (Wlaz, P (1998), *Brain Res Bull* 46(6):535-540). In a still further embodiment, such compounds do not exhibit the side effects of NMDA high affinity receptor channel blockers, such as MK-801 and ketamine, including, psychosis-like effects (Hoffman, D C (1992), *J Neural Transm Gen Sect* 89:1-10); cognitive deficits (decrements in free recall, recognition memory, and attention; Malhotra et al (1996), *Neuropsychopharmacology* 14:301-307); schizophrenia-like symptoms (Krystal et al (1994), *Arch Gen Psychiatry* 51:199-214; Lahti et al. (2001), *Neuropsychopharmacology* 25:455-467), and hyperactivity and increased stereotypy (Ford et al (1989) *Physiology and behavior* 46: 755-758.

The side effect profile of compounds can be determined by any method known to those skilled in the art. In one embodiment, motor impairment can be measured by, for example, measuring locomotor activity and/or rotorod performance. Rotorod experiments involve measuring the duration that an animal can remain on an accelerating rod. In another embodiment, memory impairment can be assessed, for example, by using a passive avoidance paradigm; Sternberg memory scanning and paired words for short-term memory, or delayed free recall of pictures for long-term memory. In a further embodiment, anxiolytic-like effects can be measured, for example, in the elevated plus maze task. In other embodiments, cardiac function can be monitored, blood pressure and/or body temperature measured and/or electrocardiograms conducted to test for side effects. In other embodiments, psychomotor functions and arousal can be measured, for example by analyzing critical flicker fusion threshold, choice reaction time, and/or body sway. In other embodiments, mood can be assessed using, for example, self-ratings. In further embodiments, schizophrenic symptoms can be evaluated, for example, using the PANSS, BPRS, and CGI, side-effects were assessed by the HAS and the S/A scale.

In one embodiment, the compound does not exhibit substantial toxic side effects, such as, for example, motor impairment or cognitive impairment. In a particular embodiment, the compound has a therapeutic index equal to or greater than at least 2. In another embodiment, the compound is at least 10 times more selective for binding to an NMDA receptor than any other glutamate receptor.

In one embodiment, the $IC_{50}$ value of the compound is 0.001 to 10 µM, 0.005 to 10 µM, 0.01 to 10 µM, 0.01 to 9 µM, 0.01 to 8 µM, 0.01 to 7 µM, 0.01 to 6 µM, 0.01 to 5 µM, 0.001 to 5 µM, 0.005 to 5 µM, 0.01 to 4 µM, 0.01 to 3 µM, 0.01 to 2 µM, 0.01 to 1 µM, 0.05 to 7 µM, 0.05 to 6 µM, 0.05 to 5 µM, 0.05 to 4 µM, 0.05 to 3 µM, 0.05 to 2 µM, 0.05 to 1 µM, 0.05 to 0.5 µM, 0.1 to 7 µM, 0.1 to 6 µM, 0.1 to 5 µM, 0.1 to 4 µM, 0.1 to 3 µM, 0.1 to 2 µM, 0.1 to 1 µM, 0.1 to 0.5 µM, 0.1 to 0.4 µM, 0.1 to 0.3 µM, or 0.1 to 0.2 µM.

In certain embodiments, the compound binds to hERG receptors at an $IC_{50}$ at least 10 times the $IC_{50}$ of inhibition of an NMDA receptor at either pH 6.9, pH 7.4, or 7.6. In certain embodiments, the compound binds adrenergic receptors, in particular α1-adrenergic receptors at an $IC_{50}$ at least 10 times the $IC_{50}$ of inhibition of an NMDA receptor at either pH 6.9, pH 7.4 or 7.6. In specific embodiments the ratio of $IC_{50}$'s between either hERG binding or adrenergic receptor binding and NMDA receptor antagonism at pH 6.9 or pH 7.4 is greater than 50, or greater than 100, or greater than 500.

Certain studies have indicated that pH may be altered in brains of individuals suffering from certain neuropsychiatric disorder (see e.g. Karolewicz, et al. (2004) *J. Neurochem* 91:1057-66. Xing, et al. (2002) *Schizophr Res.* 58:21-30.) A reduced brain pH can be harnessed to engage the pH dependent antagonism of the agents described herein. In this way side effects are minimized in unaffected tissue since drug at these sites are less active.

In particular embodiments, the compound is pH sensitive. In specific embodiments, the compound exhibits a potency boost of at least 2, at least 3, at least 4, at least 5, at least 6, at least 7, at least 8, or at least 9 when comparing the $IC_{50}$ at physiological pH versus the $IC_{50}$ diseased pH (i.e., ($IC_{50}$ at phys pH/$IC_{50}$ at diseased pH)).

In one embodiment, the compound has an $IC_{50}$ value of less than 10 µM at a pH of about 6 to about 9. In one embodiment, the compound has an $IC_{50}$ value of less than 10 µM at a pH of about 6.9. In another embodiment, the compound has an $IC_{50}$ value of less than 10 µM at a pH of about 7.4. In another embodiment, the compound has an $IC_{50}$ value of less than 10 µM at a pH of about 7.6. In one embodiment, the compound has an $IC_{50}$ value of less than 10 µM at physiological pH. In one embodiment, the compound has an $IC_{50}$ value of less than 10 µM at ischemic pH.

In another embodiment, the compound has an $IC_{50}$ value of less than 10 µM at a pH of about 7.6. In one embodiment, the compound has an $IC_{50}$ value of less than 10 µM at physiological pH. In one embodiment, the compound has an $IC_{50}$ value of less than 10 µM at ischemic pH.

In one embodiment, the $IC_{50}$ value of the compound is 0.01 to 10 µM, 0.01 to 9 µM, 0.01 to 8 µM, 0.01 to 7 µM, 0.01 to 6 µM, 0.01 to 5 µM, 0.01 to 4 µM, 0.01 to 3 µM, 0.01 to 2 µM, 0.01 to 1 µM, 0.05 to 7 µM, 0.05 to 6 µM, 0.05 to 5 µM, 0.05 to 4 µM, 0.05 to 3 µM, 0.05 to 2 µM, 0.05 to 1 µM, 0.05 to 0.5 µM, 0.1 to 7 µM, 0.1 to 6 µM, 0.1 to 5 µM, 0.1 to 4 µM, 0.1 to 3 µM, 0.1 to 2 µM, 0.1 to 1 µM, 0.1 to 0.5 µM, 0.1 to 0.4 µM, 0.1 to 0.3 µM, or 0.1 to 0.2 µM, and the ratio of the $IC_{50}$ values at pH 7.6 to pH 6.9 for the compound is greater than 1, 2, 3, 4, 5, 6, 7, 8, 9, 10, 15, 20, 25, 30, 40, 50, 60, 70, 80, 90, or 100.

In one embodiment, the $IC_{50}$ value of the compound is 0.01 to 10 µM, 0.01 to 9 µM, 0.01 to 8 µM, 0.01 to 7 µM, 0.01 to 6 µM, 0.01 to 5 µM, 0.01 to 4 µM, 0.01 to 3 µM, 0.01 to 2 µM, 0.01 to 1 µM, 0.05 to 7 µM, 0.05 to 6 µM, 0.05 to 5 µM, 0.05 to 4 µM, 0.05 to 3 µM, 0.05 to 2 µM, 0.05 to 1 µM, 0.05 to 0.5 µM, 0.1 to 7 µM, 0.1 to 6 µM, 0.1 to 5 µM, 0.1 to 4 µM, 0.1 to 3 µM, 0.1 to 2 µM, 0.1 to 1 µM, 0.1 to 0.5 µM, 0.1 to 0.4 µM, 0.1 to 0.3 µM, or 0.1 to 0.2 µM, and the ratio of the $IC_{50}$ values at pH 7.6 to pH 6.9 for the compound is between 1 and 100, 2 and 100, 3 and 100, 4 and 100, 5 and 100, 6 and 100, 7 and 100, 8 and 100, 9 and 100, 10 and 100, 15 and 100, 20 and 100, 25 and 100, 30 and 100, 40 and 100, 50 and 100, 60 and 100, 70 and 100, 80 and 100, or 90 and 100.

Pharmaceutical Compositions

Mammals, and specifically humans, suffering from or at risk of neuropsychiatric disorders can be treated by either targeted or systemic administration, via oral, inhalation, topical, trans- or sub-mucosal, subcutaneous, parenteral, intramuscular, intravenous or transdermal administration of a composition comprising an effective amount of the compounds described herein or a pharmaceutically acceptable salt, ester or prodrug thereof, optionally in a pharmaceutically acceptable carrier.

The compounds or composition is typically administered by oral administration. Alternatively, compounds can be administered BY HAND inhalation. In another embodiment, the compound is administered transdermally (for example via a slow release patch), or topically. In yet another embodiment, the compound is administered subcutaneously, intravenously, intraperitoneally, intramuscularly, parenterally, or submucosally. In any of these embodiments, the compound is administered in an effective dosage range to treat the target condition.

In one embodiment, compounds of the present invention are administered orally. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

When the compound is administered orally in the form of a dosage unit such as a tablets, pills, capsules, troches and the like, these can contain any of the following ingredients, or compounds of a similar nature: a binder (such as microcrystalline cellulose, gum tragacanth or gelatin); an excipient (such as starch or lactose), a disintegrating agent (such as alginic acid, Primogel, or corn starch); a lubricant (such as magnesium stearate or Sterotes); a glidant (such as colloidal silicon dioxide); a sweetening agent (such as sucrose or saccharin); and/or a flavoring agent (such as peppermint, methyl salicylate, or orange flavoring). When the dosage unit form is a capsule, it can contain, in addition to material of the above type, a liquid carrier (such as a fatty oil). In addition, dosage unit forms can contain various other materials which modify the physical form of the dosage unit, for example, coatings of sugar, shellac, or other enteric agents.

The compound or its salts can also be administered orally as a component of an elixir, suspension, syrup, wafer, chewing gum or the like. A syrup may contain, in addition to the active compounds, a sweetening agent (such as sucrose, saccharine, etc.) and preservatives, dyes and colorings and flavors.

The compounds of the invention may be also administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxpropyl-methyl cellulose; humectants, e.g. glycerin and propylene glycol; acids, bases or buffer substances for adjusting the pH, e.g., citric acid, sodium citrate, phosphoric acid, sodium phospate as well as mixtures of citrate and phosphate buffers; surfactants, e.g. Polysorbate 80; and antimicrobial preservatives, e.g., benzalkonium chloride, phenylethyl alcohol and potassium sorbate.

In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or gas pressure such as the dry-powder inhaler disclosed in the Schering Corporation International Patent Application No. PCT/US92/05225, published 7 Jan. 1993 as well as the Turbuhaler™ (available from Astra Pharmaceutical Products, Inc.) or the Rotahaler™ (available from Allen & Hanburys) which may be used to deliver the aerosolized particles as a finely milled powder in large aggregates either alone or in combination with some pharmaceutically acceptable carrier e.g. lactose; and nebulizers.

Solutions or suspensions used for parenteral, intradermal, subcutaneous, or topical application can include at least some of the following components: a sterile diluent (such as water for injection, saline solution, fixed oils, polyethylene glycols, glycerine, propylene glycol or other synthetic solvents); antibacterial agents (such as benzyl alcohol or methyl parabens); antioxidants (such as ascorbic acid or sodium bisulfite); chelating agents (such as ethylenediaminetetraacetic acid); buffers (such as acetates, citrates or phosphates); and/or agents for the adjustment of tonicity (such as sodium chloride or dextrose). The pH of the solution or suspension can be adjusted with acids or bases, such as hydrochloric acid or sodium hydroxide.

A parenteral preparation can be enclosed in ampoules, disposable syringes or multiple dose vials made of glass or plastic.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

If administered intravenously, carriers can be physiological saline, bacteriostatic water, Cremophor EL™ (BASF, Parsippany, N.J.) or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Dosing

The compound is administered for a sufficient time period to alleviate the undesired symptoms and the clinical signs associated with the condition being treated. In one embodiment, the compounds are administered less than three times daily. In one embodiment, the compounds are administered in one or two doses daily. In one embodiment, the compounds are administered once daily. In some embodiments, the compounds are administered in a single oral dosage once a day.

The active compound is included in the pharmaceutically acceptable carrier or diluent in an amount sufficient to deliver to a patient a therapeutic amount of compound in vivo in the absence of serious toxic effects. An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

Typical systemic dosages for the herein described conditions are those ranging from 0.01 mg/kg to 1500 mg/kg of body weight per day as a single daily dose or divided daily doses. Preferred dosages for the described conditions range from 0.5-1500 mg per day. A more particularly preferred dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as a single daily dose or divided daily doses. In one embodiment, the daily dose is between 10 and 500 mg/day. In another embodiment, the dose is between about 10 and 400 mg/day, or between about 10 and 300 mg/day, or between about 20 and 300 mg/day, or between about 30 and 300 mg/day, or between about 40 and 300 mg/day, or between about 50 and 300 mg/day, or between about 60 and 300 mg/day, or between about 70 and 300 mg/day, or between about 80 and 300 mg/day, or between about 90 and 300 mg/day, or between about 100 and 300 mg/day, or about 200 mg/day. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

Combination Treatment

The compound can also be mixed with other active materials which do not impair the desired action, or with materials that supplement the desired action. The active compounds can be administered in conjunction, i.e. combination or alternation, with medications used in the treatment or prevention neuropathic pain, stroke, traumatic brain injury, epilepsy, and other neurologic events or neurodegeneration resulting from NMDA receptor activation or with medications used in the treatment or prevention neuropsychiatric disorders, such as those in which NMDA receptor activation is involved. In certain embodiment, the compounds can be administered in conjunction (combination or alternation) with other medications used in treatment or prophylaxis of inflammatory conditions. In certain embodiments, the combination can be synergistic.

Emergency treatment for an ischemic stroke, particularly when the stroke is diagnosed within 3 hours of the start of symptoms, includes thrombolytic, or clot-dissolving, medications such as tissue plasminogen activator (t-PA). Other treatments of an ischemic stroke involve administering to the patient an antiplatelet medication (aspirin, clopidogrel, dipyridamole), or anticoagulant medication (warfarin), dependent on the cause. Dextrorphan, a pharmacologically active metabolite of the cough suppressant dextromethorphan, is an NMDAR antagonists studied in human stroke patients. Selfotel, a competitive NMDAR antagonist, was also tested in human patients, however treated patients trended toward higher mortality than within placebo-treated cohorts, and therefore, trials were stopped prematurely. A trial of another NMDA receptor antagonist, aptiganel HCl (Cerestat), was terminated. A large, 1367-patient, efficacy trial with the agent GV150526 was completed in 2000. (http://www.emedicine.com/neuro/topic488.htm, Lutsep & Clark "Neuroprotective Agents in Stroke", Apr. 30, 2004).

In one embodiment, the compound is administered in combination or alternation with a compound useful for the treatment of neurological disorders. In certain embodiments, the compound is administered in combination or alternation with a compound useful for treatment of neuropsychiatric disorders, such as a selective serotonin reuptake inhibitor (SSRI), a serotonin and norepinephrine reuptake inhibitor (SNRI), norepinephrine and dopamine reuptake inhibitor (NDRI), combined reuptake inhibitor and receptor blocker, tetracyclic antidepressant, tricyclic antidepressants (TCAs) (although TCAs tend to have numerous and severe side effects), or a monoamine oxidase inhibitor (MAOI).

Electroconvulsive therapy (ECT) can also be used to treat depression in conjunction with administration of a compound of the invention. Non-traditional treatment options include vagus nerve stimulation, transcranial magnetic stimulation and deep brain stimulation.

SSRIs include fluoxetine (Prozac, Sarafem), paroxetine (Paxil), sertraline (Zoloft), citalopram (Celexa) and escitalopram (Lexapro). SSRIs that have been approved by the Food and Drug Administration specifically to treat depression are: Citalopram (Celexa), Escitalopram (Lexapro), Fluoxetine (Prozac, Prozac Weekly), Paroxetine (Paxil, Paxil CR) and Sertraline (Zoloft). SNRIs that have been approved by the Food and Drug Administration specifically to treat depression are: Duloxetine (Cymbalta) and Venlafaxine (Effexor, Effexor XR). The only NDRI that has been approved by the Food and Drug Administration specifically to treat depression is Bupropion (Wellbutrin, Wellbutrin SR, Wellbutrin XL). The only tetracyclic antidepressant that has been approved by the Food and Drug Administration specifically to treat depression is Mirtazapine (Remeron, Remeron SolTab). Other compounds approved for treatment of neuropsychiatric disorders include Anafranil (clomipramine HCl); Aventyl (nortriptyline HCl); Desyrel (trazodone HCl); Elavil (amitriptyline HCl); Limbitrol (chlordiazepoxide/amitriptyline); Ludiomil (Maprotiline HCl); Luvox (fluvoxamine maleate); Marplan (isocarboxazid); Nardil (phenelzine sulfate); Norpramin (desipramine HCl); Pamelor (nortriptyline HCl); Parnate (tranylcypromine sulfate); Pexeva (paroxetine mesylate); Prozac (fluoxetine HCl); Sarafem (fluoxetine HCl); Serzone (nefazodone HCl); Sinequan (doxepin HCl); Surmontil (trimipramine); Symbyax (olanzapine/fluoxetine); Tofranil (imipramine HCl); Tofranil-PM (impiramine pamoate); Triavil (Perphenaine/Amitriptyline); Vivactil (protriptyline HCl); Wellbutrin (bupropion HCl); and Zyban (bupropion HCl). Combined inhibitors and blockers that have been approved by the Food and Drug Administration specifically to treat depression are: Trazodone, Nefazodone and Maprotiline.

Tricyclic antidepressants (TCAs) inhibit the reabsorption (reuptake) of serotonin and norepinephrine. They were among the earliest of antidepressants, hitting the market in the 1960s, and they remained the first line of treatment for depression through the 1980s, before newer antidepressants arrived. TCAs that have been approved by the Food and Drug Administration specifically to treat depression are: Amitriptyline, Amoxapine, Desipramine (Norpramin), Doxepin (Sinequan), Imipramine (Tofranil), Nortriptyline (Pamelor), Protriptyline (Vivactil) and Trimipramine (Surmontil)

MAOIs that have been specifically approved by the Food and Drug Administration to treat depression are: Phenelzine (Nardil), Tranylcypromine (Parnate), Isocarboxazid (Marplan) and Selegiline (Emsam). Emsam is the first skin (transdermal) patch for depression.

Any of the compounds of the invention can be administered in combination with another active agent. In certain embodiments, the second active is one that is effective in treatment of a neuropsychiatric disorder. However, in certain other embodiments, the second active is one that is effective against an underlying disorder that is associated with a neuropsychiatric symptom. Examples of such disorders are heart disease, Alzheimer's disease and Parkinson's diseases. In certain embodiments, the compounds can be administered in combination in a single dosage form or injection, or administered concurrently. In other embodiments, the compounds are administered in alternation.

EXAMPLES

The following examples are provided to illustrate the present invention and are not intended to limit the scope thereof. Those skilled in the art will readily understand that known variations of the conditions and processes of the following preparative procedures can be used to manufacture the desired compounds. The materials required for the embodiments and the examples are known in the literature, readily commercially available, or can be made by known methods from the known starting materials by those skilled in the art.

Example 1

Preparation of (E)-6-((1-(3-(3,4-dichlorophenyl) acryloyl)piperidin-4-yl)methoxy)-3,4-dihydroquinolin-2(1H)-one (6) (Scheme 1)

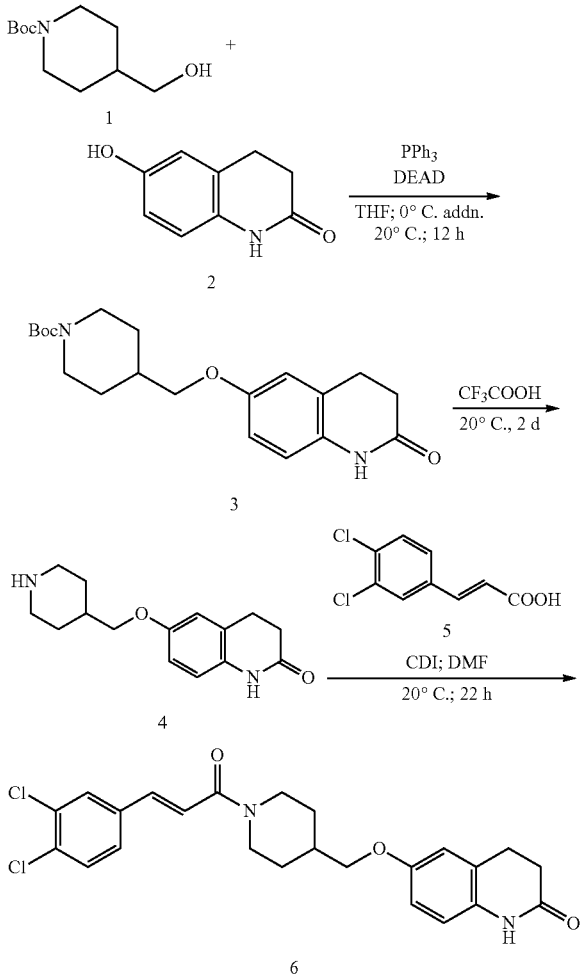

Step 1: Preparation of tert-butyl 4-(((2-oxo-1,2,3,4-tetrahydroquinolin-6-yl)oxy)methyl)-piperidine-1-carboxylate (3) (Scheme 1)

Diethylazodicarboxylate (40% solution in toluene, 3.3 mL, 7.4 mmol) was added to a mixture of 6-hydroxy-3,4-dihydro-2(1H)-quinolinone (2) (1.0 g, 6.1 mmol), triphenylphosphine (1.607 g, 6.1 mmol), and N-Boc-4-piperidinemethanol (1) (1.32 g, 6.1 mmol) in anhydrous tetrahydrofuran (25 mL) at 0° C. After the addition, the mixture was stirred at 20° C. for 16 h. The reaction mixture was diluted with brine (20 mL) and stirred for 30 min. The mixture was extracted with ethyl acetate (2×30 mL), and washed with brine. The combined organic extract was dried over Na$_2$SO$_4$, and later evaporated on a rotavap. The residue was purified by flash column chromatography on silica gel (230-400 mesh; 8 g) using hexane: ethylacetate solvent mixture. Yield: 3.02 g (some phosphorus side products were present, used without further purification for subsequent step). $^1$H NMR (400 MHz, CDCl$_3$): δ 7.84 (s, 1H), 6.70 (b.s, 1H), 6.67 (m, 2H), 3.74 (d, 2H), 2.91 (t, 2H), 2.70 (b.t, 2H), 2.59 (m, 2H), 1.93 (b.s, 1H), 1.80 (b.d, 2H), 1.44 (m, 9H), 1.24 (m, 2H).

Step 2: Preparation of 6-(piperidin-4-ylmethoxy)-3,4-dihydroquinolin-2(1H)-one (4) (Scheme 1)

Trifluoroacetic acid (6.18 mL, 83 mmol) was added to a stirred mixture of compound 3 (~6.1 mmol, product obtained from previous step) in dichloromethane (30 mL) at 20° C. The mixture was evaporated after 2 d to colorless oil. The reaction mixture was cooled to room temperature and volatiles were evaporated on a rotavap. The residue was neutralized with few mL of ammonia and later purified on by flash column chromatography using silica gel (230-400 mesh; 12 g) and dichloromethane:methanol:ammonia solvent mixture (90:10:1) as eluant. Yield: 0.75 g (47.2%). $^1$H NMR (400 MHz, DMSO-d$_6$): δ 9.86 (s, 1H), 6.72 (b.s, 1H), 6.65 (m, 2H), 3.67 (d, 2H), 3.40 (b.s, 1H), 2.93 (d, 2H), 2.77 (t, 2H), 2.51 (m, 2H), 2.34 (t, 2H), 1.975 (b.m, 1H), 1.66 (d, 2H), 1.09 (m, 2H). ES-MS m/z 261.16 (C$_{15}$H$_{20}$N$_2$O$_2$+1)$^+$.

Step 3: Preparation of (E)-6-((1-(3-(3,4-dichlorophenyl)acryloyl)piperidin-4-yl)methoxy)-3,4-dihydroquinolin-2(1H)-one (6) (Scheme 1)

A mixture of 3,4-dichlorocinnamic acid (0.125 g, 0.58 mmol), 4-(dimethylamino)-pyridine (0.005 g, 0.04 mmol) and 1,1'-carbonyldiimidazole (0.098 g, 0.61 mmol) was stirred in DMF at 20° C. After 6 h, the secondary amine piperidine reagent 4 (0.15 g, 0.58 mmol) was added to the reaction mixture and stirred for 16 h. The mixture was diluted with brine and extracted with dichloromethane (2×30 mL). The combined extract was washed with brine, dried over Na$_2$SO$_4$, and later evaporated on a rotavap. The residue was purified by flash column chromatography on silica gel (230-400 mesh; 8 g) using dichloromethane:methanol:ammonia solvent mixture (95:5:0.05). The product was triturated with ether and filtered. Yield: 0.14 g (52.9%). $^1$H NMR (400 MHz, DMSO-d$_6$): δ 9.86 (s, 1H), 8.08 (s, 1H), 7.67 (d, 1H), 7.61 (d, 1H), 7.39 (m, 2H), 6.74 (m, 1H), 6.68 (m, 2H), 4.46 (d, 1H), 4.31 (d, 1H), 3.75 (d, 2H), 3.03 (t, 1H), 2.76 (t, 2H), 2.65 (t, 1H), 2.35 (t, 2H), 1.98 (b.m, 1H), 1.78 (b.m, 2H), 1.15 (m, 2H). ES-MS m/z 459.12 (C$_{24}$H$_{24}$Cl$_2$N$_2$O$_3$+1)$^+$. Analysis calculated for C$_{24}$H$_{24}$Cl$_2$N$_2$O$_3$: % C, 62.75; H, 5.27; N, 6.10. Found: % C, 62.65; % H, 5.42; % N, 6.31.

Alternate Synthetic Route to Compound 3 (Scheme 1b) Used in Example 1

Scheme 1b:

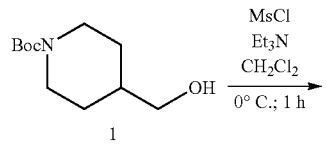

Step 1: Preparation of Mesyl derivative 7

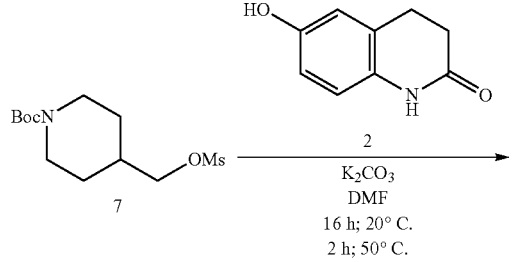

A mixture of N-Boc-4-piperidinemethanol (1) (1.50 g, 6.9 mmol) and triethyl amine (1.96 mL, 14.0 mmol) in 40 mL of dichloromethane was stirred at 0° C. Methane sulfonyl chloride (1.09 mL, 14.0 mmol) was added dropwise to the mixture. After 1 h, the reaction mixture was quenched with water (15 mL) and brine (15 mL). The organic layer was separated, dried over sodium sulfate and evaporated. A pale yellow solid was obtained. Crude=2.4 g. $^1$H NMR (400 MHz, DMSO-d$_6$): δ 4.06 (d, 2H), 3.95 (b.d, 2H), 3.17 (s, 3H), 2.7 (b.s, 2H), 2.39, 1.85 (b.s, 1H), 1.64 (b.d, 2H), 1.39 (s, 9H), 1.08 (m, 2H).

Step 2: Preparation of tert-butyl 4-(((2-oxo-1,2,3,4-tetrahydroquinolin-6-yl)oxy)methyl)-piperidine-1-carboxylate (3) from Mesyl derivative 7

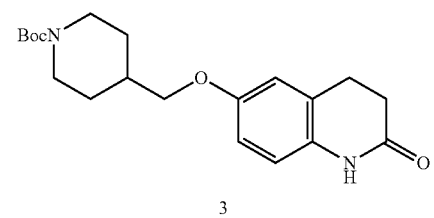

Mesyl compound 7 (0.3 g, ~1.0 mmol) was added to a stirred suspension of 6-hydroxy-3,4-dihydro-2(1H)-quinolinone (2) (0.167 g, 1.0 mmol), and powdered potassium carbonate (0.141 g, 1.0 mmol) in dimethylformamide (5 mL). After stirring for 16 h at 20° C., the mixture was heated at 50° C. for 2 h. Cooled to room temperature and diluted with sodium bicarbonate solution. The mixture was extracted with ethyl acetate (2×30 mL), which was washed with brine. The extract was dried over Na$_2$SO$_4$, and evaporated on a rotavap. The residue was purified by flash column chromatography on silica gel (230-400 mesh; 12 g) using dichloromethane:methanol:NH$_4$OH (95:5:0.05). Yield=0.08 g. $^1$H NMR (400 MHz, CDCl$_3$): δ 10.18 (s, 1H), 7.16 (b.s, 1H), 7.13 (m, 1H), 6.86 (d, 1H), 4.04 (d, 2H), 3.91 (b.d, 2H), 2.85 (t, 2H), 2.64 (b.s, 2H), 2.42 (t, 2H), 1.80 (b.s, 1H), 1.61 (b.d, 2H), 1.36 (m, 9H), 1.06 (m, 2H).

Example 2

Preparation of 4-chlorobenzyl 4-(((2-oxo-1,2,3,4-tetrahydroquinolin-6-yl)oxy)methyl)piperidine-1-carboxylate (11) (Scheme 2)

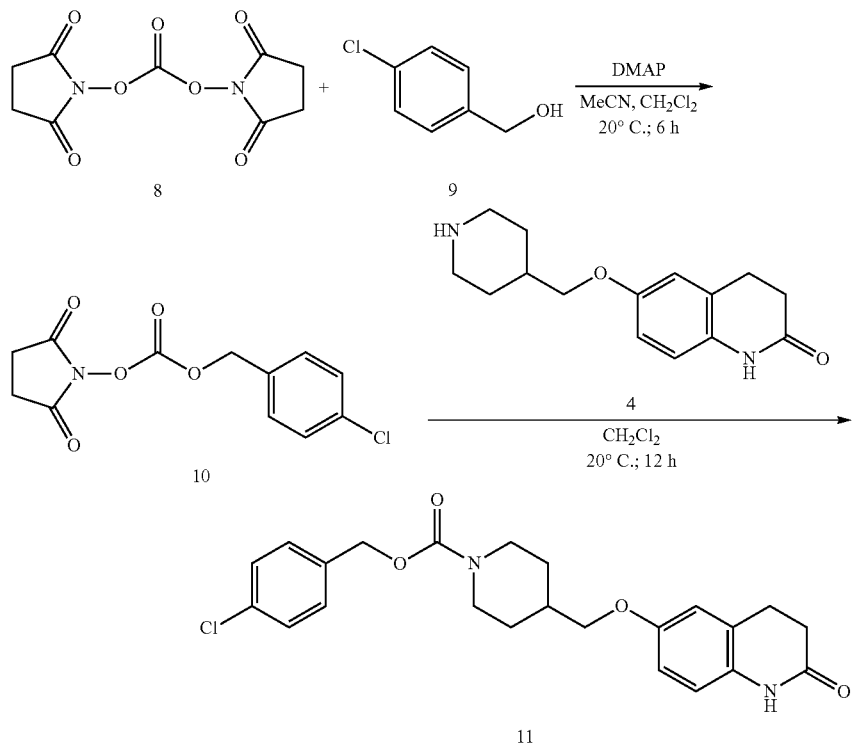

Step 1: Preparation of 4-chlorobenzyl (2,5-dioxopyrrolidin-1-yl)carbonate (10) (Scheme 2)

Compound N,N'-disuccinimidyl carbonate 8 (2.5 g, 9.8 mmol) was added to a stirred solution of 4-chlorobenzyl alcohol 9 (1.39 g, 9.7 mmol) and 4-(dimethylamino)pyridine (0.596 g, 4.9 mmol) in a solvent mixture of acetonitrile (15 mL) and dichloromethane (15 mL) at 20° C. After 6 h, the mixture was diluted with water (15 mL) and brine (5 mL). The resulting mixture was extracted with dichloromethane (30 mL) and washed with brine. The extract was dried over $Na_2SO_4$, and evaporated. A white solid was obtained, which was triturated with ether and filtered. Yield=2.2 g (79.6%). $^1$H NMR (400 MHz, $CDCl_3$): δ 7.36 (m, 4H), 5.25 (s, 2H), 2.82 (s, 4H).

Step 2: Preparation of 4-chlorobenzyl 4-(((2-oxo-1,2,3,4-tetrahydroquinolin-6-yl)oxy)methyl)piperidine-1-carboxylate (11) (Scheme 2)

To a solution of succinimidyl derivative 10 (0.109 g, 3.8 mmol) in dichloromethane (5 mL) at 0° C. was added the secondary amine piperidine derivative 4 (0.100 g, 0.38 mmol). A clear solution was obtained upon stirring. After 12 h at 20° C., the mixture was diluted with dichloromethane (25 mL) and washed with brine. The resulting solution was dried over $Na_2SO_4$, and later evaporated on a rotavap. The residue was purified by flash column chromatography on silica gel (230-400 mesh; 8 g) using dichloromethane:methanol:ammonia solvent mixture (95:5:0.05). The product was triturated with ether and filtered. Yield: 0.105 g (63.7%). $^1$H NMR (400 MHz, DMSO-$d_6$): δ 9.90 (s, 1H), 7.45 (d, 2H), 7.38 (d, 2H), 6.73 (m, 3H), 5.06 (s, 2H), 4.02 (d, 2H), 3.76 (d, 2H), 2.81 (b.m, 4H), 2.37 (t, 2H), 1.91 (b.m, 1H), 1.75 (d, 2H), 1.17 (m, 2H). ES-MS m/z 429.16 $(C_{23}H_{25}ClN_2O_4+1)^+$. Analysis calculated for $C_{23}H_{25}ClN_2O_4$: % C, 64.41; H, 5.88; N, 6.53. Found: % C, 64.38; % H, 5.88; % N, 6.49.

Example 3

Preparation of N-(4-chlorophenyl)-4-(((2-oxo-1,2,3,4-tetrahydroquinolin-6-yl)oxy)methyl)piperidine-1-carboxamide (13) (Scheme 3)

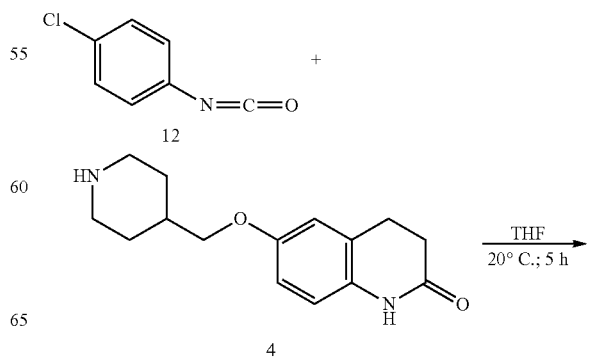

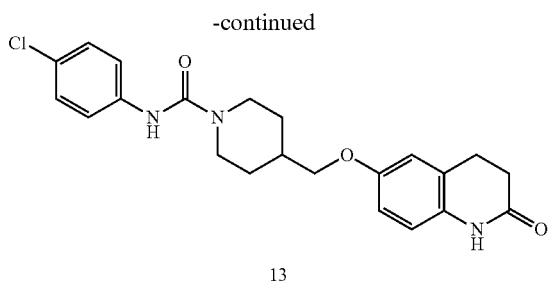

13

To a solution of the secondary amine piperidine derivative 4 (0.100 g, 0.38 mmol) in anhydrous tetrahydrofuran (5 mL) at 0° C. was added 4-chlorophenyl isocyanate 12 (0.059 g, 0.38 mmol). A pale pinkish suspension was obtained, which slowly turned to white. After 5 h, the mixture was filtered and the precipitate was washed with ether (30 mL) and dichloromethane (10 mL). Yield=0.117 g (73.6%). $^1$H NMR (400 MHz, DMSO-d$_6$): δ 9.91 (s, 1H), 8.61 (s, 1H), 7.50 (m, 2H), 7.27 (m, 2H), 6.79 (m, 1H), 6.73 (m, 2H), 4.15 (d, 2H), 3.78 (d, 2H), 2.80 (m, 4H), 2.45 (t, 2H), 1.94 (b.m, 1H), 1.78 (m, 2H), 1.22 (m, 2H). Analysis calculated for C$_{22}$H$_{24}$ClN$_3$O$_3$: % C, 63.84; H, 5.84; N, 10.15. Found: % C, 63.54; % H, 5.87; % N, 9.89.

Example 4

Preparation of 6-((1-(2-(4-chlorophenyl)acetyl)piperidin-4-yl)methoxy)-3,4-dihydroquinolin-2(1H)-one (15) (Scheme 4)

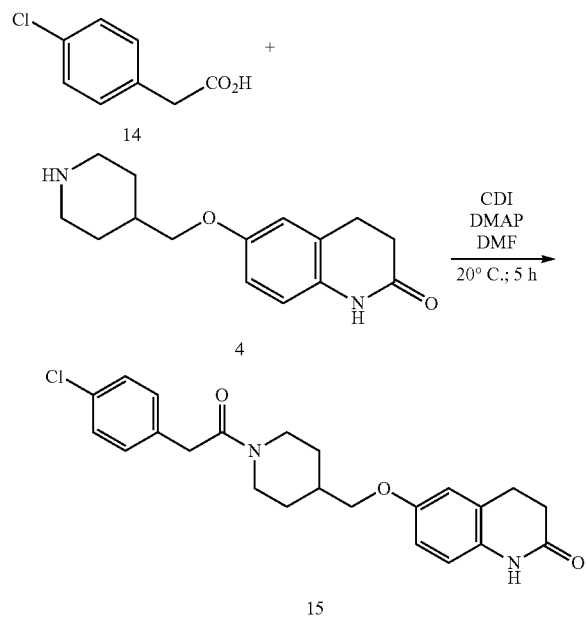

A mixture of 4-chlorophenylacetic acid 14 (0.098 g, 0.58 mmol), 4-(dimethylamino)-pyridine (0.005 g, 0.04 mmol) and 1,1'-carbonyldiimidazole (0.098 g, 0.61 mmol) was stirred in DMF at 20° C. After 5 h, the secondary amine piperidine reagent 4 (0.15 g, 0.58 mmol) was added to the reaction mixture and stirred for 12 h. The mixture was diluted with dichloromethane (50 mL) and washed with brine. The solution was dried over Na$_2$SO$_4$ and evaporated on a rotavap. The residue was purified by flash column chromatography on silica gel (230-400 mesh; 8 g) using dichloromethane:methanol:ammonia solvent mixture (95:5:0.05). The product was triturated with ether and filtered. Yield: 0.21 g (88.3%). $^1$H NMR (400 MHz, DMSO-d$_6$): δ 9.86 (s, 1H), 7.32 (d, 2H), 7.20 (d, 2H), 6.71 (m, 1H), 6.65 (m, 2H), 4.36 (d, 1H), 3.92 (d, 1H), 3.67 (m, 4H), 2.96 (t, 1H), 2.78 (t, 2H), 2.56 (t, 1H), 2.34 (t, 2H), 1.89 (b.m, 1H), 1.68 (b.t, 2H), 1.02 (m, 2H). ES-MS m/z 413.16 (C$_{23}$H$_{25}$ClN$_2$O$_3$+1)$^+$. Analysis calculated for C$_{23}$H$_{25}$ClN$_2$O$_3$: % C, 66.90; H, 6.10; N, 6.78. Found: % C, 67.14; % H, 6.21; % N, 6.90.

Example 5

Preparation of 4-(((2-oxo-1,2,3,4-tetrahydroquinolin-6-yl)oxy)methyl)-N-(4-(trifluoromethyl)phenyl)piperidine-1-carboxamide (17) (Scheme 5)

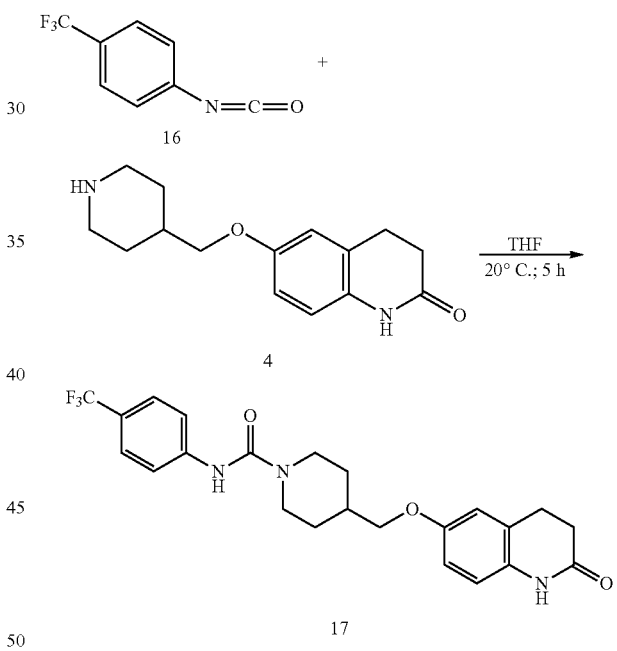

To a solution of secondary amine piperidine derivative 4 (0.120 g, 0.46 mmol) in anhydrous tetrahydrofuran (5 mL) at 20° C. was added 4-(trifluoromethyl)phenyl isocyanate (0.090 g, 0.48 mmol). After 16 h, the mixture was treated with brine (10 mL) and extracted with ethyl acetate (40 mL). The solution was dried over Na$_2$SO$_4$ and evaporated on a rotavap. The residue was purified by flash column chromatography on silica gel (230-400 mesh; 8 g) using dichloromethane:methanol:ammonia solvent mixture (95:5:0.05). The product was triturated with ether and filtered. Yield: 0.20 g (96.9%). $^1$H NMR (400 MHz, DMSO-d$_6$): δ 9.91 (s, 1H), 8.88 (s, 1H), 7.70 (d, 2H), 7.57 (d, 2H), 6.77 (m, 1H), 6.73 (m, 2H), 4.18 (d, 2H), 3.79 (d, 2H), 2.82 (m, 4H), 2.39 (t, 2H), 1.96 (b.m, 1H), 1.79 (d, 2H), 1.19 (m, 2H). ES-MS m/z 448.19

$(C_{23}H_{24}F_3N_3O_3+1)^+$. Analysis calculated for $C_{23}H_{24}F_3N_2O_3$: % C, 61.74; H, 5.41; N, 9.39. Found: % C, 61.33; % H, 5.62; % N, 8.79.

Example 6

Preparation of N-(4-chlorophenyl)-3-(((2-oxo-1,2,3,4-tetrahydroquinolin-6-yl)oxy)methyl)azetidine-1-carboxamide (21) (Scheme 6)

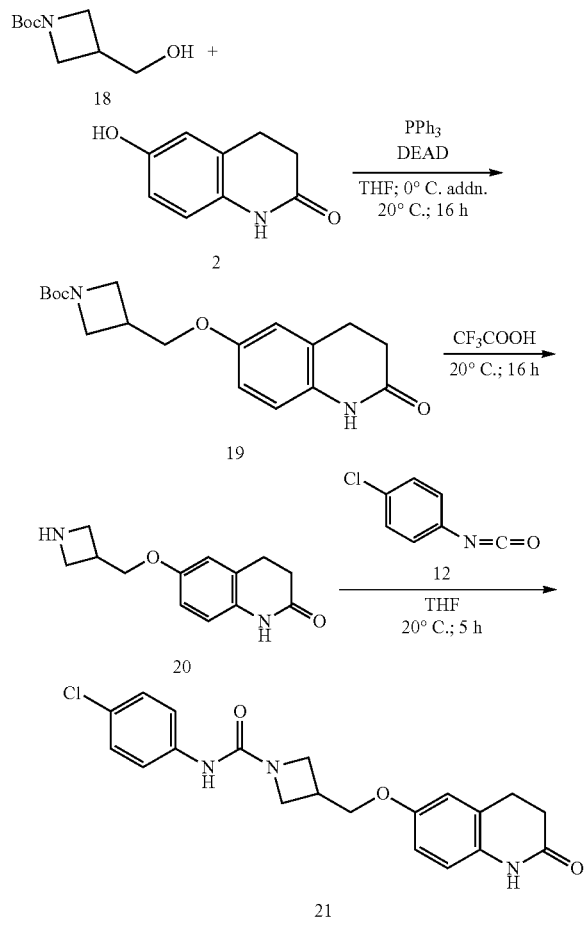

Step 1: Preparation of tert-butyl 3-(((2-oxo-1,2,3,4-tetrahydroquinolin-6-yl)oxy)methyl)azetidine-1-carboxylate (19) (Scheme 6)

Diethylazodicarboxylate (40% solution in toluene, 3.4 mL, 7.4 mmol) was added to a mixture of 6-hydroxy-3,4-dihydro-2(1H)-quinolinone 2 (1.0 g, 6.1 mmol), triphenylphosphine (1.607 g, 6.1 mmol), and 1-boc-azetidine-3-yl-methanol 18 (1.148 g, 6.1 mmol) in anhydrous tetrahydrofuran (25 mL) at 0° C. After the addition, the mixture was stirred at 20° C. for 16 h. The reaction mixture was diluted with brine (20 mL) and stirred for 30 min. The mixture was extracted with ethyl acetate (2×50 mL), and washed with brine. The combined organic extract was dried over $Na_2SO_4$, and later evaporated on a rotavap. The residue was purified by flash column chromatography on silica gel (230-400 mesh; 24 g) using dichloromethane:methanol:methanol (95:5:0.05) solvent mixture. Yield: 4.02 g (some phosphorus side products were present, used without further purification for subsequent step). $^1$H NMR (400 MHz, CDCl$_3$): δ 6.70 (m, 2H), 6.63 (m, 1H), 4.02 (m, 4H), 3.96 (m, 1H), 3.75 (m, 2H), 2.91 (t, 2H), 2.58 (t, 2H), 1.41 (m, 9H).

Step 2: Preparation of 6-(azetidin-3-ylmethoxy)-3,4-dihydroquinolin-2(1H)-one (20) (Scheme 6)

Trifluoroacetic acid (6.00 mL, 81 mmol) was added to a stirred mixture of compound 19 (~6.1 mmol, obtained from previous step) in dichloromethane (30 mL) at 20° C. The mixture was evaporated after 2 d to colorless oil. The reaction mixture was cooled to room temperature and volatiles were evaporated on a rotavap. The residue was neutralized with few mL of ammonia and later purified by flash column chromatography using silica gel (230-400 mesh; 12 g) using dichloromethane:methanol:ammonia solvent mixture (90:10:1). Yield: 0.70 g (49.2%). $^1$H NMR (400 MHz, DMSO-d$_6$): δ 9.91 (s, 1H), 8.80 (b, 1H), 6.79 (m, 1H), 6.73 (m, 2H), 4.02 (m, 4H), 3.80 (m, 2H), 3.12 (m, 1H), 2.77 (t, 2H), 2.36 (t, 2H). ES-MS m/z 233.13 $(C_{13}H_{16}N_2O_2+1)^+$.

Step 3: Preparation of N-(4-chlorophenyl)-3-(((2-oxo-1,2,3,4-tetrahydroquinolin-6-yl)oxy)methyl)azetidine-1-carboxamide (21) (Scheme 6)

Compound 4-chlorophenyl isocyanate 12 (0.088 g, 0.57 mmol) was added to a solution of the secondary amine azetidine derivative 20 (0.200 g, 0.86 mmol) in anhydrous tetrahydrofuran (5 mL) at 20° C. A clear solution was obtained at once, which turned to a white suspension in 10 minutes. After 16 h, the mixture was filtered and the precipitate was washed with water (10 mL). The precipitate was partitioned between water (10 mL) and dichloromethane (30 mL). The organic layer was separated, dried over $Na_2SO_4$ and evaporated. Later, the residue was purified by combiflash silica gel column (12 g) using gradient hexane:ethyl acetate (50:50 to 0:100). Yield=0.070 g (21.1%)+an impure fraction was also collected. $^1$H NMR (400 MHz, DMSO-d$_6$): δ 9.92 (s, 1H), 8.54 (s, 1H), 7.53 (d, 2H), 7.27 (d, 2H), 6.83 (s, 1H), 6.76 (s, 2H), 4.07 (m, 4H), 3.77 (m, 2H), 2.96 (b.m, 1H), 2.81 (t, 2H), 2.41 (t, 2H). ES-MS m/z 386.13 $(C_{20}H_{20}ClN_3O_3+1)^+$.

Example 7

Preparation of N-(3,4-dichlorophenyl)-3-(((2-oxo-1,2,3,4-tetrahydroquinolin-6-yl)oxy)methyl)azetidine-1-carboxamide (23) (Scheme 7)

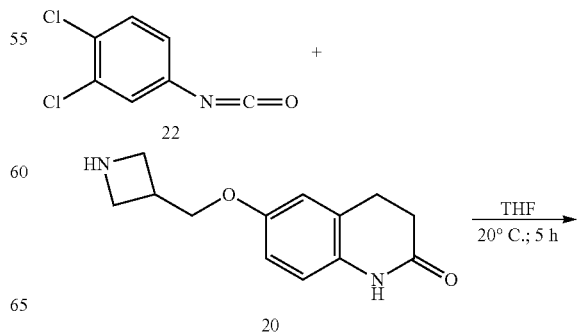

-continued

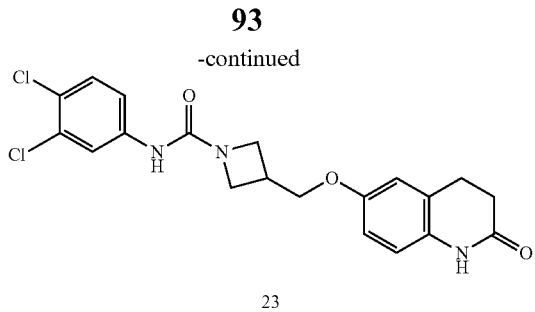

23

Compound 3,4-dichlorophenyl isocyanate 22 (0.081 g, 0.43 mmol) was added to a solution of the secondary amine azetidine derivative 20 (0.100 g, 0.43 mmol) in anhydrous tetrahydrofuran (5 mL) at 20° C. A clear solution was obtained after mixing the reagents but in 30 min turned into a white suspension. After 16 h, diluted with 10 mL of water and stirred for 10 min. The suspension was filtered and the precipitate was washed with water (15 mL), hexane (5 mL) and ether (10 mL). Yield=0.16 g (88.4%). $^1$H NMR (400 MHz, DMSO-d$_6$): δ 9.92 (s, 1H), 8.71 (s, 1H), 7.89 (s, 1H), 7.47 (s, 2H), 6.83 (s, 1H), 6.76 (s, 2H), 4.09 (m, 4H), 3.77 (m, 2H), 2.97 (b.m, 1H), 2.82 (t, 2H), 2.41 (t, 2H). ES-MS m/z 420.09 $(C_{20}H_{19}Cl_2N_3O_3+1)^+$. Analysis calculated for $C_{20}H_{19}Cl_2N_3O_3$: % C, 57.15; H, 4.56; N, 10.00. Found: % C, 57.55; % H, 4.59; % N, 10.03.

Example 8

Preparation of 3-(((2-oxo-1,2,3,4-tetrahydroquinolin-6-yl)oxy)methyl)-N-(4-(trifluoromethyl)phenyl)azetidine-1-carboxamide (24) (Scheme 8)

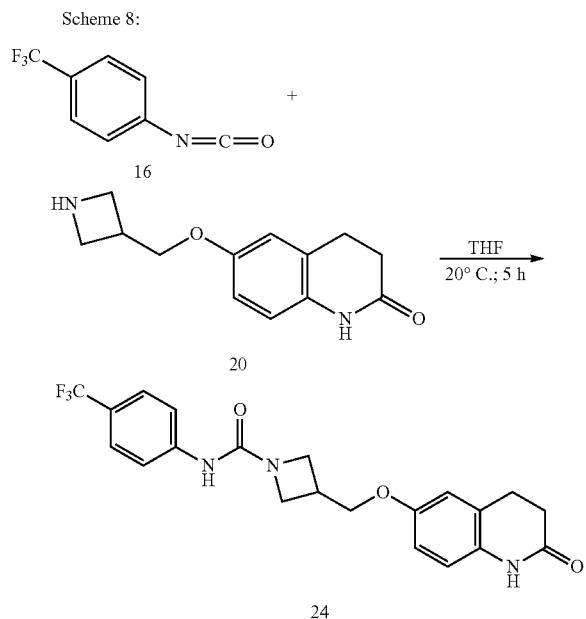

Compound 4-(trifluoromethyl)phenyl isocyanate 16 (0.081 g, 0.43 mmol) was added to a stirred solution of secondary amine azetidine derivative 20 (0.10 g, 0.43 mmol) in anhydrous tetrahydrofuran (5 mL) at 20° C. After 16 h, the mixture was treated with water to obtain a white precipitate. The precipitate was filtered and purified by flash column chromatography on silica gel (230-400 mesh; 8 g) using dichloromethane:methanol:ammonia solvent mixture (95:5: 0.05). Yield: 0.09 g (49.8%). $^1$H NMR (400 MHz, DMSO-d$_6$): δ 9.93 (s, 1H), 8.81 (s, 1H), 7.74 (d, 2H), 7.58 (d, 2H), 6.83 (s, 1H), 6.76 (s, 2H), 4.08 (m, 4H), 3.78 (m, 2H), 2.98 (b.m, 1H), 2.81 (t, 2H), 2.39 (t, 2H). ES-MS m/z 420.15 $(C_{21}H_{20}F_3N_3O_3+1)^+$. Analysis calculated for $C_{21}H_{20}F_3N_3O_3$: % C, 60.14; H, 4.81; N, 10.02. Found: % C, 60.12; % H, 4.82; % N, 10.01.

Example 9

Preparation of 6-((1-(1H-imidazole-1-carbonyl)azetidin-3-yl)methoxy)-3,4-dihydroquinolin-2(1H)-one (26) (Scheme 9)

Scheme 9:

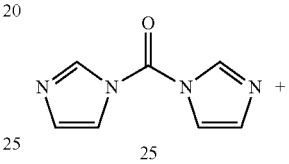

25

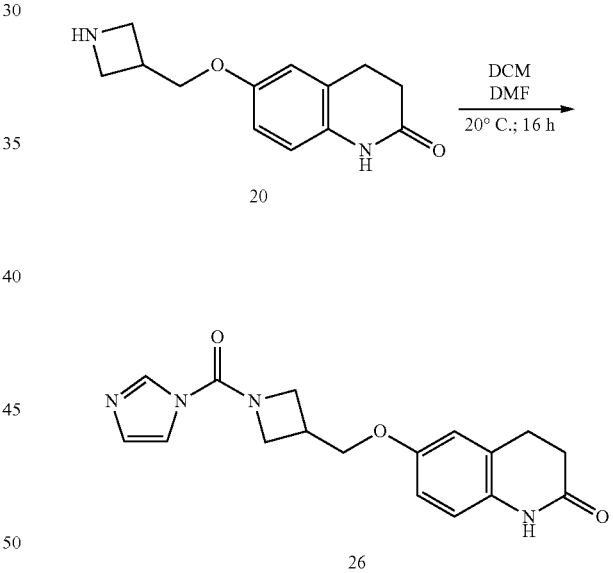

26

A mixture of secondary amine piperidine reagent 20 (0.13 g, 0.56 mmol) and 1,1'-carbonyldiimidazole (0.091 g, 0.56 mmol) was stirred in DMF (5 mL) and dichloromethane (5 mL) at 20° C. for 16 h. The resulting mixture was diluted with water (10 mL) and extracted with dichloromethane (50 mL). The organic solution was washed with brine, dried over Na$_2$SO$_4$ and evaporated on a rotavap. The residue was purified by flash column chromatography on silica gel (230-400 mesh; 8 g) using dichloromethane:methanol:ammonia solvent mixture (95:5:0.05). The product was triturated with ether and filtered. Yield: 0.10 g (54.8%). $^1$H NMR (400 MHz, DMSO-d$_6$): δ 9.89 (s, 1H), 8.08 (s, 1H), 7.49 (s, 1H), 6.99 (s, 1H), 6.77 (s, 1H), 6.71 (m, 2H), 4.25 (b, 1H), 4.18 (b.m, 4H), 3.90 (b, 1H), 3.03 (b.m, 1H), 2.79 (t, 2H), 2.36 (t, 2H). ES-MS m/z 327.14 $(C_{12}H_{18}N_4O_3+1)^+$. Analysis calculated for $C_{12}H_{18}N_4O_3$: % C, 62.57; H, 5.56; N, 17.17. Found: % C, 62.03; % H, 5.50; % N, 16.96.

Example 10

Preparation of N-(4-chlorobenzyl)-3-(((2-oxo-1,2,3,4-tetrahydroquinolin-6-yl)oxy)methyl)azetidine-1-carboxamide (28) (Scheme 10)

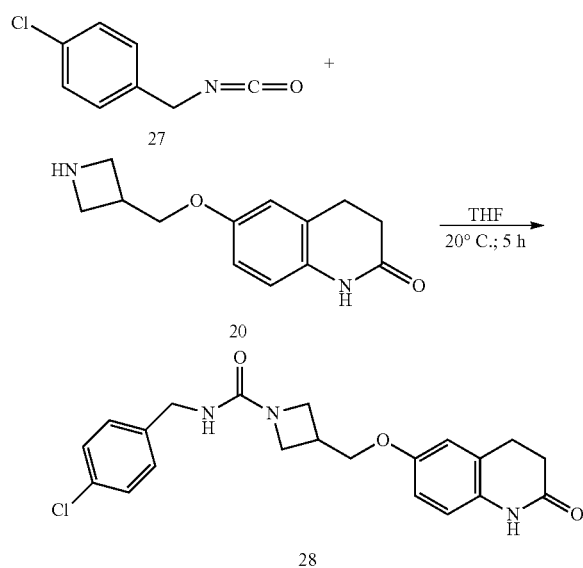

Compound 4-chlorobenzyl isocyanate 27 (0.072 g, 0.43 mmol) was added to a solution of the secondary amine azetidine derivative 20 (0.100 g, 0.43 mmol) in anhydrous tetrahydrofuran (5 mL) at 20° C. The solution was clear after 16 h, which was diluted with water (10 mL) to precipitate the product. The white precipitate obtained was filtered and was washed with water (10 mL), hexane (5 mL) and ether (10 mL). The crude product was purified by combiflash silica gel column (12 g) using gradient dichloromethane:methanol:ammonia (95:5:0.05). Yield=0.12 g (69.7%). $^1$H NMR (400 MHz, DMSO-$d_6$): δ 9.92 (s, 1H), 7.35 (d, 2H), 7.26 (d, 2H), 6.91 (m, 1H), 6.89 (s, 1H), 6.77 (m, 2H), 4.20 (m, 2H), 4.04 (d, 2H), 3.91 (m, 2H), 3.63 (m, 2H), 2.91 (b.m, 1H), 2.83 (t, 2H), 2.41 (t, 2H). ES-MS m/z 400.14 $(C_{21}H_{22}ClN_3O_3+1)^+$. Analysis calculated for $C_{21}H_{22}ClN_3O_3$: % C, 63.08; H, 5.55; N, 10.51. Found: % C, 62.24; % H, 5.49; % N, 10.26.

Example 11

Preparation of N-(4-chlorophenyl)-4-((4-hydroxyphenoxy)methyl)-piperidine-1-carboxamide 33 (Scheme 11)

Similar to the synthesis of 3 shown in Scheme 1, a phenol derivative 30 was prepared under Mitsunobu reaction condition, which demonstrates the versatility of this route in the preparation of these types of compounds with different proton donor groups. The preparation of phenol derivative 33 an analogue of 13 (see Scheme 3) as a result of replacement of proton donor group from dihydroquinolinone to phenol is shown in Scheme 11.

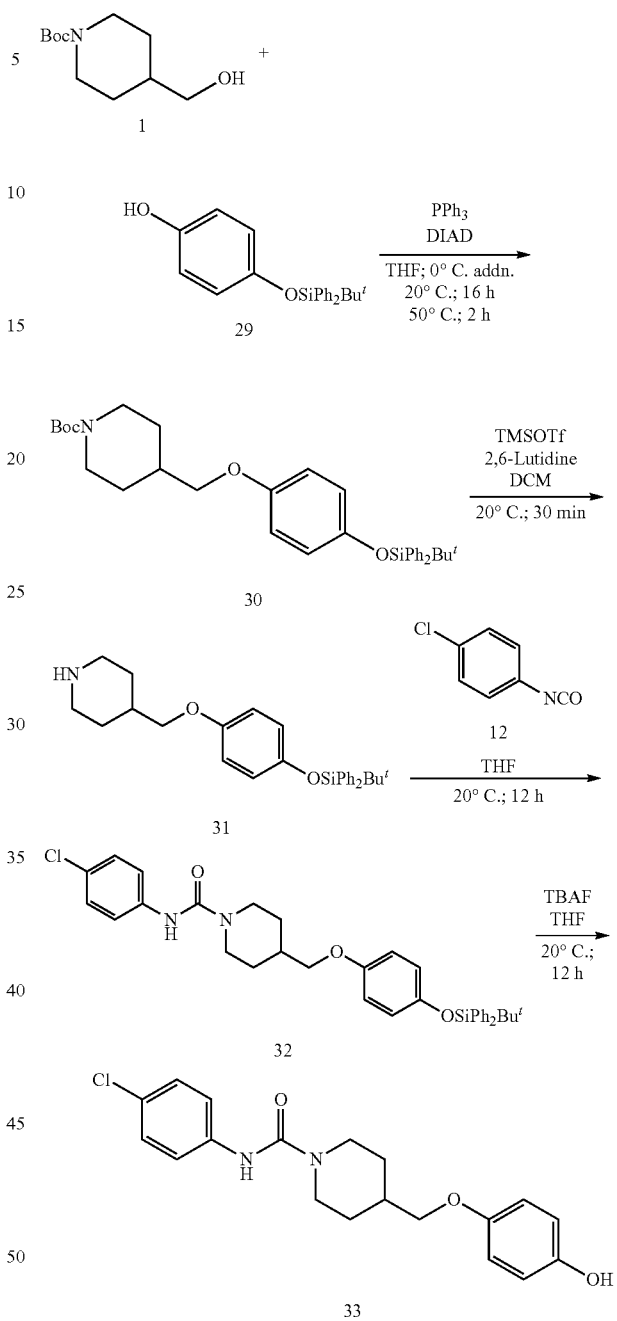

Step 1: Preparation of compound 30 (Scheme 11)

Diisopropylazodicarboxylate (0.95 mL, 4.6 mmol) was added to a mixture of phenol derivative 29 (1.62 g, 4.6 mmol), triphenylphosphine (1.22 g, 4.6 mmol), and N-Boc-4-piperidinemethanol (1) (1.0 g, 4.6 mmol) in anhydrous tetrahydrofuran (20 mL) at 0° C. After the addition, the mixture was stirred at 20° C. for 16 h and later at 50° C. for 2 h. The reaction mixture was diluted with water (15 mL) and ethyl acetate (15 mL). After stirring for 10 min, the organic layer was separated, and washed with brine. The organic extract was dried over Na₂SO₄, and evaporated on a rotavap. The residue was purified by flash column chromatography on silica gel (230-400 mesh; 12 g) using gradient hexane:ethylacetate solvent mixture (90:10 to 0:100). Yield: 1.15 g (45.4%). $^1$H NMR (400 MHz, CDCl₃): δ 7.72 (d, 4H), 7.40 (m, 6H), 6.66 (m, 4H), 4.11 (b.s, 2H), 3.66 (d, 2H), 2.71 (m, 2H), 1.86 (b.s, 1H), 1.76 (d, 2H), 1.45 (s, 9H), 1.22 (m, 2H), 1.09 (s, 9H).

Step 2: Preparation of compound 31 (Scheme 11)

To a pale yellow solution of boc derivative 30 (1.15 g, 2.1 mmol) and 2,6-lutidine (0.86 mL, 7.4 mmol) in dichloromethane (5 mL) was added dropwise trimethylsilyl trifluoromethanesulfonate (1.15 mL, 6.3 mmol). The clear solution was stirred for an hour at room temperature. Later, the reaction was quenched by the addition of saturated NaHCO₃ solution at 10° C. The mixture was extracted with dichloromethane, dried over Na₂SO₄, and evaporated on a rotavap. The residue was purified by flash column chromatography on silica gel (230-400 mesh; 12 g) using dichloromethane: methanol:ammonia (90:10:1). Yield: 0.65 g (69.2%). $^1$H NMR (400 MHz, DMSO-d₆): δ 7.67 (d, 4H), 7.42 (m, 6H), 6.66 (m, 4H), 3.70 (d, 2H), 3.22 (d, 2H), 2.81 (t, 2H), 1.94 (b.s, 1H), 1.82 (d, 2H), 1.36 (b.q, 2H), 1.03 (s, 9H).

Step 3: Preparation of compound 32 (Scheme 11)

To a mixture of secondary amine piperidine derivative 31 (0.20 g, 0.45 mmol), dimethylaminopyridine (0.060 g) and triethylamine (0.2 mL, 1.4 mmol) in anhydrous tetrahydrofuran (5 mL) at 20° C. was added 4-chlorophenyl isocyanate 12 (0.069 g, 0.45 mmol). After 12 h, the mixture was diluted with water (10 mL) and extracted with ethyl acetate (2×25 mL). The organic layer was washed with brine. The residue was purified by flash column chromatography on silica gel (230-400 mesh; 12 g) using gradient hexane:ethylacetate solvent mixture (80:20 to 50:50) gave product. Yield: 0.22 g (81.8%). $^1$H NMR (400 MHz, DMSO-d₆): δ 8.56 (s, 1H), 7.62 (m, 2H), 7.42 (m, 8H), 6.66 (d, 2H), 6.62 (d, 2H), 4.05 (d, 2H), 3.64 (d, 2H), 2.76 (t, 2H), 1.84 (b.s, 1H), 1.68 (d, 2H), 1.17 (m, 2H), 0.99 (s, 9H).

Step 4: Preparation of compound 33 (Scheme 11)

To a solution of silyl derivative 32 (0.22 g, 0.37 mmol) in THF (5 mL) at room temperature was added TBAF solution (1 M THF, 2 mL, 2.0 mmol). The mixture was stirred at 20° C. for 12 h. Later, diluted with saturated ammonium chloride solution and extracted with ethyl acetate (2×30 mL). The organic layer was washed with brine, dried over Na₂SO₄ and evaporated. The residue was purified by flash column chromatography on silica gel (230-400 mesh; 12 g) using gradient hexane:ethylacetate solvent mixture (80:20 to 50:50) gave product. Yield: 0.11 g (83.0%). $^1$H NMR (400 MHz, DMSO-d₆): δ 8.87 (s, 1H), 8.57 (s, 1H), 7.46 (m, 2H), 7.23 (m, 2H), 6.71 (d, 2H), 6.61 (d, 2H), 4.10 (d, 2H), 3.70 (d, 2H), 2.77 (t, 2H), 1.89 (b.s, 1H), 1.74 (d, 2H), 1.18 (m, 2H). ES-MS m/z 361.13 (C₁₉H₂₁ClN₂O₃+1)⁺.

Example 12

Preparation of N-(3,4-dichlorophenyl)-4-((4-hydroxyphenoxy)methyl)-piperidine-1-carboxamide 35 (Scheme 12)

Scheme 12:

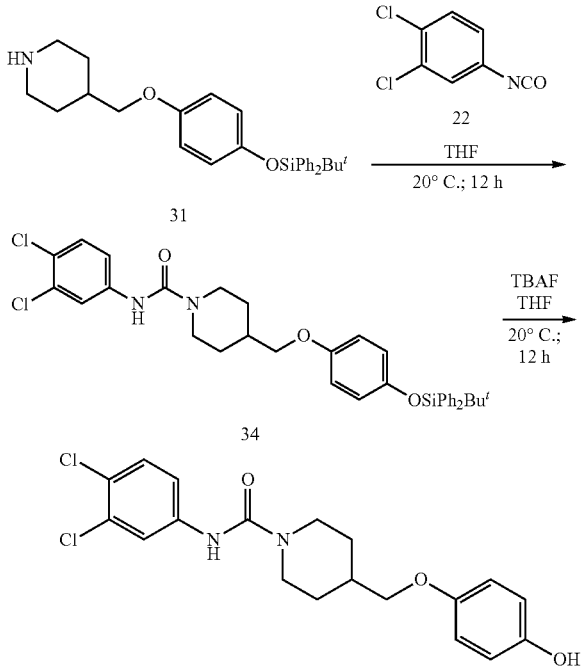

Step 1: Preparation of compound 34 (Scheme 12)

To a mixture of secondary amine piperidine derivative 31 (0.20 g, 0.45 mmol), dimethylaminopyridine (0.060 g) and triethylamine (0.2 mL, 1.4 mmol) in anhydrous tetrahydrofuran (5 mL) at 20° C. was added 3,4-dichlorophenyl isocyanate 22 (0.084 g, 0.45 mmol). After 12 h, the mixture was diluted with water (10 mL) and extracted with ethyl acetate (2×25 mL). The organic layer was washed with brine. The residue was purified by flash column chromatography on silica gel (230-400 mesh; 12 g) using gradient hexane:ethylacetate solvent mixture (80:20 to 50:50) gave product. Yield: 0.16 g (56.3%). $^1$H NMR (400 MHz, DMSO-d₆): δ 8.76 (s, 1H), 7.84 (s, 1H), 7.52 (m, 4H), 7.45 (m, 8H), 6.70 (d, 2H), 6.64 (d, 2H), 4.12 (d, 2H), 3.70 (d, 2H), 2.80 (t, 2H), 1.90 (b.s, 1H), 1.74 (d, 2H), 1.20 (m, 2H), 1.03 (s, 9H).

Step 2: Preparation of compound 35 (Scheme 12)

To a solution of silyl derivative 34 (0.16 g, 0.25 mmol) in THF (5 mL) at room temperature was added TBAF solution (1 M THF, 2 mL, 2.0 mmol). The mixture was stirred at 20° C. for 12 h. Later, diluted with saturated ammonium chloride solution and extracted with ethyl acetate (2×30 mL). The organic layer was washed with brine, dried over $Na_2SO_4$ and evaporated. The residue was purified by flash column chromatography on silica gel (230-400 mesh; 12 g) using gradient hexane:ethylacetate solvent mixture (80:20 to 50:50) gave product. Yield: 0.085 g (86.8%). $^1$H NMR (400 MHz, DMSO-$d_6$): δ 8.87 (s, 1H), 8.73 (s, 1H), 7.81 (s, 1H), 7.42 (m, 2H), 6.70 (d, 2H), 6.61 (d, 2H), 4.11 (d, 2H), 3.71 (d, 2H), 2.77 (t, 2H), 1.89 (b.s, 1H), 1.74 (d, 2H), 1.18 (m, 2H). ES-MS m/z 395.1 $(C_{19}H_{20}Cl_2N_2O_3+1)^+$.

Electrophysiology NMDA Receptor Experiments
and Medicinal Chemistry Data

Example 13

Determination of $IC_{50}$ Values of GluN1/GluN2B Receptors Expressed in *Xenopus oocytes* in Human or Rat Stage V and VI oocytes were surgically removed from the ovaries of large, well-fed and healthy *Xenopus laevis* anesthetized with 3-amino-benzoic acid ethyl ester (3 gm/l). Clusters of isolated oocytes were incubated with 292 U/ml Worthington (Freehold, N.J.) type IV collagenase or 1.3 mg/ml collagenase (Life Technologies, Gaithersburg, Md.; 17018-029) for 2 hr in $Ca^{2+}$-free solution comprised of (in mM) 115 NaCl, 2.5 KCl, and 10 HEPES, pH 7.5, with slow agitation to remove the follicular cell layer. Oocytes were then washed in the same solution supplemented with 1.8 mM $CaCl_2$ and maintained in Barth's solution comprised of (in mM): 88 NaCl, 1 KCl, 2.4 $NaHCO_3$, 10 HEPES, 0.82 $MgSO_4$, 0.33 $Ca(NO_3)_2$, and 0.91 $CaCl_2$ and supplemented with 100 μg/ml gentamycin, 10 μg/ml streptomycin, and 10 μg/ml penicillin. Oocytes were manually defolliculated and injected within 24 hrs of isolation with 3-5 ng of GluN1 subunit cRNA and 7-10 ng of GluN2 cRNA subunit in a 50 nl volume, and incubated in Barth's solution at 18° C. for 2-7 d. Glass injection pipettes had tip sizes ranging from 10-20 microns, and were backfilled with mineral oil. cRNA was synthesized from linearized template cDNA for rat glutamate receptor subunits according to manufacturer specifications (Ambion).

Two electrode voltage-clamp recordings were made 2-7 days post-injection. Oocytes were placed in a dual-track plexiglass recording chamber with a single perfusion line that splits in a Y-configuration to perfuse two oocytes. Dual recordings were made at room temperature (23° C.) using two Warner OC725B two-electrode voltage clamp amplifiers, arranged as recommended by the manufacturer. Glass microelectrodes (1-10 Megaohms) were filled with 300 mM KCl (voltage electrode) or 3 M KCl (current electrode). The bath clamps communicated across silver chloride wires placed into each side of the recording chamber, both of which were assumed to be at a reference potential of 0 mV. Oocytes were perfused with a solution comprised of (in mM) 90 NaCl, 1 KCl, 10 HEPES, 10 EDTA and 0.5 $BaCl_2$; pH was adjusted by addition of 1-3 M NaOH or HCl. Oocytes were recorded under voltage clamp at −40 mV. Final concentrations for glutamate and glycine were 50 μM and 30 μM, respectively. Concentration-response curves for experimental compounds were obtained by applying in successive fashion maximal glutamate/glycine, followed by glutamate/glycine plus variable concentrations of experimental compounds. Dose response curves consisting of 4 to 8 concentrations were obtained in this manner. The baseline leak current at −40 mV was measured before and after recording, and the full recording linearly corrected for any change in leak current. The level of inhibition by applied experimental compounds was expressed as a percent of the initial glutamate response, and averaged together across oocytes from multiple experiments. Results were pooled, and the average percent responses at antagonist concentrations were fit by the equation, $$\text{Percent Response} = (100 - \text{minimum})/(1 + ([\text{conc}]/IC_{50})^{nH}) + \text{minimum}$$

where minimum is the residual percent response in saturating concentration of the experimental compounds, $IC_{50}$ is the concentration of antagonist that causes half of the achievable inhibition, and nH is a slope factor describing steepness of the inhibition curve. Minimum was constrained to be greater than or equal to 0.

Recordings were made at pH 6.9, pH 7.4, and pH 7.6. The pH Boost ratio calculated by dividing the $IC_{50}$ measured at pH 7.6 by the $IC_{50}$ measured at pH 6.9.

TABLE 1

$IC_{50}$ data of GluN1/GluN2B receptors expressed in *Xenopus* oocytes in human or rat

| Compd. | Human pH 7.4 $IC_{50}$ (μM) | # oocytes Hum pH 7.4 | Rat pH 7.4 $IC_{50}$ (μM) | # Rat pH 7.4 oocytes | Human pH 6.9 $IC_{50}$ (μM) | Human pH Boost Ratio ($IC_{50}$ pH 7.6/ $IC_{50}$ pH 6.9) | # oocytes Human pH 7.6 | # oocytes Human pH 6.9 |
|---|---|---|---|---|---|---|---|---|
| 6 | 1.64 | 17 | 1.27 | 18 | 0.886 | 1.1 | 22 | 22 |
| 11 | 0.868 | 17 | 0.837 | 11 | 0.589 | 1.4 | 14 | 15 |
| 13 | 0.468 | 17 | 0.339 | 18 | 0.283 | 2.0 | 20 | 21 |
| 15 | 2.0 | 15 | 3.2 | 18 | 0.490 | 8.6 | 21 | 20 |
| 17 | 0.517 | 17 | 0.359 | 17 | 0.237 | 2.0 | 11 | 10 |
| 21 | 0.170 | 17 | 0.166 | 18 | 0.103 | 1.7 | 15 | 18 |
| 23 | 0.041 | 16 | 0.053 | 17 | 0.019 | 3.0 | 15 | 15 |
| 24 | 0.074 | 17 | 0.054 | 18 | 0.027 | 3.6 | 18 | 18 |
| 26 | >10 | 11 | 6.1 | 9 | >30 | n.d | 12 | 15 |
| 28 | 3.5 | 10 | 4.9 | 11 | 2.3 | 3.5 | 16 | 16 |
| 33 | n.d | n.d | n.d | n.d | 0.740 | 1.8 | 11 | 11 |
| 35 | n.d | n.d | n.d | n.d | 0.764 | 1.2 | 17 | 17 | n.d = not determined

Example 14 hERG and $α_1$-Adrenergic Binding Studies

Binding to the human ether-a-go-go potassium channel (hERG) expressed in HEK293 cells by displacement of 1.5 nM [3H]-astemizole. Each result represents the average of displacement binding experiments done in duplicate at 10 uM of the test compound. Percent displacement of 0.25 nM [3H]- prazosin from Wistar rat brain membranes. Each result represents the average of displacement binding experiments done in duplicate at 3 µM of the test compound.

TABLE 2 hERG and α₁-Adrenergic binding (% displacements) data

| Compound | hERG Binding % Displacement @ 10 µM | α1-Adrenergic binding % Displacement @ 3 µM |
|---|---|---|
| 6 | 85 | 28 |
| 11 | 56 | 16 |
| 13 | 37 | 16 |
| 15 | 18 | 13 |
| 17 | 75 | 7 |
| 21 | 25 | 2 |
| 23 | 60 | 25 |
| 24 | 68 | 12 |
| 26 | <1 | <1 |
| 28 | 27 | 12 |

Example 15

NMDA Receptor Subunit Selectivity

GluN1/GluN2A and GluN1/GluN2D subtype of NMDA receptors were expressed in *Xenopus laevis* as described in Example 13. Here, a 10 µM concentration of the antagonist was perfused with 50 µM glutamate and 30 µM glycine onto the oocyte for two min and the remaining current in the presence of the antagonist was compared to the maximal current obtained with 50 µM glutamate and 30 µM glycine alone (defined as 100%). Results are shown in Table 3.

TABLE 3

GluN2 Selectivity: percent receptor activation remaining after antagonist application.

| Compd | GluN2A % Current Remaining | SEM | N | GluN2D % Current Remaining | SEM | N |
|---|---|---|---|---|---|---|
| 6 | 103.0 | 5.4 | 5 | 101.4 | 2.4 | 4 |
| 11 | 110.9 | 4.6 | 8 | 103.8 | 3.2 | 4 |
| 13 | 104.6 | 2.8 | 7 | 106.0 | 4.7 | 4 |
| 15 | 96.3 | 10.3 | 4 | 101.4 | 2.7 | 4 |
| 17 | 98.7 | 3.2 | 6 | 93.9 | 5.0 | 5 |
| 21 | 101.7 | 2.3 | 5 | 89.2 | 2.0 | 5 |
| 23 | 94.6 | 3.5 | 6 | 87.6 | 2.0 | 5 |
| 24 | 94.2 | 2.6 | 5 | 84.5 | 1.7 | 4 |
| 26 | 101.5 | 2.9 | 4 | 94.9 | 2.0 | 4 |
| 28 | 101.6 | 2.2 | 6 | 94.5 | 1.8 | 6 |
| 33 | 111.0 | 4.0 | 6 | 103.5 | 2.3 | 4 |
| 35 | 103.5 | 4.8 | 7 | 104.4 | 4.5 | 4 |

Example 16

Noncompetitive Block

GluN1/GluN2B-NMDA receptors were expressed in *Xenopus laevis* as described in Example 13 and perfused with glutamate, glycine, and with or without 0.1 µM compound 24. Increasing glutamate (with fixed 30 µM glycine, panel A) and increasing glycine (with fixed 30 µM glutamate, panel B) cannot overcome the block by compound 24. Results shown in FIG. 1 are the Mean±SEM of 7 (panel A) or 6 (panel B) oocytes. The EC₅₀ for glutamate was 0.94 µM without and was 0.57 µM with 0.1 µM compound 24. The EC₅₀ for glycine was 0.23 µM without and was 0.16 µM with 0.1 µM compound 24.

We claim:

1. A compound of Formula I, or a pharmaceutically acceptable salt or ester thereof:

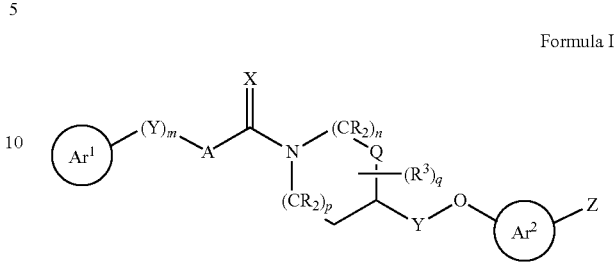

Formula I wherein:

Ar¹ and Ar² are independently substituted or unsubstituted aryl;

m, n, p and q are each independently 0, 1 or 2;

A is a bond, CH₂, CH=CH, C≡C, NR, O or S;

Each R³ is independently selected from C₁-C₆ alkyl, C₃-C₆ cycloalkyl, C₁-C₆ haloalkyl, —OH, O-alkyl, O-aryl, —SH, —S-alkyl, fluoro, chloro, bromo, iodo, nitro, or cyano;

Q is selected from CH₂, CHR, CR₂, NH, NR, O and S;

Each Y is independently CR₂ or CR₂CR₂;

each R is independently selected from H, OH or alkyl, in particular C₁₋₄ alkyl;

X is O or S; and

Z is OH, NR⁶R⁷, NR⁸SO₂(C₁-C₆ alkyl), NR⁸C(O)NR⁶R⁷, NR⁸C(S)NR⁶R⁷, NR⁸CHO, NR⁸C(O)(C₁-C₆ alkyl), NR⁸C(O)O(C₁-C₆ alkyl), NR⁸-dihydrothiazole, or NR⁸-dihydroimidazole wherein each R⁶, R⁷ and R⁸ is independently H, C₁-C₆ alkyl or C₆-C₁₂ aralkyl or Z comes together with Ar² to form a heterocyclic ring

[structure shown]

wherein X² is —O—, —S—, —N(H)—, —N(R)—, —NH—CH₂—, —N=CH—, —NR—CH₂—, —CH₂—N(H)—, —CH₂—N(R)—, —CH₂—, —CH₂—CH₂—, —CH=CH—, —CR—CH₂—, or —CR=CH—; or Z comes together with Ar² to form a heterocyclic ring selected from:

[structures shown]

wherein R⁹ and R¹⁰ are each independently H, C₁-C₆ alkyl or aralkyl.

2. A compound of Formula I-a, or a pharmaceutically acceptable salt or ester thereof:

wherein:
- each R¹ is independently selected from C₁-C₆ alkyl, C₃-C₆ cycloalkyl, C₁-C₆ haloalkyl, —OH, O-alkyl, O-aryl, —SH, —S-alkyl, fluoro, chloro, bromo, iodo, nitro, or cyano; or two R¹ may be taken together with Ar¹ to form a bicyclic ring system;
- each R² and R³ is independently selected from C₁-C₆ alkyl, C₃-C₆ cycloalkyl, C₁-C₆ haloalkyl, —OH, O-alkyl, O-aryl, —SH, —S-alkyl, fluoro, chloro, bromo, iodo, nitro, or cyano;
- r is independently selected from 0, 1, 2, 3, 4 or 5; and
- s is independently selected from 0, 1, 2, 3, 4 or 5;
- Ar¹ and Ar² are independently substituted or unsubstituted aryl;
- m, n, p and q are each independently 0, 1 or 2;
- A is a bond, CH₂, CH=CH, C≡C, NR, O or S;
- Q is selected from CH₂, CHR, CR₂, NH, NR, O and S;
- each Y is independently CR₂ or CR₂CR₂;
- each R is independently selected from H, OH or alkyl, in particular C₁₋₄ alkyl;
- X is O or S; and
- Z is OH, NR⁶R⁷, NR⁸SO₂(C₁-C₆ alkyl), NR⁸C(O)NR⁶R⁷, NR⁸C(S)NR⁶R⁷, NR⁸CHO, NR⁸C(O)(C₁-C₆ alkyl), NR⁸C(O)O(C₁-C₆ alkyl), NR⁸-dihydrothiazole, or NR⁸-dihydroimidazole wherein each R⁶, R⁷ and R⁸ is independently H, C₁-C₆ alkyl or C₆-C₁₂ aralkyl or Z comes together with Ar² to form a heterocyclic ring wherein X² is —O—, —S—, —N(H)—, —N(R)—, —NH—CH₂—, —N=CH—, —NR—CH₂—, —CH₂—N(H)—, —CH₂—N(R)—, —CH₂—, —CH₂—CH₂—, —CH=CH—, —CR—CH₂—, or —CR=CH—; or Z comes together with Ar² to form a heterocyclic ring selected from:

wherein R⁹ and R¹⁰ are each independently H, C₁-C₆ alkyl or aralkyl.

3. A compound of Formula I-b, or a pharmaceutically acceptable salt or ester thereof:

wherein
- m, n, p and q are each independently 0, 1 or 2;
- A is a bond, CH₂, CH=CH, C≡C, NR, O or S;
- each R³ is independently selected from C₁-C₆ alkyl, C₃-C₆ cycloalkyl, C₁-C₆ haloalkyl, —OH, O-alkyl, O-aryl, —SH, —S-alkyl, fluoro, chloro, bromo, iodo, nitro, or cyano;
- each Y is independently CR₂ or CR₂CR₂;
- each R is independently selected from H, OH or alkyl, in particular C₁₋₄ alkyl;
- X is O or S; and
- Z is OH, NR⁶R⁷, NR⁸SO₂(C₁-C₆ alkyl), NR⁸C(O)NR⁶R⁷, NR⁸C(S)NR⁶R⁷, NR⁸CHO, NR⁸C(O)(C₁-C₆ alkyl), NR⁸C(O)O(C₁-C₆ alkyl), NR⁸-dihydrothiazole, or NR⁸-dihydroimidazole wherein each R⁶, R⁷ and R⁸ is independently H, C₁-C₆ alkyl or C₆-C₁₂ aralkyl or Z comes together with the phenyl moiety to which it is attached to form heterocyclic ring wherein $X^2$ is —O—, —S—, —N(H)—, —N(R)—, —NH—CH$_2$—, —N=CH—, —NR—CH$_2$—, —CH$_2$—N(H)—, —CH$_2$—N(R)—, —CH$_2$—, —CH$_2$—CH$_2$—, —CH=CH—, —CR—CH$_2$—, or —CR=CH—; or the heterocyclic ring selected from:

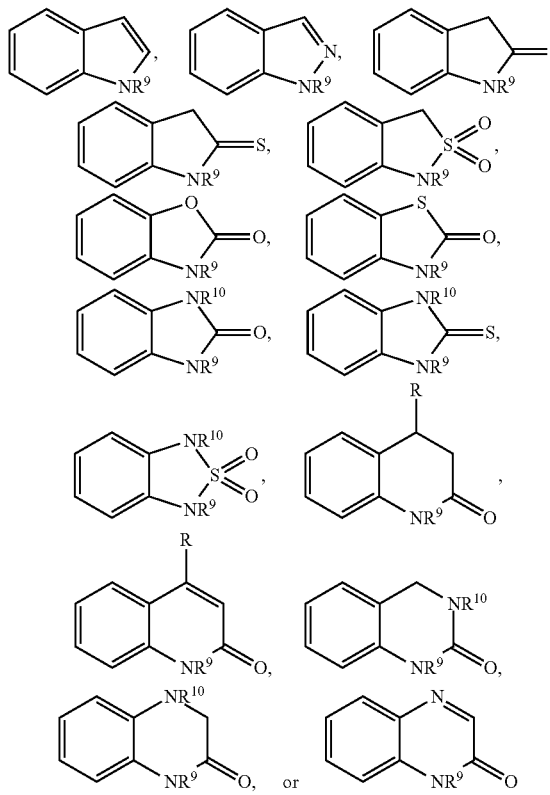

wherein $R^9$ and $R^{10}$ are each independently H, $C_1$-$C_6$ alkyl or aralkyl.

4. The compound of claim 3, wherein Z comes together with the phenyl moiety to which it is attached to form the heterocyclic ring

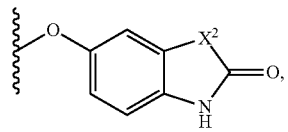

wherein $X^2$ is —O—, —S—, —N(H)—, —N(R)—, —NH—CH$_2$—, —N=CH—, —NR—CH$_2$—, —CH$_2$—N(H)—, —CH$_2$—N(R)—, —CH$_2$—, —CH$_2$—CH$_2$—, —CH=CH—, —CR—CH$_2$—, or —CR=CH—.

5. The compound of claim 3, wherein Z comes together with the phenyl moiety to which it is attached to form a heterocyclic ring selected from:

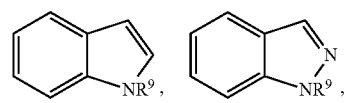

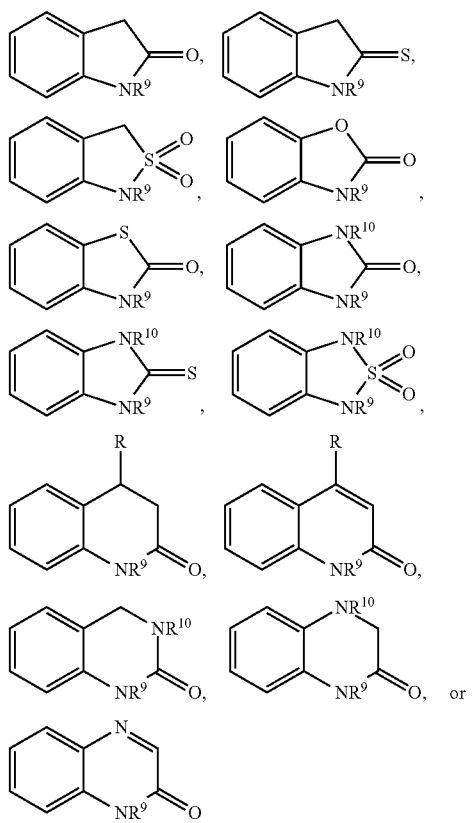

wherein $R^9$ and $R^{10}$ are each independently H, $C_1$-$C_6$ alkyl or aralkyl.

6. The compound of claim 1, wherein the compound is selected from the group consisting of:

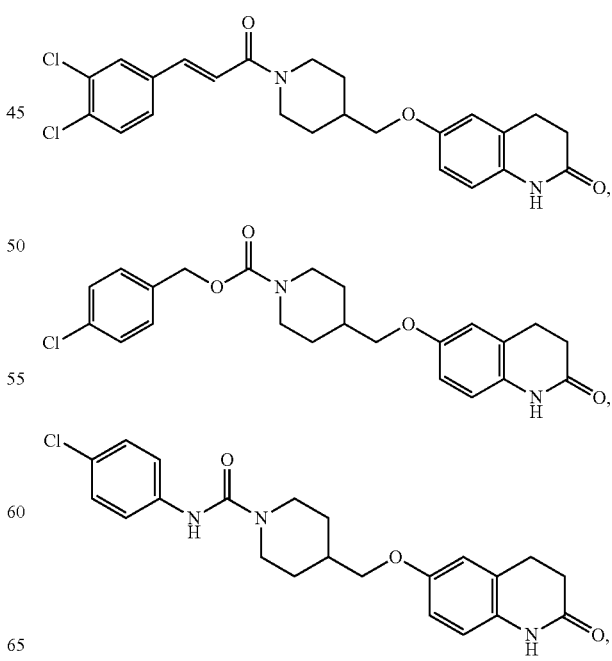

-continued
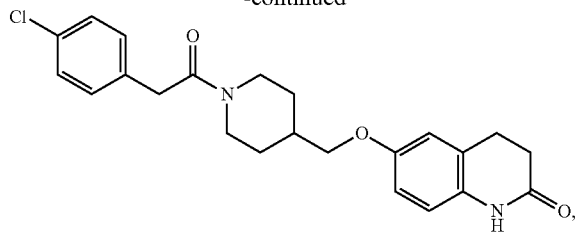
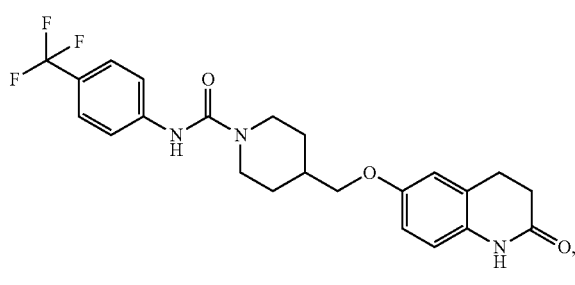
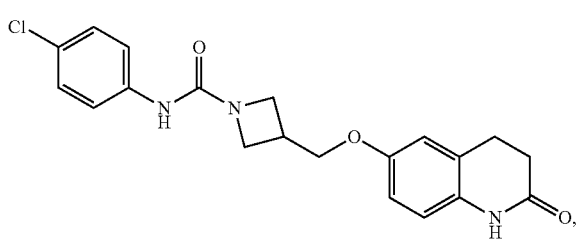
-continued
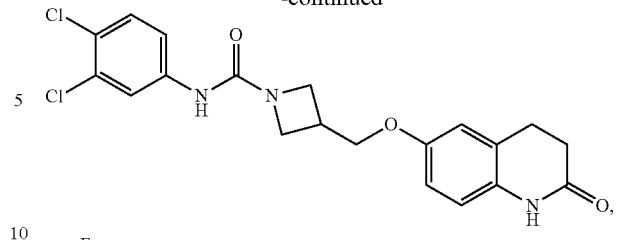
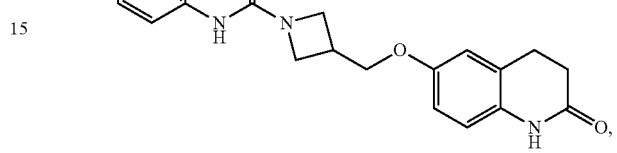
and
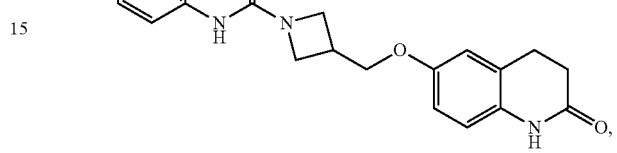
7. A pharmaceutical composition comprising a compound of claim 1 in a pharmaceutically acceptable carrier.
8. A pharmaceutical composition comprising a compound of claim 2 in a pharmaceutically acceptable carrier.
9. A pharmaceutical composition comprising a compound of claim 3 in a pharmaceutically acceptable carrier.
\* \* \* \* \*